US008835451B2

(12) United States Patent
Serrano-Wu et al.

(10) Patent No.: US 8,835,451 B2
(45) Date of Patent: Sep. 16, 2014

(54) COMPOUNDS

(75) Inventors: Michael H. Serrano-Wu, Belmont, MA (US); Young-Shin Kwak, Lexington, MA (US); Wenming Liu, Morris Plains, NJ (US)

(73) Assignee: Novartis AG, Basel (CH)

( * ) Notice: Subject to any disclaimer, the term of this patent is extended or adjusted under 35 U.S.C. 154(b) by 1212 days.

(21) Appl. No.: 12/295,534

(22) PCT Filed: Mar. 28, 2007

(86) PCT No.: PCT/US2007/007772
§ 371 (c)(1),
(2), (4) Date: Sep. 30, 2008

(87) PCT Pub. No.: WO2007/126957
PCT Pub. Date: Nov. 8, 2007

(65) Prior Publication Data
US 2009/0247534 A1    Oct. 1, 2009

Related U.S. Application Data

(60) Provisional application No. 60/787,859, filed on Mar. 31, 2006.

(51) Int. Cl.
A01N 43/40 (2006.01)
A61K 31/435 (2006.01)
C07D 475/00 (2006.01)

(52) U.S. Cl.
USPC ............ 514/277; 544/255; 544/256; 544/257

(58) Field of Classification Search
USPC ........... 546/257, 255, 256; 514/277; 544/255, 544/256, 257
See application file for complete search history.

(56) References Cited

U.S. PATENT DOCUMENTS

| 7,091,228 B2 | 8/2006 | Smith et al. |
| 7,132,456 B2 | 11/2006 | Gillig et al. |
| 2005/0070545 A1 | 3/2005 | Fox et al. |
| 2007/0123504 A1 | 5/2007 | Bolin et al. |
| 2009/0076275 A1 | 3/2009 | Bolin et al. |
| 2009/0093497 A1 | 4/2009 | Bolin et al. |
| 2009/0105273 A1 | 4/2009 | Bolin et al. |
| 2009/0170864 A1 | 7/2009 | Bolin et al. |

FOREIGN PATENT DOCUMENTS

| EP | 1052238 A1 | 11/2000 |
| EP | 1389616 | 2/2004 |
| WO | 00/25780 A | 5/2000 |
| WO | 02/11724 A | 2/2002 |
| WO | 02072549 | 9/2002 |
| WO | 02/088111 | 11/2002 |
| WO | 03015773 | 2/2003 |
| WO | 2004/032882 A | 4/2004 |
| WO | 2004/041810 A | 5/2004 |
| WO | 2004/047755 A | 6/2004 |
| WO | 2004047755 | 6/2004 |
| WO | 2004069158 | 8/2004 |
| WO | 2004/089286 A | 10/2004 |
| WO | 2004/100881 A | 11/2004 |
| WO | 2004100881 | 11/2004 |
| WO | 2004/110350 A | 12/2004 |
| WO | 2005/003115 | 1/2005 |
| WO | 2005007647 | 1/2005 |
| WO | 2005/012295 A | 2/2005 |
| WO | 2005/021529 | 3/2005 |
| WO | 2005035526 | 4/2005 |
| WO | 2005/061477 A | 7/2005 |
| WO | 200508371 | 9/2005 |
| WO | 2005121132 | 12/2005 |
| WO | 2006004200 | 1/2006 |
| WO | 2006/019020 A | 2/2006 |
| WO | 2006/044775 A | 4/2006 |
| WO | 2006044775 | 4/2006 |
| WO | 2006060109 | 6/2006 |
| WO | 2006082952 | 8/2006 |
| WO | 2006/113919 A | 10/2006 |
| WO | 2006113919 | 10/2006 |
| WO | 2006120125 | 11/2006 |
| WO | 2006134317 | 12/2006 |
| WO | 2007016538 | 2/2007 |
| WO | 2007022269 | 2/2007 |
| WO | 2007/038669 A | 4/2007 |
| WO | 2007060140 | 5/2007 |
| WO | 2007071966 | 6/2007 |
| WO | 2007126957 | 11/2007 |
| WO | 2007137103 | 11/2007 |
| WO | 2007137107 | 11/2007 |
| WO | 2007138304 | 12/2007 |
| WO | 2007138311 | 12/2007 |
| WO | 2007141502 | 12/2007 |
| WO | 2007141517 | 12/2007 |
| WO | 2007141538 | 12/2007 |

(Continued)

OTHER PUBLICATIONS

Vippagunta et al.*
McMahon et al.*
Pinedo et al.*
Serrano-Wu, et al, "Antisense and small-molecule modulation of diacylglycerol acyltransferase" Expert Opin. Ther. Patents (2007) 17(11), pp. 1331-1339.
King, et al, "Inhibitors of diacylglycerol acyltransferase: a review of 2008 patents" Expert Opin. Ther. Patents (2010) 20(1), pp. 19-29.

(Continued)

*Primary Examiner* — Paul V. Ward
(74) *Attorney, Agent, or Firm* — Joshua Roth

(57) ABSTRACT

The present invention provides organic compounds of the following structure;

A-L1-B-C-D-L2-E that are useful for treating or preventing conditions or disorders associated with DGAT1 activity in animals, particularly humans.

10 Claims, No Drawings

(56) References Cited

FOREIGN PATENT DOCUMENTS

| WO | 2007141545 | 12/2007 |
|---|---|---|
| WO | 2007144571 | 12/2007 |
| WO | 2008011130 | 1/2008 |
| WO | 2008011131 | 1/2008 |
| WO | 2008059026 | 5/2008 |
| WO | 2008067257 | 6/2008 |
| WO | 2008099221 | 8/2008 |
| WO | 2008129319 | 10/2008 |
| WO | 2008134690 | 11/2008 |
| WO | 2008134693 | 11/2008 |
| WO | 2008141976 | 11/2008 |
| WO | 2008148840 | 12/2008 |
| WO | 2008148849 | 12/2008 |
| WO | 2008148851 | 12/2008 |
| WO | 2008148868 | 12/2008 |
| WO | 2009011285 | 1/2009 |
| WO | 2009016462 | 2/2009 |
| WO | 2009024821 | 2/2009 |
| WO | 2009071483 | 6/2009 |
| WO | 2009081195 | 7/2009 |
| WO | 2008/067257 A | 9/2009 |
| WO | 2009119534 | 10/2009 |
| WO | 2009147170 | 12/2009 |

OTHER PUBLICATIONS

U.S. Appl. No. 12/239,029, filed Sep. 26, 2008, in the name of Novartis AG.
U.S. Appl. No. 12/446,088, filed Oct. 17, 2007, in the name of Novartis AG.
U.S. Appl. No. 12/518,551, filed Dec. 10, 2007, in the name of Novartis AG.
U.S. Appl. No. 12/502,669, filed Jul. 14, 2009, in the name of Novartis AG.
Zhao, et al, "Validation of diacyl glycerolacylkransferase l as a novel target for the treatment of obesity and dyslipidemia using a potent and selective small molecule inhibbr," J Med Chem. Feb. 14, 2008; 51(3):3803.
Birch, et al, "Discovery of a Potent, Selective, and Orally Efficacious Pyrimidinooxazinyl Bicyclooctaneacetic Acid Diacylglycerol AcyRransferasz+l Inhibitor," J. Med Chem. (2009), 52(6), 15581568.
Cheng, et al, "Acylation of Acylglycerols by Acyl Coenzyme A:Diacylglycerol Acyltransferase 1 ( DGATI ): functional importance of DGATI in the intestinal fat absorption," J. Biol. Chem. (2008), 283(44), 29802-2981 1.
Dow, et al, Discovery and Preclinical Pharmacology of PF-04620110: A Selective Inhibitor of DGAT-1 forthe Treatment of Typz+2 Diabetes, Gordon Conference on Medicinal Chemistry, Aug. 2009.
King, etal, "Diacylglycerol acyhnsferase 1 inhibition lowers serum triglycerides in the Zucker fatty rat and the hyperlipidemic hamster," J. Pharm. Exp. Ther, (2009), 330(2), 526531.
Linders, et al, "Discovery, synthesis and in vivo activity of phenylpiperazine DGAT-I inhibtors for the treatment of metabolic syndrome," (Poster from 238th Amer. Chem Soc meeting).
Yun, etal, "Discovery and optimization of oxazole based DGATI inhibitors for the treatment of obesity," (Poster at American Diabetes Association, Jun. 2009).
Fox, etal, "Discovery of pyrrolopyridazines as novel DGATI inhibitors," (Abstracts of Papen, 237th ACS National Meeting, Salt Lake City, UT, United States, Mar. 22-26, 2009).

* cited by examiner

COMPOUNDS

This application is the National Stage of Application No. PCT/US2007/007772, filed on Mar. 28, 2007, which claims benefit under 35 U.S.C. §119(e) of U.S. Provisional Application No. 60/787,859, filed Mar. 31, 2006, the contents of which are incorporated herein by reference in their entirety.

BACKGROUND OF THE INVENTION

Obesity can be viewed as an energy balance disorder, arising when energy input exceeds energy output, with most of the excess calories converted into triglycerides and stored in the adipose tissue. Medications currently approved for the treatment of obesity attempt to restore energy balance primarily by decreasing energy input by either suppressing appetite or interfering with lipid absorption in the small intestine. Because of the rapid increase in the prevalence of obesity worldwide and the lack of efficacy of current medical therapies, novel pharmacologic therapies for obesity are required.

One potential therapeutic strategy involves inhibiting triglyceride synthesis. Although triglycerides are essential for normal physiology, excess triglyceride accumulation results in obesity and, particularly when it occurs in nonadipose tissues, is associated with insulin resistance. DGAT is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1, see Cases et al, Proc. Natl. Acad. Sci. 95:13018-13023, 1998) and DGAT2 (acyl coA-diacylglycerol acyl transferase 2, see Cases et al, J. Biol. Chem. 276:38870-38876, 2001). DGAT1 and DGAT2 do not share significant protein sequence homology. Importantly, DGAT1 knockout mice are protected from high fat diet-induced weight gain and insulin resistance (Smith et al, Nature Genetics 25:87-90, 2000). The phenotype of the DGAT1 knockout mice suggest that a DGAT1 inhibitor has utility for the treatment of obesity and obesity-associated complications.

WO2006113919 discloses aryl alkyl acid derivatives having DGAT inhibitory activity.

WO2006044775 discloses biphenyl-4-yl-carbonylamino acid derivatives having DGAT inhibitory activity.

WO2006134317 discloses oxadiazole derivatives having DGAT inhibitor activity.

WO2006082952 discloses amide derivatives having DGAT inhibitor activity.

WO2006082010 discloses compounds having DGAT inhibitor activity.

WO 2006/019020 A1 and WO 2006/004200 A1 disclose urea derivatives having DGAT inhibitory activity.

WO 2005/044250 A1 disclose sulfonamide compounds having DGAT inhibitory activity.

WO 2005/013907 A2 discloses pyrrolo[1,2-b]derivatives having DGAT inhibitory activity.

WO 2005/072740 A2 discloses compounds having DGAT inhibitory activity.

JP 2005/206492 A2 discloses sulfonamide compounds having DGAT inhibitory activity.

JP 2004/067635 A2 discloses phosphonic acid diesters having DGAT inhibitory activity.

US 2004/0224997 A1 discloses aryl alkyl acid derivatives having DGAT1 inhibitory activity.

WO 2004/04775 A2 discloses fused bicyclic nitrogen-containing heterocycles having DGAT inhibitory activity.

US 2005/0101660 A1 discloses dibenzo-p-dioxane derivatives having DGAT inhibitory activity.

EP 0573696 A1 discloses heterobiaryl derivatives of the general structure $R^1NH-X_1-X_2-X_3-Y_1-Y_1-Y_3-Y_4$-E having aggregation inhibiting activity.

US 2005/0143422 A1 relates to biaryl sulfonamides and their use as metalloproteinase inhibitors.

WO 00/25780 relates to amine compounds of the general structure X—N(R)—B-D and their use as IMPDH inhibitors.

WO 01/42241 relates to substituted pyridazine compounds having cytokine inhibitory activity.

WO 02/055484 A1 relates to a compound of the general formula $R^1-X^1-Y-X^2$-A-B—$X^3$—N(—$X^4$—$R^2$)—Z—Ar, wherein A and B represent 5- or 6-membered aromatic rings. The compound can be used as a blood lipid depressant.

WO 02/085891 A1 relates to 2,6-substituted chroman derivatives which are useful in the treatment of beta-3 adrenoreceptor-mediated conditions.

WO 02/11724 A2 relates to pharmaceutical compositions comprising 2-pyridinamines which can be used for preventing ischemic cell death.

WO 03/062215 A1 relates to substituted thia-/oxa-/pyrazoles for inhibiting the activity of one or more protein kinases.

WO 2004/000788 A1 relates to ureido-substituted aniline compounds which are useful as serine protease inhibitors.

WO 2004/032882 A2 relates to oxazole derivatives which are useful in the treatment of diseases associated with inappropriate protein kinase activity.

WO 2004/041810 A1 relates to nitrogen-containing heteroaryl compounds which are useful for treatment of protein kinase mediated disorders.

WO 2004/046133 A1 relates to amino-heterocycles useful as VR-1 antagonists for treating pain.

WO 2004/089286 A2 relates to nitrogen-containing heteroaryl compounds which are useful for treating disorders associated with abnormal tyrosine kinase activity.

WO 2004/110350 A2 relates to compounds of the general structure (A)-$L_A$-(B)-$L_B$-(C)-$L_C$-(D) wherein A, B, C and D represent aryl/heteroaryl moieties. The compounds are useful for treating neurodegenerative diseases.

WO 2005/012295 A1 relates to substituted thiazole benzoisothiazoledioxo derivatives which are useful for treating diabetes.

WO 2005/016862 A1 relates to substituted arylalkanoic acid derivatives having prostaglandin production-suppressing activity.

WO 2005/085227 A1 relates to pyridine compounds which are useful as inhibitors of PKB/AKT kinase activity and in the treatment of cancer and arthritis.

WO 2005/100344 A1 relates to compounds which comprise substituted pyridazine and pyrimidine moieties. These compounds are useful for inhibiting the activity of a serine/threonine protein kinase.

WO 2005/116003 A2 relates to substituted oxazolobenzoisothiazole dioxide derivatives which are useful in the treatment of diabetes.

WO 98/46574 relates to pyridazine and phthalazine derivatives which are useful as anticonvulsants.

WO 99/24404 relates to substituted pyridine compounds which are useful as anti-inflammatory agents.

BRIEF DESCRIPTION OF THE INVENTION

The present invention provides derivatives that are useful for treating or preventing conditions or disorders associated with DGAT1 activity in animals, particularly humans.

The compound provided by the present invention has the following structure

A-L1-B-C-D-L2-E wherein
- A is a substituted or unsubstituted alkyl, cycloalkyl, aryl, or heterocyclyl group.
- L1 is selected from the group consisting of:
  - an amine group —NH—
  - a substituted amine group of the formula —N($CH_3$)—, —$CH_2$—NH— or —$CH_2$—$CH_2$—NH—,
  - an amide group —C(O)—NH—,
  - a sulphonamide group —S(O)$_2$—NH—, or
  - a urea group —NHC(O)—NH—,
- B is a substituted or unsubstituted, monocyclic, 5- or 6-membered divalent heteroaryl group,
- C-D is selected from the following cyclic structures:
  - C-D together is a substituted or unsubstituted divalent biphenyl group,
  - C is a substituted or unsubstituted divalent phenyl group and D is a single bond,
  - C is a substituted or unsubstituted divalent phenyl group, and D is a substituted or unsubstituted divalent non-aromatic monocyclic ring which is selected from a saturated or unsaturated divalent cycloalkyl group or a saturated or unsaturated divalent heterocycloalkyl group,
  - C-D together is a spiro residue, wherein
    - the first cyclic component is a benzo-fused cyclic component wherein the ring which is fused to the phenyl part is a 5- or 6-membered ring, optionally comprising one or more heteroatoms, the first cyclic component being attached to the moiety B via its phenyl part, and
    - the second cyclic component is a cycloalkyl or cycloalkylidenyl residue which is attached to L2,
- L2 is selected from the group consisting of:
  - a single bond,
  - a divalent residue having the following structure:

—[$R^1$]$_a$—[$R^2$]$_b$—[C(O)]$_c$—[N($R^3$)]$_d$—[$R^4$]$_e$—[$R^5$]$_f$— wherein
  - a is 0 or 1,
  - b is 0 or 1,
  - c is 0 or 1,
  - d is 0 or 1,
  - e is 0 or 1,
  - f is 0 or 1,
  - with the provisos that (a+b+c+d+e+f)>0, and c=1 if d=1,
  - $R^1$, $R^2$, $R^4$ and $R^5$, which can be the same or different, are a substituted or unsubstituted divalent alkyl, cycloalkyl, alkenyl, alkynyl, alkylene, aryl or heterocyclyl residue,
  - $R^3$ is H or hydrocarbyl, or $R^3$ and $R^4$ form together with the nitrogen atom to which they are attached a 5- or 6-membered heterocycloalkyl group,
  - with the proviso that $R^1$ and $R^2$ are not both alkyl if c=1 and d=e=f=0 and the carbonyl carbon atom is attached to the moiety E,
  - an alkylidenyl group which is linked to the moiety D via a double bond, and
- E is selected from the group consisting of:
  - a sulphonic acid group and derivatives thereof,
  - a carboxyl group and derivatives thereof, wherein the carboxyl carbon atom is attached to L2,
  - a phosphonic acid group and derivatives thereof,
  - an alpha-keto hydroxyalkyl group,
  - a hydroxyalkyl group wherein the carbon atom bonded to the hydroxyl group is further substituted with one or two trifluoro-methyl groups,
  - a substituted or unsubstituted five-membered heterocyclyl residue having in the ring at least two heteroatoms and at least one carbon atom, wherein
    - at least one carbon atom of the ring is bonded to two heteroatoms;
    - at least one of the heteroatoms to which the carbon atom of the ring is bonded is a member of the ring;
    - and at least one of the heteroatoms to which the carbon atom of the ring is bonded or at least one of the heteroatoms of the ring is bearing a hydrogen atom;
  - with the provisos that
    - L2 is not a single bond or a divalent alkyl group if the moiety D is a single bond,
    - L2 is not a single bond if the moiety D is an unsubstituted divalent phenyl group and E is a carboxylic acid or a derivative thereof,
    - E is not a carboxamide group if L2 comprises an amide group,
    - E is not a —COOH group if D is a single bond and L2 is a —N($CH_3$)—C(O)— group wherein the carbonyl carbon atom is attached to the moiety E,
    - L2 is not a divalent N-methyl piperidinyl group if the moiety E is a pyridinyl-1,2,4-triazolyl group
    - L2 is not —C(O)—[$R^4$]$_e$—[$R^5$]$_f$— when C is a substituted or unsubstituted divalent phenyl group and D is a single bond.

Unless otherwise indicated, the compounds provided in the formula above are meant to include all pharmaceutically acceptable salts, prodrugs, stereoisomers, crystalline forms, or polymorphs thereof.

The present invention also provides pharmaceutical compositions comprising the compound as defined above and a pharmaceutically acceptable carrier or excipient.

The present invention also provides methods for treating or preventing conditions or disorders associated with DGAT1 activity in animals, particularly humans.

Thus the present invention also provides a method for treating or preventing conditions or disorders associated with DGAT1 activity in mammals which method comprises administering to a mammal in need thereof a therapeutically effective amount of a compound of the present invention. Preferably, the disorder is selected from the following: metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris. In yet another aspect, the present invention provides methods of using a compound or composition of the invention as an anorectic.

The present invention also provides the use of a compound having the following structure

A-L1-B-C-D-L2-E wherein
A is a substituted or unsubstituted alkyl, cycloalkyl, aryl, or heterocyclyl group,
L1 is selected from the group consisting of:
an amine group —NH—
a substituted amine group of the formula —N(CH₃)—, —CH₂—NH— or —CH₂—CH₂—NH—,
an amide group —C(O)—NH—,
a sulphonamide group —S(O)₂—NH—, or
a urea —NHC(O)—NH—,
B is a substituted or unsubstituted, monocyclic, 5- or 6-membered divalent heteroaryl group,
C-D is selected from the following cyclic structures:
C-D together is a substituted or unsubstituted divalent biphenyl group,
C is a substituted or unsubstituted divalent phenyl group and D is a single bond,
C is a substituted or unsubstituted divalent phenyl group, and D is a substituted or unsubstituted divalent non-aromatic monocyclic ring which is selected from a saturated or unsaturated divalent cycloalkyl group or a saturated or unsaturated divalent heterocycloalkyl group,
C-D together is a spiro residue, wherein
the first cyclic component is a benzo-fused cyclic component wherein the ring which is fused to the phenyl part is a 5- or 6-membered ring, optionally comprising one or more heteroatoms, the first cyclic component being attached to the moiety B via its phenyl part, and
the second cyclic component is a cycloalkyl or cycloalkylidenyl residue which is attached to L2,
L2 is selected from the group consisting of:
a single bond,
a divalent residue having the following structure:

—[R¹]ₐ—[R²]ᵦ—[C(O)]ᵨ—[N(R³)]ᵨ—[R⁴]ₑ—[R⁵]ᵧ— wherein
a is 0 or 1,
b is 0 or 1,
c is 0 or 1,
d is 0 or 1,
e is 0 or 1,
f is 0 or 1,
with the provisos that (a+b+c+d+e+f)>0, and c=1 if d=1,
R¹, R², R⁴ and R⁵, which can be the same or different, are a substituted or unsubstituted divalent alkyl, cycloalkyl, alkenyl, alkynyl, alkylene, aryl or heterocyclyl residue,
R³ is H or hydrocarbyl, or R³ and R⁴ form together with the nitrogen atom to which they are attached a 5- or 6-membered heterocycloalkyl group,
an alkylidenyl group which is linked to the moiety D via a double bond, and
E is selected from the group consisting of:
a sulphonic acid group and derivatives thereof,
a carboxyl group and derivatives thereof, wherein the carboxyl carbon atom is attached to L2,
a phosphonic acid group and derivatives thereof,
an alpha-keto hydroxyalkyl group,
a hydroxyalkyl group wherein the carbon atom bonded to the hydroxyl group is further substituted with one or two trifluoro-methyl groups,
a substituted or unsubstituted five-membered heterocyclyl residue having in the ring at least two heteroatoms and at least one carbon atom, wherein
the at least one carbon atom of the ring is bonded to two heteroatoms;
at least one of the heteroatoms to which the carbon atom of the ring is bonded is a member of the ring;
and at least one of the heteroatoms to which the carbon atom of the ring is bonded or at least one of the heteroatoms of the ring is bearing a hydrogen atom;
or a prodrug or a pharmaceutically acceptable salt thereof for the manufacture of a medicament for the treatment of DGAT1 associated disorders.

The treatment of prevention of the DGAT1-related disorders or conditions listed above consists of administering to subject in need thereof a therapeutically effective amount of a compound described in this invention. The treatment may also include co-administration with additional therapeutic agents.

DETAILED DESCRIPTION OF THE INVENTION

Listed below are definitions of various terms used to describe the compounds of the present invention. These definitions apply to the terms as they are used throughout the specification unless they are otherwise limited in specific instances either individually or as part of a larger group, e.g., wherein an attachment point of a certain group is limited to a specific atom within that group.

The term "substituted or unsubstituted alkyl" refers to straight- or branched-chain hydrocarbon groups having 1-20 carbon atoms, preferably 1-10 carbon atoms, containing 0 to 3 substituents. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, alkanoyl, alkoxy, alkoxycarbonyl, alkoxycarbonyloxy, alkanoyloxy, thiol, alkylthio, alkylthiono, alkylsulfonyl, sulfamoyl, sulfonamido, carbamoyl, cyano, carboxy, acyl, aryl, alkenyl, alkynyl, aralkyl, aralkanoyl, aralkylthio, arylsulfonyl, arylthio, aroyl, aroyloxy, aryloxycarbonyl, aralkoxy, guanidino, optionally substituted amino, heterocyclyl.

The term "lower alkyl" refers to those alkyl groups as described above having 1-7, preferably 2-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 4-6 carbon atoms connected by single bonds, e.g., —(CH₂)x-, wherein x is 4-6, which may be interrupted with one or more heteroatoms selected from O, S, S(O), S(O)₂ or NR, wherein R may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from optionally substituted alkyl, cycloalkyl, aryl, heterocyclyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

The term "carboxamide" refers to —C(O)—NHR$_\alpha$, wherein R$_\alpha$ is selected from hydrogen, a C$_1$-C$_8$ alkyl group, a cycloalkyl group, a substituted or unsubstituted aryl group, a substituted or unsubstituted heterocyclyl group, and carboxamide is preferably —(O)—NH$_2$.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and (alkyl)$_2$N—, respectively.
The term "alkanoylamino" refers to alkyl-C(O)—NH—.
The term "alkylthio" refers to alkyl-S—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.
The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to H$_2$NS(O)$_2$—, alkyl-NHS(O)$_2$—, (alkyl)$_2$NS(O)$_2$—, aryl-NHS(O)$_2$, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.
The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.
The term "sulfonyl" refers to alkylsulfonyl, arylsulfonyl, heteroarylsulfonyl, aralkylsulfonyl, heteroaralkylsulfonyl and the like.
The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

The term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted alkyl, trifluoromethyl, cycloalkyl, halo, hydroxy, alkoxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.

The term "monocyclic aryl" refers to optionally substituted phenyl as described under aryl.

The term "aralkyl" refers to an aryl group bonded directly through an alkyl group, such as benzyl.

The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.

The term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyridyl N-oxide, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents. Exemplary substituents include, but are not limited to, the following:

(a) optionally substituted alkyl;
(b) hydroxyl (or protected hydroxyl);
(c) halo;
(d) oxo, i.e., =O;
(e) optionally substituted amino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl;
(o) alkanoyloxy;
(p) aroyloxy;
(q) arylthio;
(r) aryloxy;
(s) alkylthio;
(t) formyl;
(u) carbamoyl;
(v) aralkyl; or
(w) aryl optionally substituted with alkyl, cycloalkyl, alkoxy, hydroxyl, amino, acylamino, alkylamino, dialkylamino or halo.

The term "heterocyclooxy" denotes a heterocyclic group bonded through an oxygen bridge.

The terms "saturated or unsaturated heterocycloalkyl" or "heterocycloalkyl" refers to nonaromatic heterocyclic or heterocyclyl groups as described above.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyridyl N-oxide, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-S(O)$_2$—.

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

The term "divalent" refers to a residue linked to at least two residues and optionally having further substituents. As an example, within the context of the present invention the expression "substituted or unsubstituted divalent phenyl residue" is considered to be equivalent to the expression "substituted or unsubstituted phenylene residue".

The present invention provides a compound having the following structure

A-L1-B-C-D-L2-E and pharmaceutically acceptable salts, and prodrugs thereof, wherein A is a substituted or unsubstituted alkyl, cycloalkyl, aryl, or heterocyclyl group,
L1 is selected from the group consisting of:
  an amine group —NH—
  a substituted amine group of the formula —N(CH$_3$)—, —CH$_2$—NH— or —CH$_2$—CH$_2$—NH—,
  an amide group —C(O)—NH—,
  a sulphonamide group —S(O)$_2$—NH—, or
  a urea group —NHC(O)—NH—,
B is a substituted or unsubstituted, monocyclic, 5- or 6-membered divalent heteroaryl group,
C-D is selected from the following cyclic structures:
  C-D together is a substituted or unsubstituted divalent biphenyl group,
  C is a substituted or unsubstituted divalent phenyl group and D is a single bond,
  C is a substituted or unsubstituted divalent phenyl group, and D is a substituted or unsubstituted divalent non-aromatic monocyclic ring which is selected from a saturated or unsaturated divalent cycloalkyl group or a saturated or unsaturated divalent heterocycloalkyl group,
  C-D together is a spiro residue, wherein
    the first cyclic component is a benzo-fused cyclic component wherein the ring which is fused to the phenyl part is a 5- or 6-membered ring, optionally comprising one or more heteroatoms, the first cyclic component being attached to the moiety B via its phenyl part, and
    the second cyclic component is a cycloalkyl or cycloalkylidenyl residue which is attached to L2,
L2 is selected from the group consisting of:
  a single bond,
  a divalent residue having the following structure:

—[R$^1$]$_a$—[R$^2$]$_b$—[C(O)]$_c$—[N(R$^3$)]$_d$—[R$^4$]$_e$—[R$^5$]$_f$— wherein
  a is 0 or 1,
  b is 0 or 1,
  c is 0 or 1,
  d is 0 or 1,
  e is 0 or 1,
  f is 0 or 1,
  with the provisos that (a+b+c+d+e+f)>0, and c=1 if d=1,
  R$^1$, R$^2$, R$^4$ and R$^5$, which can be the same or different, are a substituted or unsubstituted divalent alkyl, cycloalkyl, alkenyl, alkynyl, alkylene, aryl or heterocyclyl residue,
  R$^3$ is H or hydrocarbyl, or R$^3$ and R$^4$ form together with the nitrogen atom to which they are attached a 5- or 6-membered heterocycloalkyl group,
  with the proviso that R$^1$ and R$^2$ are not both alkyl if c=1 and d=e=f=0 and the carbonyl carbon atom is attached to the moiety E,
  an alkylidenyl group which is linked to the moiety D via a double bond, and
E is selected from the group consisting of:
  a sulphonic acid group and derivatives thereof,
  a carboxyl group and derivatives thereof, wherein the carboxyl carbon atom is attached to L2,
  a phosphonic acid group and derivatives thereof,
  an alpha-keto hydroxyalkyl group,
  a hydroxyalkyl group wherein the carbon atom bonded to the hydroxyl group is further substituted with one or two trifluoro-methyl groups, a substituted or unsubstituted five-membered heterocyclyl residue having in the ring at least two heteroatoms and at least one carbon atom, wherein
the at least one carbon atom of the ring is bonded to two heteroatoms;
at least one of the heteroatoms to which the carbon atom of the ring is bonded is a member of the ring;
and at least one of the heteroatoms to which the carbon atom of the ring is bonded or at least one of the heteroatoms of the ring is bearing a hydrogen atom;
with the provisos that
L2 is not a single bond or a divalent alkyl group if the moiety D is a single bond,
L2 is not a single bond if the moiety D is an unsubstituted divalent phenyl group and E is a carboxylic acid or a derivative thereof,
E is not a carboxamide group if L2 comprises an amide group,
E is not a —COOH group if D is a single bond and L2 is a —N(CH$_3$)—C(O)— group wherein the carbonyl carbon atom is attached to the moiety E,
L2 is not a divalent N-methyl piperidinyl group if the moiety E is a pyridinyl-1,2,4-triazolyl group.

The present invention provides a compound having the following structure

A-L1-B-C-D-L2-E and pharmaceutically acceptable salts, and prodrugs thereof, wherein
A is a substituted or unsubstituted alkyl, cycloalkyl, aryl, or heterocyclyl group,
L1 is selected from the group consisting of:
an amine group —NH—
a substituted amine group of the formula —N(CH$_3$)—, —CH$_2$—NH— or —CH$_2$—CH$_2$—NH—,
an amide group —C(O)—NH—,
a sulphonamide group —S(O)$_2$—NH—, or
a urea group —NHC(O)—NH—,
B is a substituted or unsubstituted, monocyclic, 5- or 6-membered divalent heteroaryl group,
C-D is selected from the following cyclic structures:
C-D together is a substituted or unsubstituted divalent biphenyl group,
C is a substituted or unsubstituted divalent phenyl group and D is a single bond,
C is a substituted or unsubstituted divalent phenyl group, and D is a substituted or unsubstituted divalent non-aromatic monocyclic ring which is selected from a saturated or unsaturated divalent cycloalkyl group or a saturated or unsaturated divalent heterocycloalkyl group,
C-D together is a spiro residue, wherein
the first cyclic component is a benzo-fused cyclic component wherein the ring which is fused to the phenyl part is a 5- or 6-membered ring, optionally comprising one or more heteroatoms, the first cyclic component being attached to the moiety B via its phenyl part, and
the second cyclic component is a cycloalkyl or cycloalkylidenyl residue which is attached to L2,
L2 is selected from the group consisting of:
a single bond,
a divalent residue having the following structure:

—[R$^1$]$_a$—[R$^2$]$_b$—[C(O)]$_c$—[N(R$^3$)]$_d$—[R$^4$]$_e$—[R$^5$]$_f$— wherein
a is 0 or 1,
b is 0 or 1,
c is 0 or 1,
d is 0 or 1,
e is 0 or 1,
f is 0 or 1,
with the provisos that (a+b+c+d+e+f)>0, and c=1 if d=1,
R$^1$, R$^2$, R$^4$ and R$^5$, which can be the same or different, are a substituted or unsubstituted divalent alkyl, cycloalkyl, alkenyl, alkynyl, alkylene, aryl or heterocyclyl residue,
R$^3$ is H or hydrocarbyl, or R$^3$ and R$^4$ form together with the nitrogen atom to which they are attached a 5- or 6-membered heterocycloalkyl group,
with the proviso that R$^1$ and R$^2$ are not both alkyl if c=1 and d=e=f=0 and the carbonyl carbon atom is attached to the moiety E,
an alkylidenyl group which is linked to the moiety D via a double bond, and
E is selected from the group consisting of:
a sulphonic acid group and derivatives thereof,
a carboxyl group and derivatives thereof, wherein the carboxyl carbon atom is attached to L2,
a phosphonic acid group and derivatives thereof,
an alpha-keto hydroxyalkyl group,
a hydroxyalkyl group wherein the carbon atom bonded to the hydroxyl group is further substituted with one or two trifluoro-methyl groups,
a substituted or unsubstituted five-membered heterocyclyl residue having in the ring at least two heteroatoms and at least one carbon atom, wherein
the at least one carbon atom of the ring is bonded to two heteroatoms;
at least one of the heteroatoms to which the carbon atom of the ring is bonded is a member of the ring;
and at least one of the heteroatoms to which the carbon atom of the ring is bonded or at least one of the heteroatoms of the ring is bearing a hydrogen atom;
with the provisos that
L2 is not a single bond or a divalent alkyl group if the moiety D is a single bond,
L2 is not a single bond if the moiety D is an unsubstituted divalent phenyl group and E is a carboxylic acid or a derivative thereof,
E is not a carboxamide group if L2 comprises an amide group,
E is not a —COOH group if D is a single bond and L2 is a —N(CH$_3$)—C(O)— group wherein the carbonyl carbon atom is attached to the moiety E,
L2 is not a divalent N-methyl piperidinyl group if the moiety E is a pyridinyl-1,2,4-triazolyl group,
L2 is not —C(O)—[R$^4$]$_e$—[R$^5$]$_f$— when C is a substituted or unsubstituted divalent phenyl group and D is a single bond.

Unless otherwise indicated, the compounds provided in the formula above are meant to include all pharmaceutically acceptable salts, prodrugs, stereoisomers, crystalline forms, or polymorphs thereof.

In a preferred embodiment, the moiety A is selected from the group consisting of a substituted or unsubstituted phenyl group and a substituted or unsubstituted monocyclic or bicyclic heterocyclyl group. Preferred substituents are halogen, alkyl, cycloalkyl, cyano, trifluoromethyl, alkoxy, hydroxyl, optionally substituted amino, acyl, alkanoyloxy, alkanoylamino, aryloxy, alkylthio, arylthio, nitro, carboxy, alkoxycarbonyl, carbamoyl, alkylthiono, sulfonyl, sulfonamido, and heterocyclyl. More preferably, the substituents of moiety A are selected from halogen, alkyl, cycloalkyl, cyano, trifluoromethyl, alkoxy, alkanoylamino, hydroxyl, optionally substituted amino. Or preferably, the substituents of moiety A are selected from halogen, lower alkyl, C3 to C6 cycloalkyl, cyano, trifluoromethyl, lower alkoxy, lower alkanoylamino, hydroxyl, optionally substituted amino.

When the moiety A is a monocyclic heterocyclyl, it is in a first preferred embodiment heteroaryl.

When the moiety A is a monocyclic heteroaryl, it preferably is a pyridine, oxadiazole, pyridine N-oxide, pyrazole, isoxazole, pyridazine, pyrimidine or pyrazine residue.

When the moiety A is a bicyclic heterocyclyl, it preferably is a benzimidazole, benzoxazole, benzothiazole, oxazolopyridine, thiazolopyridine, imidazolopyridine, indole, quinoline, isoquinoline, benzofuran, benzothiophene, indazole, cinnoline, quinazoline, quinoxaline or phthalazine residue. More preferably, the bicyclic heterocyclyl group is selected from a benzimidazole, benzoxazole, benzothiazole, oxazolopyridine, thiazolopyridine or imidazolopyridine group.

When the moiety A is a cycloalkyl group, it is preferably a cyclopropyl, cyclobutyl, cyclopentyl, or cyclohexyl group.

In a preferred embodiment, the linker moiety L1 is attached to the ring of the bicyclic heteroaryl group containing the heteroatom.

In a preferred embodiment L1 group is an amine group —NH—.

In another preferred embodiment L1 group is an amide group —C(O)NH— or —NHC(O)—.

The amide group representing L1 can have the following orientations:

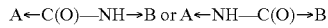

However, in a preferred embodiment the carbonyl carbon atom is attached to the moiety A.

The substituted amine group —CH$_2$—NH— or —CH$_2$—CH$_2$—NH— representing L1 can be attached to the moiety B either via the nitrogen atom or via the carbon atom. However, in a preferred embodiment the carbon atom is attached to the moiety A.

The sulphonamide group representing L1 can have the following orientations:

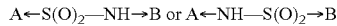

However, in a preferred embodiment the sulphur atom is attached to the moiety A.

According to the present invention, the moiety B is a substituted or unsubstituted, monocyclic, 5- or 6-membered heteroaryl group. As explained above, the term "divalent" refers to a residue being attached to at least two further residues. Within the context of the present invention, the expression "unsubstituted or substituted monocyclic 5- or 6-membered heteroarenediyl group" is considered to be equivalent to the expression used above.

Besides the moieties L1 and C-D to which it is attached, the moiety B can have from 1 to 3 additional substituents. Preferred substituents comprise halogen, alkyl, cycloalkyl, cyano, trifluoromethyl, alkoxy, hydroxyl, and optionally substituted amino.

Preferably, the moiety B is selected from the group consisting of a 6-membered substituted or unsubstituted divalent heteroaryl group wherein the heteroatom is nitrogen, or a 5-membered substituted or unsubstituted divalent heteroaryl group wherein the heteroatom is nitrogen, oxygen and/or sulphur.

In a preferred embodiment, the moiety B is selected from a pyridine, pyridine N-oxide, pyridazine, pyrimidine, pyrazine, oxazole, or thiazole group.

According to the present invention, the moiety C within the structural element C-D is a divalent phenyl group. As discussed above, the expressions "phenylene" or "benzenediyl" are considered to be equivalent.

The divalent phenyl residue can be unsubstituted or can have from 1 to 4 substituents. Preferred substituents comprise halogen, alkyl, cycloalkyl, cyano, trifluoromethyl, alkoxy, hydroxyl, and amino which is optionally substituted.

When the structural element C-D is a divalent biphenyl group, the phenyl moiety D can be substituted or unsubstituted. Preferred substituents are those listed above for moiety C.

When the moiety D is a substituted or unsubstituted divalent non-aromatic monocyclic ring which is selected from a saturated or unsaturated divalent cycloalkyl group or a saturated or unsaturated divalent heterocycloalkyl group, it is preferably selected from a substituted or unsubstituted divalent cyclohexyl group or a non-aromatic 6-membered substituted or unsubstituted divalent heterocycloalkyl group wherein the heteroatom is nitrogen.

In a preferred embodiment, the 6-membered heterocycloalkyl group is selected from a piperidine group or a tetrahydro-pyridine group.

Preferred substituents of the divalent non-aromatic monocyclic ring are those listed above for the moiety C.

When the moiety D is a substituted or unsubstituted divalent non-aromatic monocyclic ring, especially a cyclohexyl, the moiety A-L1-B-C— and the moiety -L2-E are in a trans configuration e.g.

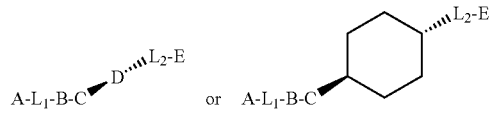

When the structural element C-D is a spiro residue, the first cyclic component of the spiro residue is preferably selected from an indanyl group, a benzo-tetrahydrofuranyl group, a benzo-pyrrolidinyl group, a benzo-pyrrolidinonyl group, or a benzo-piperidinyl group.

The second cyclic component of the spiro residue is preferably selected from a cyclohexyl group or a cyclohexylidenyl group.

Preferred spiro residues can be those given below:

I-a:

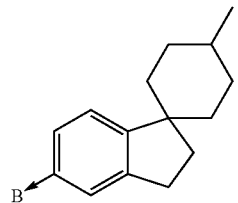

I-b:
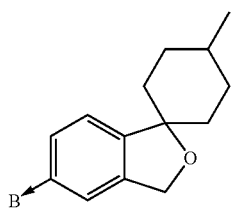

I-c:
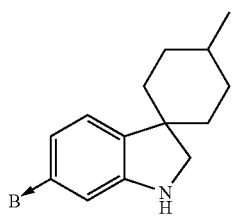

I-d:
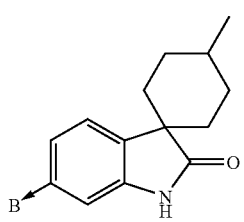

I-e:
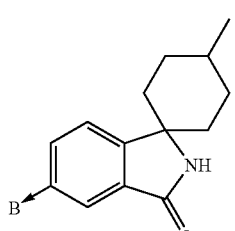

I-f:
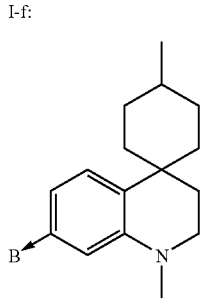

In other preferred embodiments, the second cyclic component can be a cyclohexylidenyl group as shown below:

II-a:
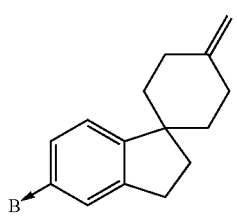

II-b:
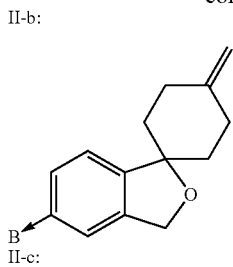

II-c:
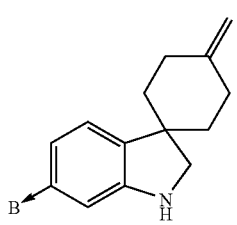

II-d:
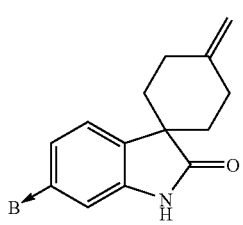

II-e:
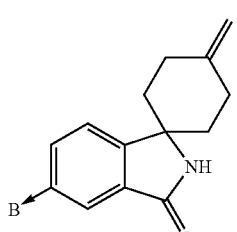

II-f:
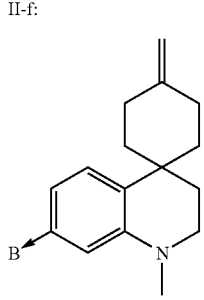

When the second cyclic component of the spiro residue is a cycloalkylidenyl group, the moiety L2 preferably is =CH—.

When the moiety L2 is a divalent residue —[$R^1$]$_a$—[$R^2$]$_b$—[C(O)]$_c$—[N($R^3$)]$_d$—[$R^4$]$_e$—[$R^5$]$_f$—, it is preferably selected from the group consisting of:

- a divalent alkyl group having from 1 to 4 carbon atoms,
- a divalent alkenyl group having from 2 to 3 carbon atoms,
- a —C(O)— group,
- a —C(O)—[$R^4$]$_e$—$R^5$— group wherein
  e is 0 and $R^5$ is selected from the group consisting of a divalent substituted or unsubstituted $C_1$-$C_4$ alkyl group, $C_4$-$C_8$ cycloalkyl group, phenyl group or 5- or 6-membered heterocyclyl group, or e is 1, $R^4$ is a divalent substituted or unsubstituted $C_1$-$C_4$ alkyl group, and $R^5$ is a divalent substituted or unsubstituted $C_4$-$C_8$ cycloalkyl group, phenyl group or 5- or 6-membered heterocyclyl group, a —$R^1$-$R^2$— group, wherein $R^1$ is a divalent substituted or unsubstituted $C_1$-$C_4$ alkyl group and $R^2$ is a divalent substituted or unsubstituted $C_4$-$C_8$ cycloalkyl group, phenyl group or 5- or 6-membered heterocyclyl group, a —C(O)—NH— group, a —$(CH_2)_{1-3}$—C(O)—NH—$(CH_2)_{1-3}$— group a —(O)—NH—$R^4$— group, wherein $R^4$ is selected from a divalent substituted or unsubstituted $C_{1-7}$ alkyl group, cyclohexyl group or cyclopentyl group, a —C(O)—N($R^3$)—$R^4$— group, wherein $R^3$ and $R^4$ and the N-atom together form a pyrrolidine ring or a piperidine ring.

Preferred substituents for residues $R^1$, $R^2$, $R^4$ and $R^5$ include hydroxyl, alkoxy, keto, amino which is optionally substituted, and alkyl.

Preferably, the divalent residue —$[R^1]_a$—$[R^2]_b$—$[C(O)]_c$—$[N(R^3)]_d$—$[R^4]_e$—$[R^5]_f$— has the following orientation:

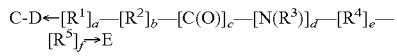

When E is a carboxyl group or a derivative thereof, it is preferably selected from a —COOH group, a carboxylic ester group, or a carboxamide group.

Chemical formulas of preferred carboxyl group derivatives are given below:

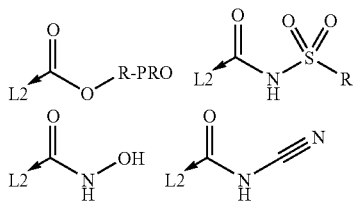

For the carboxyl group derivatives above, "R-PRO" refers to the common ester derivatives that can serve as a prodrug.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

When E is a sulphonic acid group or a derivative thereof, it is preferably selected from a —$S(O)_2$—OH group, or a —$S(O)_2$—$NHR^6$ group, wherein $R^6$ is selected from hydrogen, a $C_1$-$C_8$ alkyl group, a cycloalkyl group, a substituted or unsubstituted aryl group, a substituted or unsubstituted heterocyclyl group, or a carboxylic acid ester group.

The sulphonic acid group or derivative thereof can be attached to the moiety L2 via its sulphur atom or via its nitrogen atom. Preferably, it is attached to the moiety L2 via its sulphur atom.

Chemical formulas of preferred embodiments are also shown below:

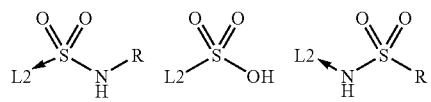

wherein R has the same meaning as $R^6$ defined above.

When E is an alpha-keto hydroxyalkyl group, the carbon atom bearing the hydroxyl group can be further substituted. Preferred substitutents are alkyl, cycloalkyl, aryl or heteroaryl. In a preferred embodiment, the hydroxyl-bearing carbon atom is having two substituents which are joined together to form a substituted or unsubstituted cycloalkyl, aryl or heteroaryl group.

A chemical formula of a preferred embodiment is also shown below:

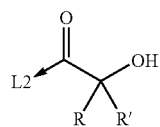

wherein R and R' are independently hydrogen, alkyl, cycloalkyl, aryl or heteroaryl, or both residues R and R' are joined together to form a substituted or unsubstituted cycloalkyl or heterocycloalkyl group.

When E is a hydroxyalkyl group wherein the carbon atom bonded to the hydroxyl group is further substituted with one or two trifluoromethyl groups, preferred embodiments can have a structure as shown below:

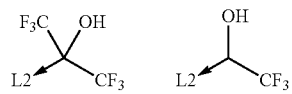

When E is a substituted or unsubstituted 5-membered heterocyclyl residue, it is preferably selected from the group consisting of:
a tetrazole residue,
a triazole residue,
an oxadiazole residue,
a thiadiazole residue,
a diazole residue,
an oxazole residue,
a thiazole residue,
an oxathiadiazole residue,
the heterocyclyl residue optionally having one or more substituents selected from an oxo group, a hydroxyl group and/or a thiol group.

Chemical formulas of preferred heterocyclyl residues representing moiety E are also shown below:

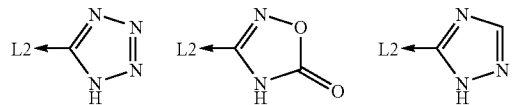

-continued

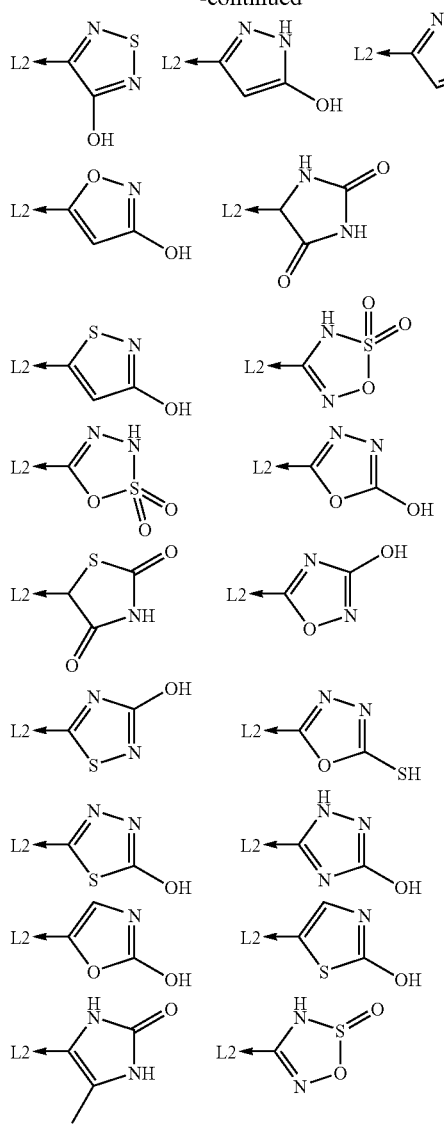

In a further embodiment, the present invention concerns compounds of formula;

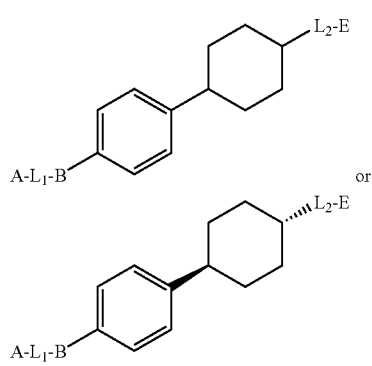

respectively designated as the SIGMA group and the SIGMA' group, wherein the moieties A, L1, B and -L2-E are the same as the preferred moieties described herein above for the structure A-L1-B-C-L2-E.

Preferred are the compounds in the SIGMA and SIGMA' groups wherein;

the moiety B is selected from the group consisting of: a substituted or unsubstituted pyridine group, a substituted or unsubstituted pyridazine group, a substituted or unsubstituted pyrimidine group, a substituted or unsubstituted pyrazine group, a substituted or unsubstituted oxazole group, the L1 group is selected from the group consisting of: an amine group —NH—, an amide group —C(O)NH— or —NHC(O)— group, the moiety A is a substituted or unsubstituted cycloalkyl, a substituted or unsubstituted aryl, or a substituted or unsubstituted heterocycyl group, and is preferably selected from the group consisting of a substituted or unsubstituted phenyl, a substituted or unsubstituted pyridine, a substituted or unsubstituted cyclohexyl, a substituted or unsubstituted isoxazole, a substituted or unsubstituted oxadiazole, or a substituted or unsubstituted pyrazole, the moiety -L2- i.e. the divalent residue —[R$^1$]$_a$—[R$^2$]$_b$—[C(O)]$_c$—[N(R$^3$)]$_d$—[R$^4$]$_e$—[R$^5$]$_f$— is selected from the group consisting of:

a divalent alkyl group having from 1 to 4 carbon atoms a divalent alkenyl group having from 2 to 3 carbon atoms a —C(O)— group a —C(O)—[R$^4$]$_e$-R$^5$— group wherein
  e is 0 and R$^5$ is selected from the group consisting of a divalent substituted or unsubstituted C$_1$-C$_4$ alkyl group, C$_4$-C$_8$ cycloalkyl group, phenyl group or 5- or 6-membered heterocyclyl group, or
  e is 1, R$^4$ is a divalent substituted or unsubstituted C$_1$-C$_4$ alkyl group, and R$^5$ is a divalent substituted or unsubstituted C$_4$-C$_8$ cycloalkyl cycloalkyl group, phenyl group or 5- or 6-membered heterocyclyl group, a —R$^1$-R$^2$— group, wherein R$^1$ is a divalent substituted or unsubstituted C$_1$-C$_4$ alkyl group and R$^2$ is a divalent substituted or unsubstituted C$_4$-C$_8$ cycloalkyl group, phenyl group or 5 or 6-membered heterocyclyl group, a —C(O)—NH— group, a —(CH$_2$)$_{1-3}$—C(O)—NH—(CH$_2$)$_{1-3}$— group, a —C(O)—NH—R$^4$— group, wherein R$^4$ is selected from a divalent substituted or unsubstituted C$_{1-7}$ alkyl group, cyclohexyl group or cyclopentyl group, a —C(O)—N(R$^3$)—R$^4$— group, wherein R$^3$ and R$^4$ and the N-atom together form a pyrrolidine ring or a piperidine ring, the moiety E is selected from the group consisting of:
  COOH,
  a carbocylic ester group,
  a carboxamide group,
  a —S(O)$_2$—OH group,
  a —S(O)$_2$—NHR$^6$ group, wherein R$^6$ is selected from hydrogen, a C$_1$-C$_8$ alkyl group, a cycloalkyl group, a substituted or unsubstituted aryl group, a substituted or unsubstituted heterocyclyl group, or a carboxylic acid ester group, or pharmaceutically acceptable salts, prodrugs, stereoisomers, crystalline forms, or polymorphs thereof.

The invention covers the compounds in the SIGMA and SIGMA' groups wherein the moiety -L2-E is equivalent to the below described groups E'.

Preferred are the compounds of formula;

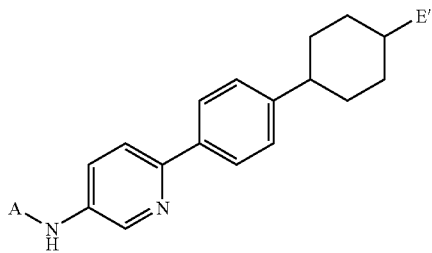
(I)

or

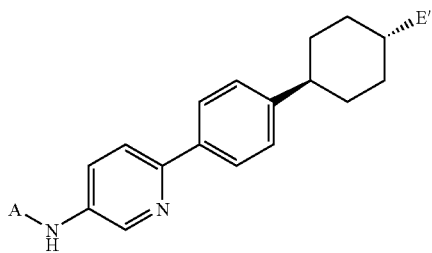
(II)

respectively designated as the ALPHA group and the ALPHA' group, or the compounds of formula

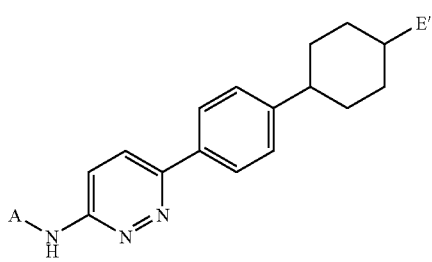
(III)

or

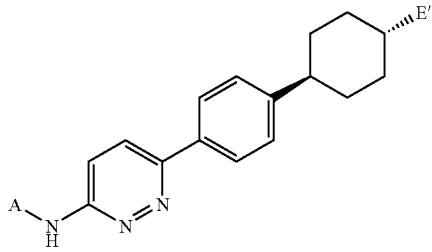
(IV)

respectively designated as the BETA group and the BETA' group, or the compounds of formula

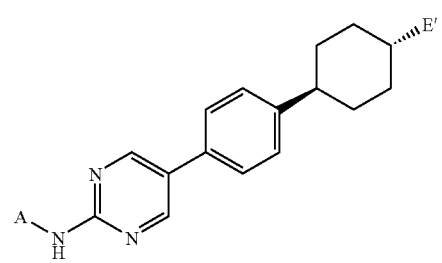
(V)

or

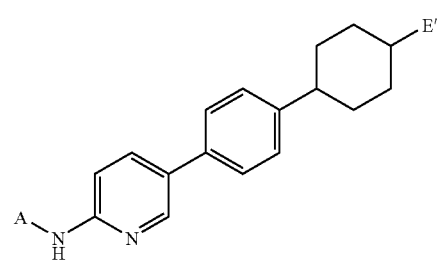
(VI)

respectively designated as the GAMMA group and the GAMMA' group, or the compounds of formula

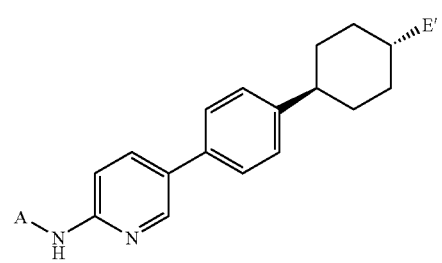
(VII)

or

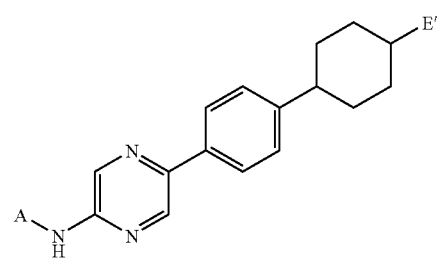
(VIII)

respectively designated as the DELTA group and the DELTA' group,
or the compounds of formula

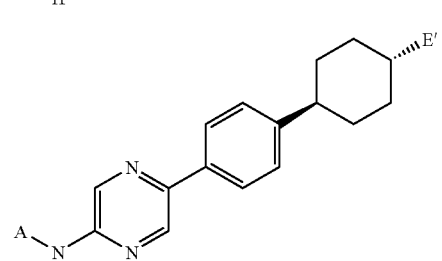
(IX)

or (X)

respectively designated as the EPSILON group and the EPSILON' group, or the compounds of formula

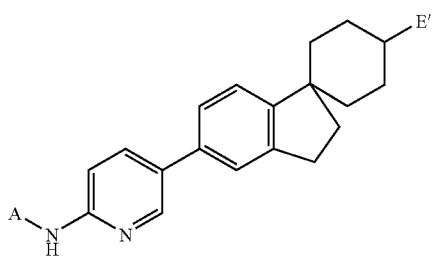

(XI)

or

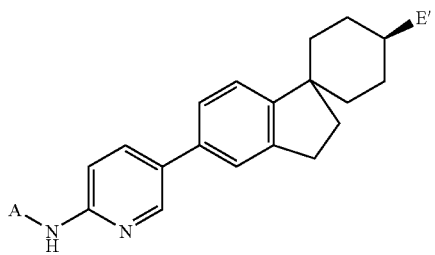

(XII)

respectively designated as the THETA group and the THETA' group, or the compounds of formula

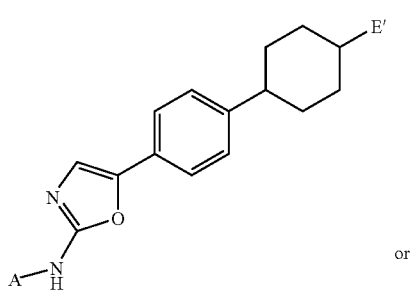

(XIII)

or

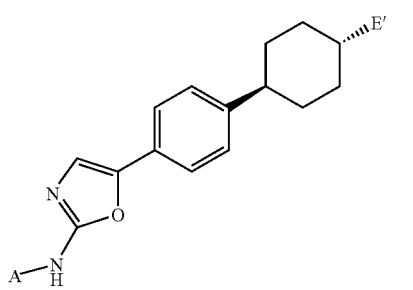

(XIV)

respectively designated as the KAPPA group and the KAPPA' group, or the compounds of formula

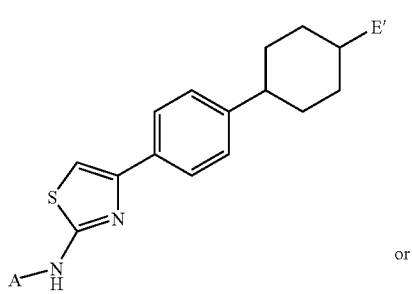

(XV)

or

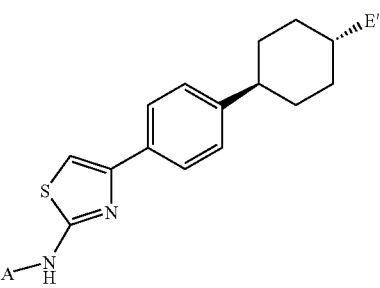

(XVI)

respectively designated as the ZETA group and the ZETA' group,
wherein;
A is a substituted or unsubstituted cycloalkyl, a substituted or unsubstituted aryl, or a substituted or unsubstituted heterocyclyl group,
E' is -L2-E,
or pharmaceutically acceptable salts, prodrugs, stereoisomers, crystalline forms, or polymorphs thereof.

Preferred are the compounds in the ALPHA, ALPHA', BETA, BETA', GAMMA, GAMMA', DELTA, DELTA', EPSILON, EPSILON', THETA, THETA', KAPPA, KAPPA', ZETA, ZETA' groups wherein the moieties A and moieties -L2-E are the same as the preferred moieties described herein above for the structure A-L1-B-C-L2-E.

Preferred are the compounds in the ALPHA, ALPHA', BETA, BETA', GAMMA, GAMMA', DELTA, DELTA', EPSILON, EPSILON', THETA, THETA', KAPPA, KAPPA', ZETA, ZETA' groups wherein;
the moiety -L2- i.e. the divalent residue $—[R^1]_a—[R^2]_b—[C(O)]_c—[N(R^3)]_d—[R^4]_e—[R^5]_f—$ is selected from the group consisting of:
a divalent-alkyl group having from 1 to 4 carbon atoms
a divalent alkenyl group having from 2 to 3 carbon atoms
a —C(O)— group
a $—C(O)—[R^4]_e-R^5—$ group wherein
  e is 0 and $R^5$ is selected from the group consisting of a divalent substituted or unsubstituted $C_1$-$C_4$ alkyl group, $C_4$-$C_8$ cycloalkyl group, phenyl group or 5- or 6-membered heterocyclyl group, or
  e is 1, $R^4$ is a divalent substituted or unsubstituted $C_1$-$C_4$ alkyl group, and $R^5$ is a divalent substituted or unsubstituted $C_4$-$C_8$ cycloalkyl cycloalkyl group, phenyl group or 5- or 6-membered heterocyclyl group,
a $—R^1$-$R^2—$ group, wherein $R^1$ is a divalent substituted or unsubstituted $C_1$-$C_4$ alkyl group and $R^2$ is a divalent substituted or unsubstituted $C_4$-$C_8$ cycloalkyl group, phenyl group or 5- or 6-membered heterocyclyl group,
a —C(O)—NH— group,
a —(CH$_2$)$_{1-3}$—C(O)—NH—(CH$_2$)$_{1-3}$— group,
a —C(O)—NH—$R^4$— group, wherein $R^4$ is selected from a divalent substituted or unsubstituted $C_{1-7}$ alkyl group, cyclohexyl group or cyclopentyl group,
a —C(O)—N($R^3$)—$R^4$— group, wherein $R^3$ and $R^4$ and the N-atom together form a pyrrolidine ring or a piperidine ring,
the moiety E is selected from the group consisting of:
COOH,
a carbocylic ester group,
a carboxamide group,
a —S(O)$_2$—OH group, a —(O)$_2$—NHR$^6$ group, wherein R$^6$ is selected from hydrogen, a C$_1$-C$_8$ alkyl group, a cycloalkyl group, a substituted or unsubstituted aryl group, a substituted or unsubstituted heterocyclyl group, or a carboxylic acid ester group, the moiety A is a substituted or unsubstituted cycloalkyl, a substituted or unsubstituted aryl, or a substituted or unsubstituted heterocyclyl group, and is preferably selected from the group consisting of a substituted or unsubstituted phenyl, a substituted or unsubstituted pyridine, a substituted or unsubstituted cyclohexyl, a substituted or unsubstituted isoxazole, a substituted or unsubstituted oxadiazole, or a substituted or unsubstituted pyrazole, or pharmaceutically acceptable salts, prodrugs, stereoisomers, crystalline forms, or polymorphs thereof.

Preferred are the compounds in the ALPHA, ALPHA', BETA, BETA', GAMMA, GAMMA', DELTA, DELTA', EPSILON, EPSILON', THETA, THETA', KAPPA, KAPPA', ZETA, ZETA', SIGMA and SIGMA' groups wherein;

E' is —C(O)OH, —CH$_2$—C(O)OH, —C$_2$H$_4$—C(O)OH— CH$_2$-heterocyclyl.

Preferred are the compounds in the ALPHA, ALPHA', BETA, BETA', GAMMA, GAMMA', DELTA, DELTA', EPSILON, EPSILON', THETA, THETA', KAPPA, KAPPA', ZETA, ZETA', SIGMA and SIGMA' groups wherein;

A is selected from a substituted or unsubstituted phenyl, a substituted or unsubstituted pyridine, a substituted or unsubstituted cyclohexyl, a substituted or unsubstituted isoxazol, or a substituted or unsubstituted pyrazol.

Preferred are the compounds in the ALPHA, ALPHA', BETA, BETA', GAMMA, GAMMA', DELTA, DELTA', EPSILON, EPSILON', THETA, THETA', KAPPA, KAPPA', ZETA, ZETA', SIGMA and SIGMA' groups wherein;

A is selected from a substituted or unsubstituted phenyl, a substituted or unsubstituted pyridine, a substituted or unsubstituted cyclohexyl, a substituted or unsubstituted isoxazole, a substituted or unsubstituted oxadiazole, or a substituted or unsubstituted pyrazole, and E' is —C(O)OH, —CH$_2$—C(O)OH, —CH$_2$-heterocyclyl.

When E' is —CH$_2$-heterocyclyl, it is preferably selected from

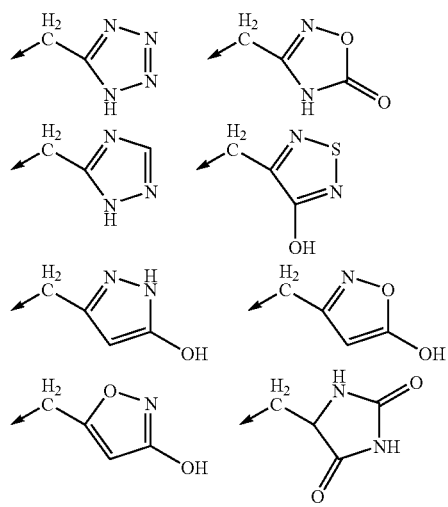

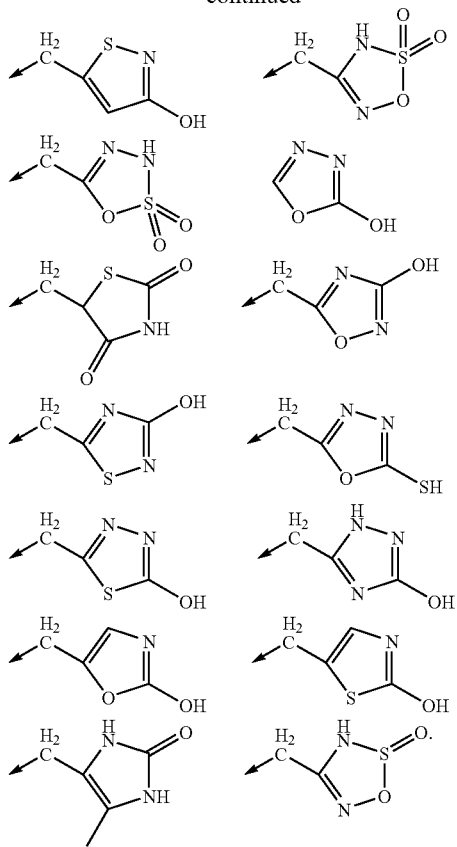

The present invention also covers pharmaceutically acceptable salts, prodrugs, stereoisomers, crystalline forms, or polymorphs of the hereinabove described compounds in the ALPHA, ALPHA', BETA, BETA', GAMMA, GAMMA', DELTA, DELTA', EPSILON, EPSILON', THETA, THETA', KAPPA, KAPPA', ZETA, ZETA', SIGMA and SIGMA' groups.

The present invention also provides a pharmaceutical composition comprising the compound as defined above and a pharmaceutically acceptable carrier or excipient.

According to a further aspect, the present invention provides use of a compound having the following chemical structure

A-L1-B-C-D-L2-E wherein
A is a substituted or unsubstituted alkyl, cycloalkyl, aryl, or heterocyclyl group,
L1 is selected from the group consisting of:
an amine group —NH—
a substituted amine group of the formula —N(CH$_3$)—, —CH$_2$—NH— or —CH$_2$—CH$_2$—NH—,
an amide group —C(O)—NH—,
a sulphonamide group —S(O)$_2$—NH—, or
a urea group —NHC(O)—NH—,
B is a substituted or unsubstituted, monocyclic, 5- or 6-membered divalent heteroaryl group,
C-D is selected from the following cyclic structures:
C-D together is a substituted or unsubstituted divalent biphenyl group,
C is a substituted or unsubstituted divalent phenyl group and D is a single bond, C is a substituted or unsubstituted divalent phenyl group, and D is a substituted or unsubstituted divalent non-aromatic monocyclic ring which is selected from a saturated or unsaturated divalent cycloalkyl group or a saturated or unsaturated divalent heterocycloalkyl group, C-D together is a spiro residue, wherein
the first cyclic component is a benzo-fused cyclic component wherein the ring which is fused to the phenyl part is a 5- or 6-membered ring, optionally comprising one or more heteroatoms, the first cyclic component being attached to the moiety B via its phenyl part, and
the second cyclic component is a cycloalkyl or cycloalkylidenyl residue which is attached to L2, L2 is selected from the group consisting of:
a single bond,
a divalent residue having the following structure:

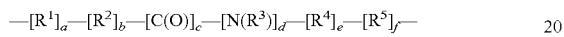

wherein
a is 0 or 1,
b is 0 or 1,
c is 0 or 1,
d is 0 or 1,
e is 0 or 1,
f is 0 or 1,
with the proviso that (a+b+c+d+e+f)>0, and c=1 if d=1,
$R^1$, $R^2$, $R^4$ and $R^5$, which can be the same or different, are a substituted or unsubstituted divalent alkyl, cycloalkyl, alkenyl, alkynyl, alkylene, aryl or heterocyclyl residue,
$R^3$ is H or hydrocarbyl, or $R^3$ and $R^4$ form together with the nitrogen atom to which they are attached a 5- or 6-membered heterocycloalkyl group,
an alkylidenyl group which is linked to the moiety D via a double bond, and E is selected from the group consisting of:
a sulphonic acid group and derivatives thereof,
a carboxyl group and derivatives thereof, wherein the carboxyl carbon atom is attached to L2,
a phosphonic acid group and derivatives thereof,
an alpha-keto hydroxyalkyl group,
a hydroxyalkyl group wherein the carbon atom bonded to the hydroxyl group is further substituted with one or two trifluoro-methyl groups,
a substituted or unsubstituted five-membered heterocyclyl residue having in the ring at least two heteroatoms and at least one carbon atom, wherein
the at least one carbon atom of the ring is bonded to two heteroatoms;
at least one of the heteroatoms to which the carbon atom of the ring is bonded is a member of the ring;
and at least one of the heteroatoms to which the carbon atom of the ring is bonded or at least one of the heteroatoms of the ring is bearing a hydrogen atom;
or a prodrug or a pharmaceutically acceptable salt thereof for the manufacture of a medicament for the treatment of DGAT1 associated disorders.

According to a further aspect, the present invention provides use of a compound having the following chemical structure.

A-L1-B-C-D-L2-E wherein
A is a substituted or unsubstituted alkyl, cycloalkyl, aryl, or heterocyclyl group,
L1 is selected from the group consisting of:
an amine group —NH—
a substituted amine group of the formula —N(CH$_3$)—, —CH$_2$—NH— or —CH$_2$—CH$_2$—NH—,
an amide group —C(O)—NH—,
a sulphonamide group —S(O)$_2$—NH—, or
a urea group —NHC(O)—NH—,
B is a substituted or unsubstituted, monocyclic, 5- or 6-membered divalent heteroaryl group,
C-D is selected from the following cyclic structures:
C-D together is a substituted or unsubstituted divalent biphenyl group,
C is a substituted or unsubstituted divalent phenyl group and D is a single bond,
C is a substituted or unsubstituted divalent phenyl group, and D is a substituted or unsubstituted divalent non-aromatic monocyclic ring which is selected from a saturated or unsaturated divalent cycloalkyl group or a saturated or unsaturated divalent heterocycloalkyl group,
C-D together is a spiro residue, wherein
the first cyclic component is a benzo-fused cyclic component wherein the ring which is fused to the phenyl part is a 5- or 6-membered ring, optionally comprising one or more heteroatoms, the first cyclic component being attached to the moiety B via its phenyl part, and
the second cyclic component is a cycloalkyl or cycloalkylidenyl residue which is attached to L2,
L2 is selected from the group consisting of:
a single bond,
a divalent residue having the following structure:

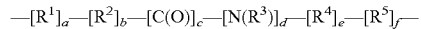

wherein
a is 0 or 1,
b is 0 or 1,
c is 0 or 1,
d is 0 or 1,
e is 0 or 1,
f is 0 or 1,
with the proviso that (a+b+c+d+e+f)>0, and c=1 if d=1,
$R^1$, $R^2$, $R^4$ and $R^5$, which can be the same or different, are a substituted or unsubstituted divalent alkyl, cycloalkyl, alkenyl, alkynyl, alkylene, aryl or heterocyclyl residue,
$R^3$ is H or hydrocarbyl, or $R^3$ and $R^4$ form together with the nitrogen atom to which they are attached a 5- or 6-membered heterocycloalkyl group,
an alkylidenyl group which is linked to the moiety D via a double bond,
with the proviso that L2 is not —C(O)—[$R^4$]$_e$—[$R^5$]$_f$— when C is a substituted or unsubstituted divalent phenyl group and D is a single bond, E is selected from the group consisting of:
a sulphonic acid group and derivatives thereof,
a carboxyl group and derivatives thereof, wherein the carboxyl carbon atom is attached to L2,
a phosphonic acid group and derivatives thereof,
an alpha-keto hydroxyalkyl group, a hydroxyalkyl group wherein the carbon atom bonded to the hydroxyl group is further substituted with one or two trifluoro-methyl groups, a substituted or unsubstituted five-membered heterocyclyl residue having in the ring at least two heteroatoms and at least one carbon atom, wherein the at least one carbon atom of the ring is bonded to two heteroatoms;

at least one of the heteroatoms to which the carbon atom of the ring is bonded is a member of the ring;

and at least one of the heteroatoms to which the carbon atom of the ring is bonded or at least one of the heteroatoms of the ring is bearing a hydrogen atom;

or a prodrug or a pharmaceutically acceptable salt thereof for the manufacture of a medicament for the treatment of DGAT1 associated disorders.

In a preferred embodiment, the compound used for the manufacture of the medicament is one of those as defined in claim 1, or is one of those as defined in the ALPHA, ALPHA', BETA, BETA', GAMMA, GAMMA', DELTA, DELTA', EPSILON, EPSILON', THETA, THETA', KAPPA, KAPPA', ZETA, ZETA' groups.

Among the preferred DGAT1 associated disorders, the following can be mentioned:

Metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris.

Preferably, the DGAT1 associated disorder is impaired glucose tolerance, Type 2 diabetes and obesity.

In yet another aspect, the present invention provides methods of using the compound or composition of the invention as an anorectic.

The compounds of the invention depending on the nature of the substituents possess one or more stereogenic centers. The resulting diastereoisomers, optical isomers, i.e., enantiomers, and geometric isomers, and mixtures thereof, are encompassed by the instant invention.

In a preferred embodiment, the moiety A is a substituted or unsubstituted phenyl group or a 6-membered heteroaryl group comprising one or two nitrogen atoms in the ring, L1 is —NH—, the moiety B is a substituted or unsubstituted divalent pyrimidine residue, the moiety C-D is selected from a substituted or unsubstituted divalent phenyl group (i.e. C) in combination with a single bond (i.e. D) or from a substituted or unsubstituted divalent phenyl group (i.e. C) in combination with a 5- or 6-membered cycloalkyl group (i.e. D), L2 is selected from a divalent $C_1$-$C_4$ alkyl group or from a divalent —C(O)—$C_1$-$C_4$ alkyl group, and E is selected from a carboxyl group or a derivative thereof.

In another preferred embodiment, the moiety A is a substituted or unsubstituted phenyl group, L1 is —NH—, the moiety B is a substituted or unsubstituted divalent oxazole residue, the moiety C-D is selected from a substituted or unsubstituted divalent phenyl group (i.e. C) in combination with a 5- or 6-membered cycloalkyl group (i.e. D), a substituted or unsubstituted divalent biphenyl group (i.e. C=D=phenyl), a substituted or unsubstituted divalent phenyl group (i.e. C) in combination with a divalent 5- or 6-membered non-aromatic heterocyclyl group, preferably a tetrahydro-pyridine group (i.e. D), L2 is selected from a divalent $C_1$-$C_4$ alkyl group, a divalent $C_1$-$C_4$ alkyl-C(O)—N(R)—$C_1$-$C_4$ alkyl group wherein R is H or a $C_1$-$C_4$ alkyl group, a divalent —C(O)—$C_1$-$C_4$ alkyl group, a divalent —C(O)—$C_5$-$C_6$ cycloalkyl group, a divalent —C(O)-phenyl group, a —C(O)— group, or a divalent —$R^1$-$R^2$— group wherein $R^1$ is cyclohexyl and $R^2$ is $C_1$-$C_4$ alkyl, and E is selected from a carboxyl group or derivative thereof or a sulphonic acid or derivative thereof, preferably a sulphonamide group.

In another preferred embodiment, the moiety A is a substituted or unsubstituted phenyl group, L1 is —NH—, the moiety B is a substituted or unsubstituted divalent thiazole residue, the moiety C-D is selected from a substituted or unsubstituted divalent phenyl group (i.e. C) in combination with a 5- or 6-membered cycloalkyl group (i.e. D) or from a substituted or unsubstituted biphenyl group (i.e. C=D=phenyl), L2 is selected from a divalent $C_1$-$C_4$ alkyl group or from a divalent —C(O)—$C_1$-$C_4$ alkyl group, and E is selected from a carboxyl group or a derivative thereof.

In another preferred embodiment, the moiety A is selected from substituted or unsubstituted alkyl, cycloalkyl, phenyl or a 5- or 6-membered heterocyclyl group comprising one or two nitrogen atoms in the ring, preferably pyridine, pyrazole or isoxazole, L1 is selected from —N(H)—, —C(O)NH—, or —NHC(O)—, the moiety B is a substituted or unsubstituted divalent pyridine, the moiety C-D is a divalent substituted or unsubstituted phenyl (i.e. C) in combination with a 5- or 6-membered cycloalkyl (i.e. D), L2 is a C1-C4 alkyl group or a spiro residue, and E is a carboxyl group or a derivative thereof. Preferably, the amino group representing L1 is attached to the pyridine residue representing moiety B either via ring position 2 or ring position 3.

In another preferred embodiment, the moiety A is selected from a substituted or unsubstituted alkyl, cycloalkyl, phenyl or a 5- or 6-membered heterocyclyl group comprising one or two nitrogen atoms in the ring, preferably pyridine, L1 is selected from —N(H)—, —C(O)NH—, or —NHC(O)—, the moiety B is a divalent substituted or unsubstituted pyridazine group, the moiety C-D is selected from a substituted or unsubstituted divalent phenyl group (i.e. C) in combination with a single bond (i.e. D), from a substituted or unsubstituted divalent phenyl group (i.e. C) in combination with a 5- or 6-membered cycloalkyl group which is optionally comprising a heteroatom like nitrogen (i.e. D), L2 is selected from a $C_1$-$C_4$ alkyl group, a —C(O)—N($R^1$)—$R^2$— group wherein $R^1$ and $R^2$ are joined so as to form a 5- or 6-membered non-aromatic heterocyclyl group, a —C(O)—N($R^1$)—$R^2$— group wherein $R^1$ is a $C_1$-$C_4$ alkyl group and $R^2$ is a 5- or 6-membered cycloalkyl group or a $C_1$-$C_4$ alkyl group, and E is selected from a carboxyl group or derivative thereof or a substituted or unsubstituted five-membered heterocyclyl residue having at least two heteroatoms and at least one carbon atom in the ring, preferably a tetrazole residue or an oxo-substituted oxadiazole residue.

Particular embodiments of the invention are the compounds:
(4-{4-[2-(3-Fluorophenylamino)-pyrimidin-5-yl]-phenyl}-cyclohexyl)-acetic acid,
{4-[4-(2-Phenylaminopyrimidin-5-yl)-phenyl]-cyclohexyl}-acetic acid,
4-{4-[2-(3-Fluorophenylamino)-pyrimidin-5-yl]-phenyl}-2,2-dimethyl-4-oxo-butyric acid,
(1S,2S)-2-{4-[2-(3-Fluorophenylamino)-pyrimidin-5-yl]-benzoyl}-cyclopentanecarboxylic acid,
(1S,2S)-2-{4-[2-(3-Chlorophenylamino)-pyrimidin-5-yl]-benzoyl}-cyclopentanecarboxylic acid,
(4-{4-[2-(3-Methoxyphenylamino)-thiazol-4-yl]-phenyl}-cyclohexyl)-acetic acid,
(4-{4-[2-(3-Fluorophenylamino)-thiazol-4-yl]-phenyl}-cyclohexyl)-acetic acid,
(4-{4-[2-(2-Chlorophenylamino)-thiazol-4-yl]-phenyl}-cyclohexyl)-acetic acid,
(4-{4-[2-(3-Cyanophenylamino)-thiazol-yl]-phenyl}-cyclohexyl)-acetic acid,
(4-{4-[2-(3-Trifluoromethylphenylamino)-thiazol-4-yl]-phenyl}-cyclohexyl)-acetic acid,
(4-{4-[2-(3-Fluorophenylamino)-thiazol-4-yl]-phenyl}-cyclohexyl)-acetic acid,
3-{4'-[2-(3-Fluorophenylamino)-thiazol-yl]-biphenyl-4-yl}-propionic acid,
{4'-[2-(3-Fluorophenylamino)-thiazol-4-yl]-biphenyl-4-}-acetic acid,
(4-{4-[2-(3-Chlorophenylamino)-oxazol-5-yl]-phenyl}-cyclohexyl)-acetic acid,
(4-{4-[2-(4-Chlorophenylamino)-oxazol-5-yl]-phenyl}-cyclohexyl)-acetic acid,
(4-{4-[2-(4-Methoxyphenylamino)-oxazol-5-yl]-phenyl}-cyclohexyl)-acetic acid,
(4-{4-[2-(2-Fluorophenylamino)-oxazol-5-yl]-phenyl}-cyclohexyl)-acetic acid,
{4-[4-(2-Phenylaminooxazol-5-yl)-phenyl]-cyclohexyl}-acetic acid,
(4-{4-[2-(3-Fluorophenylamino)-oxazol-5-yl]-phenyl}-cyclohexyl)-acetic acid,
(4-{4-[2-(2-Chlorophenylamino)-oxazol-5-yl]-phenyl}-cyclohexyl)-acetic acid,
(4-{4-[2-(3-Cyanophenylamino)-oxazol-5-yl]-phenyl}-cyclohexyl)-acetic acid,
{4-[4-(2-Cyclohexylaminooxazol-5-yl)-phenyl]-cyclohexyl}-acetic acid,
(4-{4-[2-(3,4-Dichlorophenylamino)-oxazol-5-yl]-phenyl}-cyclohexyl)-acetic acid,
(4-{4-[2-(3-Chloro-4-fluorophenylamino)-oxazol-5-yl]-phenyl}-cyclohexyl)-acetic acid,
(4-{4-[2-(4-Chloro-3-trifluoromethylphenylamino)-oxazol-5-yl]-phenyl}-cyclohexyl)-acetic acid,
(4-{4-[2-(3,5-Difluorophenylamino)-oxazol-5-yl]-phenyl}-cyclohexyl)-acetic acid,
(4-{4-[2-(3,5-Dichlorophenylamino)-oxazol-5-yl]-phenyl}-cyclohexyl)-acetic acid,
(4-{4-[2-(2-Chloro-4-trifluoromethylphenylamino)-oxazol-5-yl]-phenyl}-cyclohexyl)-acetic acid,
(4-{4-[2-(2-Trifluoromethylphenylamino)-oxazol-5-yl]-phenyl}-cyclohexyl)-acetic acid,
(4-{4-[2-(3-Fluoro-4-methylphenylamino)-oxazol-5-yl]-phenyl}-cyclohexyl)-acetic acid,
{4-[4-(2-p-Tolylaminooxazol-5-yl)-phenyl]-cyclohexyl}-acetic acid,
(4-{4-[2-(3-Chloro-4-methylphenylamino)-oxazol-5-yl]-phenyl}-cyclohexyl)-acetic acid,
4-(4-{4-[2-(3-Chlorophenylamino)-oxazol-5-yl]-phenyl}-cyclohexyl)-butyric acid,
(E)-4-(4-{4-[2-(3-Chlorophenylamino)-oxazol-5-yl]-phenyl}-cyclohexyl)-but-2-enoic acid,
3-[2-(4-{4-[2-(3-Chlorophenylamino)-oxazol-5-yl]-phenyl}-cyclohexyl)-acetylamino]-propionic acid,
{[2-(4-{4-[2-(3-Chlorophenylamino)-oxazol-5-yl]-phenyl}-cyclohexyl)-acetyl]-methyl-amino}-acetic acid,
{4'-[2-(3-Chlorophenylamino)-oxazol-5-yl]-biphenyl-4-yl}-acetic acid,
3-{4-[2-(3-Chlorophenylamino)-oxazol-5-yl]-biphenyl-4-yl}-propionic acid,
4-{4'-[2-(3-Chlorophenylamino)-oxazol-5-yl]-biphenyl-4-yl}-2,2-dimethyl-4-oxo-butyric acid,
4-{4'-[2-(3-Chlorophenylamino)-oxazol-5-yl]-biphenyl-4-yl}-4-oxo-butyric acid,
4-{4'-[2-(3-Chlorophenylamino)-oxazol-5-yl]-biphenyl-4-carbonyl}-cyclohexanecarboxylic acid,
(4-{4-[2-(3-Chlorophenylamino)-oxazol-5-yl]-phenyl}-3,6-dihydro-2H-pyridin-1-yl)-oxo-acetic acid,
4-{4-[2-(3-Chloro-phenylamino)-oxazol-5-yl]-phenyl}-3,6-dihydro-2H-pyridine-1-sulfonic acid amide,
4-{4-[2-(3-Chloro-phenylamino)-oxazol-5-yl]-phenyl}-3,6-dihydro-2H-pyridine-1-sulfonic acid amide-N-carboxylic acid tert-butyl ester,
4-(4-{4-[2-(3-Chloro-phenylamino)-oxazol-5-yl]-phenyl}-3,6-dihydro-2H-pyridin-1-yl)-2,2-dimethyl-4-oxo-butyric acid,
4-(4-{4-[2-(3-Chloro-phenylamino)-oxazol-5-yl]-phenyl}-3,6-dihydro-2H-pyridin-1-yl)-4-oxo-butyric acid,
2-(4-{4-[2-(3-Chloro-phenylamino)-oxazol-5-yl]-phenyl}-3,6-dihydro-2H-pyridine-1-carbonyl)-benzoic acid,
(1R,2R)-2-{4'-[2-(3-Chlorophenylamino)-oxazol-5-yl]-biphenyl-4-carbonyl}-cyclohexanecarboxylic acid,
(trans)-2-{4'-[2-(3-Chlorophenylamino)-oxazol-5-yl]-biphenyl-4-carbonyl}-cyclohexanecarboxylic acid,
(trans)-2-{4'-[2-(3-Chlorophenylamino)-oxazol-5-yl]-biphenyl-4-carbonyl}-cyclopentanecarboxylic acid,
(4-{4'-[2-(3-Chloro-phenylamino)-oxazol-5-yl]-biphenyl-4-yl}-cyclohexyl)-acetic acid,
(4-{5-[6-(6-Trifluoromethyl-pyridin-3-ylamino)-pyridin-3-yl]-spirocyclohexylidenyl-1,1'-indanyl}-acetic acid,
(4-{5-[6-(6-Trifluoromethyl-pyridin-3-ylamino)-pyridin-3-yl]-spirocyclohexyl-1,1'-indanyl}-acetic acid,
(4-{4-[6-(3-Chloro-phenylamino)-pyridin-3-yl]-phenyl}-cyclohexyl)-acetic acid,
(4-{4-[6-(3-methylphenylamino)-pyridin-3-yl]-phenyl}-cyclohexyl)-acetic acid,
(4-{4-[6-(3-Trifluoromethylphenylamino)-pyridin-3-yl]-phenyl}-cyclohexyl)-acetic acid,
(4-{4-[6-(3-Methoxyphenylamino)-pyridin-3-yl]-phenyl}-cyclohexyl)-acetic acid,
(4-{4-[6-(2-Fluorophenylamino)-pyridin-3-yl]-phenyl}-cyclohexyl)-acetic acid,
(4-{4-[6-(2-Methoxyphenylamino)-pyridin-3-yl]-phenyl}-cyclohexyl)-acetic acid,
(4-{4-[6-(2-Methoxyphenylamino)-pyridin-3-yl]-phenyl}-cyclohexyl)-acetic acid,
(4-{4-[5-(6-Trifluoromethyl-pyridin-3-ylamino)-pyridin-2-yl]-phenyl}-cyclohexyl)-acetic acid,
(4-{4-[5-(Pyridin-2-ylamino)-pyridin-2-yl]-phenyl}-cyclohexyl)-acetic acid,
{4-[4-(5-Phenylaminopyridin-2-yl)-phenyl]-cyclohexyl}-acetic acid,
(4-{4-[5-(5-Cyanopyridin-3-ylamino)-pyridin-2-yl]-phenyl}-cyclohexyl)-acetic acid, (4-{4-[5-(5-Trifluoromethylpyridin-2-ylamino)-pyridin-2-yl]-phenyl}-cyclohexyl)-acetic acid,
(4-{4-[5-(4-Trifluoromethylphenylamino)-pyridin-2-yl]-phenyl}-cyclohexyl)-acetic acid,
(4-{4-[5-(5-Methylpyridin-2-ylamino)-pyridin-2-yl]-phenyl}-cyclohexyl)-acetic acid,
(4-{4-[5-(5-Trifluoromethylpyridin-2-ylamino)-pyridin-2-yl]-phenyl}-cyclohexyl)-acetic acid methyl ester,
(4-{4-[5-(5-Chloropyridin-2-ylamino)-pyridin-2-yl]-phenyl}-cyclohexyl)-acetic acid,
(4-{4-[5-(6-Methoxypyridin-3-ylamino)-pyridin-2-yl]-phenyl}-cyclohexyl)-acetic acid,
(4-{4-[5-(5-Fluoropyridin-2-ylamino)-pyridin-2-yl]-phenyl}-cyclohexyl)-acetic acid,
(4-{4-[5-(6-Acetylaminopyridin-3-ylamino)-pyridin-2-yl]-phenyl}-cyclohexyl)-acetic acid,
{4-[4-(3-Methoxy-5-phenylamino-pyridin-2-yl)-phenyl]-cyclohexyl}-acetic acid,
{4-[4-(3-Methoxy-5-(3-fluorophenyl)amino-pyridin-2-yl)-phenyl]-cyclohexyl}-acetic acid,
{4-[4-(3-Methoxy-5-(4-trifluoromethyl-phenyl)amino-pyridin-2-yl)-phenyl]-cyclohexyl}-acetic acid,
{4-[4-(3-Methoxy-5-(3-chlorophenyl)amino-pyridin-2-yl)-phenyl]-cyclohexyl}-acetic acid,
(4-{4-[5-(3-Fluoro-phenylamino)-pyridin-2-yl]-phenyl}-cyclohexyl)-acetic acid,
(4-{4-[5-(3-Chloro-phenylamino)-pyridin-2-yl]-phenyl}-cyclohexyl)-acetic acid,
(4-{4-[5-(1-Methyl-1H-pyrazol-3-ylamino)-pyridin-2-yl]-phenyl}-cyclohexyl)-acetic acid,
(4-{4-[5-(5-Fluoro-6-methoxy-pyridin-3-ylamino)-pyridin-2-yl]-phenyl}-cyclohexyl)-acetic acid,
(4-{4-[5-(Isoxazol-3-ylamino)-pyridin-2-yl]-phenyl}-cyclohexyl)-acetic acid,
(4-{5-[5-(6-Trifluoromethyl-pyridin-3-ylamino)-pyridin-2-yl]-spirocyclohexylidenyl-1,1'-indanyl}-acetic acid,
(4-{4-[6-(3-Chloro-phenylamino)-pyridazin-3-yl]-phenyl}-cyclohexyl)-acetic acid,
(4-{4-[6-(3-Fluoro-phenylamino)-pyridazin-3-yl]-phenyl}-cyclohexyl)-acetic acid,
{4-[4-(6-m-Tolylamino-pyridazin-3-yl)-phenyl]-cyclohexyl}-acetic acid,
(4-{4-[6-(3-Trifluoromethyl-phenylamino)-pyridazin-3-yl]-phenyl}-cyclohexyl)-acetic acid,
(4-{4-[6-(3-Methoxy-phenylamino)-pyridazin-3-yl]-phenyl}-cyclohexyl)-acetic acid,
(4-{4-[6-(3-Cyano-phenyl amino)-pyridazin-3-yl]-phenyl}-cyclohexyl)-acetic acid,
(4-{4-[6-(2-Fluoro-phenylamino)-pyridazin-3-yl]-phenyl}-cyclohexyl)-acetic acid,
(4-{4-[6-(4-Chloro-phenylamino)-pyridazin-3-yl]-phenyl}-cyclohexyl)-acetic acid,
{4-[4-(6-p-Tolylamino-pyridazin-3-yl)-phenyl]-cyclohexyl}-acetic acid,
(4-{4-[6-(4-Trifluoromethyl-phenylamino)-pyridazin-3-yl]-phenyl}-cyclohexyl)-acetic acid,
(4-{4-[6-(3-Chloro-4-methoxy-phenylamino)-pyridazin-3-yl]-phenyl}-cyclohexyl)-acetic acid,
(4-{4-[6-(3-Chloro-2-methyl-phenylamino)-pyridazin-3-yl]-phenyl}-cyclohexyl)-acetic acid,
{4-[4-(6-Phenylamino-pyridazin-3-yl)-phenyl]-cyclohexyl}-acetic acid,
(4-{4-[6-(3-Chloro-2-methoxy-phenylamino)-pyridazin-3-yl]-phenyl}-cyclohexyl)-acetic acid,
(4-{4-[6-(2-Methoxy-phenylamino)-pyridazin-3-yl]-phenyl}-cyclohexyl)-acetic acid,
(4-{4-[6-(4-Methoxy-phenylamino)-pyridazin-3-yl]-phenyl}-cyclohexyl)-acetic acid,
(4-{4-[6-(6-Trifluoromethyl-pyridin-3-ylamino)-pyridazin-3-yl]-phenyl}-cyclohexyl)-acetic acid,
(4-{4-[6-(4-Trifluoromethoxy-phenylamino)-pyridazin-3-yl]-phenyl}-cyclohexyl)-acetic acid,
(4-{4-[6-(4-Fluoro-phenylamino)-pyridazin-3-yl]-phenyl}-cyclohexyl)-acetic acid,
(4-{4-[6-(6-Amino-pyridin-3-ylamino)-pyridazin-3-yl]-phenyl}-cyclohexyl)-acetic acid,
(4-{4-[6-(Methyl-m-tolyl-amino)-pyridazin-3-yl]-phenyl}-cyclohexyl)-acetic acid,
[4-(4-{6-[(3-Chloro-phenyl)-methyl-amino]-pyridazin-3-yl}-phenyl)-cyclohexyl]-acetic acid,
[4-(4-{6-[(3-Methoxy-phenyl)-methyl-amino]-pyridazin-3-yl}-phenyl)-cyclohexyl]-acetic acid,
(4-{4-[6-(2-Methyl-6-trifluoromethyl-pyridin-3-ylamino)-pyridazin-3-yl]-phenyl}-cyclohexyl)-acetic acid,
(4-{4-[6-(3-Chloro-2-methoxy-phenylamino)-pyridazin-3-yl]-phenyl}-cyclohexyl)-acetic acid,
2-{4-[6-(3-Chloro-phenylamino)-pyridazin-3-yl]-benzoylamino}-3-methyl-butyric acid,
(S)-1-{4-[6-(3-Chloro-phenylamino)-pyridazin-3-yl]-benzoyl}-pyrrolidine-2-carboxylic acid,
(1S,2R)-2-{4-[6-(3-Chloro-phenylamino)-pyridazin-3-yl]-benzoylamino}-cyclopentanecarboxylic acid,
3-{4-[6-(3-Chloro-phenylamino)-pyridazin-3-yl]-benzoylamino}-propionic acid,
(S)-3-{4-[6-(3-Chloro-phenylamino)-pyridazin-3-yl]-benzoylamino}-5-methyl-hexanoic acid,
(1S,2R)-2-{4-[6-(3-Chloro-phenylamino)-pyridazin-3-yl]-benzoylamino}-cyclohexanecarboxylic acid,
(S)-1-{4-[6-(3-Chloro-phenylamino)-pyridazin-3-yl]-benzoyl}-piperidine-2-carboxylic acid,
2-{4-[6-(3-Chloro-phenylamino)-pyridazin-3-yl]-benzoylamino}-2-methyl-propionic acid,
4-{4-[6-(3-Trifluoromethyl-phenylamino)-pyridazin-3-yl]-phenyl}-cyclohexanecarboxylic acid,
2-(4-{4-[6-(3-Chloro-phenylamino)-pyridazin-3-yl]-phenyl}-cyclohexyl)-acetamide,
(6-{4-[4-(2H-Tetrazol-5-ylmethyl)-cyclohexyl]-phenyl}-pyridazin-3-yl)-(6-trifluoromethyl-pyridin-3-yl)-amine,
3-(4-{4-[6-(6-Trifluoromethyl-pyridin-3-ylamino)-pyridazin-3-yl]-phenyl}-cyclohexylmethyl)-4H-[1,2,4]oxadiazol-5-one,
(1-{4-[6-(3-Trifluoromethyl-phenylamino)-pyridazin-3-yl]-phenyl}-piperidin-4-yl)-acetic acid,
(4-{4-[4-Methyl-6-(6-trifluoromethyl-pyridin-3-ylamino)-pyridazin-3-yl]-phenyl}-cyclohexyl)-acetic acid,
(4-{4-[4-Methyl-6-(4-trifluoromethyl-phenylamino)-pyridazin-3-yl]-phenyl}-cyclohexyl)-acetic acid,
(4-{4-[5-(6-Trifluoromethyl-pyridin-3-ylamino)-pyrazin-2-yl]-phenyl}-cyclohexyl)-acetic acid,
(4-{4-[5-(2,2-Dimethyl-propionylamino)-pyridin-2-yl]-phenyl}-cyclohexyl)-acetic acid,
(4-{4-[5-(Benzooxazol-2-ylamino)-pyridin-2-yl]-phenyl}-cyclohexyl)-acetic acid,
(4-{4-[6-(6-Methoxy-pyridin-3-ylamino)-5-methyl-pyridin-3-yl]-phenyl}-cyclohexyl)-acetic acid,
(4-{4-[5-Fluoro-6-(6-methoxy-pyridin-3-ylamino)-pyridin-3-yl]-phenyl}-cyclohexyl)-acetic acid,
Oxo-(4-{4-[6-(6-trifluoromethyl-pyridin-3-ylamino)-pyridin-3-yl]-phenyl}-cyclohexyl)-acetic acid,
{4-[4-(5-Acetylamino-pyridin-2-yl)-phenyl]-cyclohexyl}-acetic acid,
(4-{4-[5-(3-Trifluoromethyl-benzoylamino)-pyridin-2-yl]-phenyl}-cyclohexyl)-acetic acid,

[4-(4-{5-[(Pyridine-2-carbonyl)-amino]-pyridin-2-yl}-phenyl)-cyclohexyl]-acetic acid,
[4-(4-{5-[3-(4-Trifluoromethoxy-phenyl)-ureido]-pyridin-2-yl}-phenyl)-cyclohexyl]-acetic acid,
[4-(4-{5-[3-(2-Trifluoromethyl-phenyl)-ureido]-pyridin-2-yl}-phenyl)-cyclohexyl]-acetic acid,
(4-{4-[5-(3-o-Tolyl-ureido)-pyridin-2-yl]-phenyl}-cyclohexyl)-acetic acid,
[4-(4-{5-[(1-Methyl-1H-indole-3-carbonyl)-amino]-pyridin-2-yl}-phenyl)-cyclohexyl]-acetic acid,
[4-(4-{5-[(1H-Indole-3-carbonyl)-amino]-pyridin-2-yl}-phenyl)-cyclohexyl]-acetic acid,
[4-(4-{5-[(Pyridine-3-carbonyl)-amino]-pyridin-2-yl}-phenyl)-cyclohexyl]-acetic acid,
[4-(4-{5-[(6-Methyl-pyridine-3-carbonyl)-amino]-pyridin-2-yl}-phenyl)-cyclohexyl]-acetic acid,
[4-(4-{5-[(5-Bromo-pyridine-3-carbonyl)-amino]-pyridin-2-yl}-phenyl)-cyclohexyl]-acetic acid,
[4-(4-{5-[(5-Chloro-6-methoxy-pyridine-3-carbonyl)-amino]-pyridin-2-yl}-phenyl)-cyclohexyl]-acetic acid,
[4-(4-{5-[(5-Isobutyl-isoxazole-3-carbonyl)-amino]-pyridin-2-yl}-phenyl)-cyclohexyl]-acetic acid,
[4-(4-{5-[(3-tert-Butyl-1-methyl-1H-pyrazole-4-carbonyl)-amino]-pyridin-2-yl}-phenyl)-cyclohexyl]-acetic acid,
[4-(4-{5-[(5-tert-Butyl-1H-pyrazole-3-carbonyl)-amino]-pyridin-2-yl}-phenyl)-cyclohexyl]-acetic acid,
[4-(4-{5-[(5-Isopropyl-isoxazole-3-carbonyl)-amino]-pyridin-2-yl}-phenyl)-cyclohexyl]-acetic acid,
{4-[4-(5-Isobutoxycarbonylamino-pyridin-2-yl)-phenyl]-cyclohexyl}-acetic acid,
[4-(4-{5-[((S)-5-Oxo-pyrrolidine-2-carbonyl)-amino]-pyridin-2-yl}-phenyl)-cyclohexyl]-acetic add,
(4-{4-[5-(4-Fluoro-3-trifluoromethyl-benzoylamino)-pyridin-2-yl]-phenyl}-cyclohexyl)-acetic acid,
(4-{4-[5-(4-Trifluoromethyl-benzoylamino)-pyridin-2-yl]-phenyl}-cyclohexyl)-acetic acid,
[4-(4-{5-[(6-Trifluoromethyl-pyridine-3-carbonyl)-amino]-pyridin-2-yl}-phenyl)-cyclohexyl]-acetic acid,
(4-{4-[5-(3-Fluoro-5-trifluoromethyl-benzoylamino)-pyridin-2-yl]-phenyl}-cyclohexyl)-acetic acid,
[4-(4-{5-[(Tetrahydro-pyran-4-carbonyl)-amino]-pyridin-2-yl}-phenyl)-cyclohexyl]-acetic acid,
[4-(4-{5-[(5-Bromo-2-methoxy-pyridine-3-carbonyl)-amino]-pyridin-2-yl}-phenyl)-cyclohexyl]-acetic acid
[4-(4-{5-[(1,5-Dimethyl-1H-pyrazole-3-carbonyl)-amino]-pyridin-2-yl}-phenyl)-cyclohexyl]-acetic acid,
[4-(4-{5-[(5-Methoxy-1H-indole-3-carbonyl)-amino]-pyridin-2-yl}-phenyl)-cyclohexyl]-acetic acid,
[4-(4-{5-[(2,5-Dimethyl-1H-pyrrole-3-carbonyl)-amino]-pyridin-2-yl}-phenyl)-cyclohexyl]-acetic acid,
[4-(4-{5-[(1-Methyl-5-trifluoromethyl-1H-pyrazole-4-carbonyl)-amino]-pyridin-2-yl}-phenyl)-cyclohexyl]-acetic acid,
{4-[4-(5-{[4-(Morpholine-4-sulfonyl)-1H-pyrrole-2-carbonyl]-amino}-pyridin-2-yl)-phenyl]-cyclohexyl}-acetic acid,
(4-{4-[5-(2-Fluoro-2-methyl-propionylamino)-pyridin-2-yl]-phenyl}-cyclohexyl)-acetic acid,
[4-(4-{5-[(1-Methyl-3-trifluoromethyl-1H-pyrazole-4-carbonyl)-amino]-pyridin-2-yl}-phenyl)-cyclohexyl]-acetic acid methyl ester,
(4-{4-[5-(2-Methyl-2-pyrazol-1-yl-propionylamino)-pyridin-2-yl]-phenyl}-cyclohexyl)-acetic acid,
[4-(4-{5-[(5-Isopropyl-isoxazole-4-carbonyl)-amino]-pyridin-2-yl}-phenyl)-cyclohexyl]-acetic acid,
[4-(4-{5-[(1-Methyl-3-trifluoromethyl-1H-pyrazole-4-carbonyl)-amino]-pyridin-2-yl}-phenyl)-cyclohexyl]-acetic acid,
[4-(4-{5-[(5-Cyclopropyl-isoxazole-4-carbonyl)-amino]-pyridin-2-yl}-phenyl)-cyclohexyl]-acetic acid,
[4-(4-{5-[(5-Cyclopropyl-isoxazole-4-carbonyl)-amino]-pyridin-2-yl}-phenyl)-cyclohexyl]-acetic acid methyl ester,
[4-(4-{5-[(5-Cyclopropyl-isoxazole-3-carbonyl)-amino]-pyridin-2-yl}-phenyl)-cyclohexyl]-acetic acid,
[4-(4-{5-[(6-Methoxy-pyridine-3-carbonyl)-amino]-pyridin-2-yl}-phenyl)-cyclohexyl]-acetic acid,
(4-{4-[5-(2,2-Dimethyl-butyrylamino)-pyridin-2-yl]-phenyl}-cyclohexyl)-acetic acid,
(4-{4-[5-(2-Methoxy-2-methyl-propionylamino)-pyridin-2-yl]-phenyl}-cyclohexyl)-acetic acid,
[4-(4-{5-[(1,5-Dimethyl-1H-pyrazole-4-carbonyl)-amino]-pyridin-2-yl}-phenyl)-cyclohexyl]-acetic acid,
(4-{4-[5-(Tetrahydro-pyran-4-yloxycarbonylamino)-pyridin-2-yl]-phenyl}-cyclohexyl)-acetic acid,
{4-[4-(5-Cyclopropylmethoxycarbonylamino-pyridin-2-yl)-phenyl]-cyclohexyl}-acetic acid,
(4-{4-[5-(Tetrahydro-furan-2-ylmethoxycarbonylamino)-pyridin-2-yl]-phenyl}-cyclohexyl)-acetic acid,
(4-{4-[5-(Tetrahydro-pyran-2-ylmethoxycarbonylamino)-pyridin-2-yl]-phenyl}-cyclohexyl)-acetic acid,
(4-{4-[5-(3-Methyl-oxetan-3-ylmethoxycarbonylamino)-pyridin-2-yl]-phenyl}-cyclohexyl)-acetic acid,
(4-{4-[5-(Tetrahydro-pyran-4-ylmethoxycarbonylamino)-pyridin-2-yl]-phenyl}-cyclohexyl)-acetic acid,
(4-{4-[5-(2-Methyl-pyridin-3-ylmethoxycarbonylamino)-pyridin-2-yl]-phenyl}-cyclohexyl)-acetic acid,
[4-(4-{5-[3-(4-Chloro-3-trifluoromethyl-phenyl)-ureido]-pyridin-2-yl}-phenyl)-cyclohexyl]-acetic acid,
{4-[4-(5-Isopropylcarbamoyl-pyridin-2-yl)-phenyl]-cyclohexyl}-acetic acid,
{4-[4-(6-Carbamoyl-pyridin-2-yl)-phenyl]-cyclohexyl}-acetic acid,
{4-[4-(6-Isopropylcarbamoyl-pyridin-2-yl)-phenyl]-cyclohexyl}-acetic acid,
(4-{4-[5-(6-Trifluoromethyl-pyridin-3-ylcarbamoyl)-pyridin-2-yl]-phenyl}-cyclohexyl)-acetic acid,
(4-{4-[5-(4-Trifluoromethyl-benzenesulfonylamino)-pyridin-2-yl]-phenyl}-cyclohexyl)-acetic acid,
(4-{4-[5-(3-Trifluoromethyl-benzenesulfonylamino)-pyridin-2-yl]-phenyl}-cyclohexyl)-acetic acid,
(4-{4-[5-(1,2-Dimethyl-1H-imidazole-4-sulfonylamino)-pyridin-2-yl]-phenyl}-cyclohexyl)-acetic acid,
(4-{4-[5-(5-Fluoro-pyridin-3-ylamino)-pyridin-2-yl]-phenyl}-cyclohexyl)-acetic acid,
(4-{4-[5-(6-Isopropoxy-pyridin-3-ylamino)-pyridin-2-yl]-phenyl}-cyclohexyl)-acetic acid,
(4-{4-[5-(5-Bromo-pyridin-2-ylamino)-pyridin-2-yl]-phenyl}-cyclohexyl)-acetic acid,
(4-{4-[5-(2-Methoxy-pyrimidin-5-ylamino)-pyridin-2-yl]-phenyl}-cyclohexyl)-acetic acid,
(4-{4-[5-(6-Methylsulfanyl-pyridin-3-ylamino)-pyridin-2-yl]-phenyl}-cyclohexyl)-acetic acid,
(4-{4-[5-([1,2,4]Triazin-3-ylamino)-pyridin-2-yl]-phenyl}-cyclohexyl)-acetic acid,
(4-{4-[5-(2-Dimethylamino-pyrimidin-5-ylamino)-pyridin-2-yl]-phenyl}-cyclohexyl)-acetic acid,
(4-{4-[5-(5-Methylsulfanyl-pyridin-2-ylamino)-pyridin-2-yl]-phenyl}-cyclohexyl)-acetic acid,
(4-{4-[5-(3,5-Difluoro-pyridin-2-ylamino)-pyridin-2-yl]-phenyl}-cyclohexyl)-acetic acid, (4-{4-[5-(6-Trifluoromethyl-pyridin-3-ylamino)-pyridin-2-yl]-phenyl}-cyclohexyl)-acetic acid methyl ester,
(4-{4-[5-(5-Chloro-6-methoxy-pyridin-3-ylamino)-pyridin-2-yl]-phenyl}-cyclohexyl)-acetic acid,
(4-{4-[5-(5-Fluoro-4-methyl-pyridin-2-ylamino)-pyridin-2-yl]-phenyl}-cyclohexyl)-acetic acid,
(4-{4-[5-(3-Chloro-5-methyl-pyridin-2-ylamino)-pyridin-2-yl]-phenyl}-cyclohexyl)-acetic acid,
(4-{4-[5-(5-Difluoromethyl-6-methoxy-pyridin-3-ylamino)-pyridin-2-yl]-phenyl}-cyclohexyl)-acetic acid,
(4-{4-[5-(5-Methanesulfonyl-pyridin-2-ylamino)-pyridin-2-yl]-phenyl}-cyclohexyl)-acetic acid,
(4-{4-[3-Fluoro-5-(6-trifluoromethyl-pyridin-3-ylamino)-pyridin-2-yl]-phenyl}-cyclohexyl)-acetic acid,
(4-{4-[5-(1H-Benzoimidazol-2-ylamino)-pyridin-2-yl]-phenyl}-cyclohexyl)-acetic acid,
(4-{4-[5-(5-Trifluoromethyl-[1,3,4]oxadiazol-2-ylamino)-pyridin-2-yl]-phenyl}-cyclohexyl)-acetic acid,
(4-{4-[5-(6-Methyl-benzooxazol-2-ylamino)-pyridin-2-yl]-phenyl}-cyclohexyl)-acetic acid,
(4-{4-[5-(2-Methyl-5-trifluoromethyl-2H-pyrazol-3-ylamino)-pyridin-2-yl]-phenyl}-cyclohexyl)-acetic acid,
(4-{4-[5-(6-Chloro-benzooxazol-2-ylamino)-pyridin-2-yl]-phenyl}-cyclohexyl)-acetic acid methyl ester,
(4-{4-[5-(6-Chloro-benzooxazol-2-ylamino)-pyridin-2-yl]-phenyl}-cyclohexyl)-acetic acid,
(4-{4-[5-(5-Chloro-6-methoxy-benzooxazol-2-ylamino)-pyridin-2-yl]-phenyl}-cyclohexyl)-acetic acid,
(4-{4-[5-(5-tert-Butyl-[1,3,4]oxadiazol-2-ylamino)-pyridin-2-yl]-phenyl}-cyclohexyl)-acetic acid,
(4-{4-[2-(6-Trifluoromethyl-pyridin-3-ylamino)-pyrimidin-5-yl]-phenyl}-cyclohexyl)-acetic acid,
(4-{4-[2-(5-Chloro-pyridin-2-ylamino)-pyrimidin-5-yl]-phenyl}-cyclohexyl)-acetic acid
Oxo-(4-{4-[6-(6-trifluoromethyl-pyridin-3-ylamino)-pyridin-3-yl]-phenyl}-piperidin-1-yl) acetic acid,
(4-Hydroxy-4-{4-[6-(6-trifluoromethyl-pyridin-3-ylamino)-pyridin-3-yl]-phenyl}-piperidin-1-yl)-acetic acid,
(4-{4-[6-(2-Methyl-6-trifluoromethyl-pyridin-3-ylamino)-pyridin-3-yl]-phenyl}-cyclohexyl)-acetic acid,
or in any case a pharmaceutically acceptable salt thereof.

In a further embodiment, the above listed compounds are in the form of their corresponding potassium, sodium, hydrochloric, methanesulfonic, phosphoric or sulfuric acids salts. The salts can be prepared by the herein described methods.

In a further embodiment, the above listed compounds, wherein the moiety D is a substituted or unsubstituted divalent cyclohexyl group, are in a trans configuration as represented by figure "B"

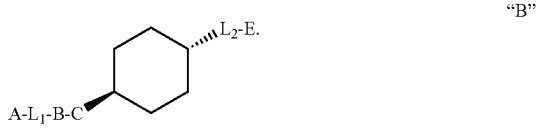

"B"

Use of a compound as herein described, or a prodrug or a pharmaceutically acceptable salt thereof for the manufacture of a medicament for the treatment of DGAT1 associated disorders.

The processes described herein for the preparation of compounds above may be conducted under inert atmosphere, preferably under nitrogen atmosphere.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or fractional crystallization.

Finally, compounds of the invention are either obtained in the free form, or in a salt form thereof, preferably, in a pharmaceutically acceptable salt form thereof, or as a prodrug derivative thereof.

Compounds of the instant invention which contain acidic groups may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether or acetonitrile. Resulting salts may be converted into the free compounds by treatment with acids. These or other salts can also be used for purification of the compounds obtained.

Alternatively, alkali metal salts of acidic compounds may also be prepared from the corresponding ester, i.e. the methyl or ethyl carboxylic acid ester. Treatment of the appropriate ester with an alkaline base such as sodium, potassium or lithium hydroxide in an ethereal or alcoholic solvent may directly afford the alkali metal salt, which may be precipitated from a reaction mixture by addition of a co-solvent such as diethyl ether or acetonitrile.

Compounds of the invention, in general, may be converted into acid addition salts, especially pharmaceutically acceptable salts. These are formed, e.g., with inorganic acids, such as mineral acids, e.g., sulfuric acid, phosphoric or hydrohalic acid, or with organic carboxylic acids, such as $(C_1-C_4)$-alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as $(C_1-C_4)$-alkylsulfonic acids, e.g., methanesulfonic acid; or arylsulfonic acids which are unsubstituted or substituted (for example by halogen). Preferred are salts formed with hydrochloric acid, maleic acid and methanesulfonic acid.

These salts may be prepared by suspension or dissolution of the preferred compounds in an organic solvent or water or appropriate mixture of the two, followed by addition of the appropriate acid. The resulting salt may be isolated by precipitation and or removal of solvent. Precipitation of the salt may be enhanced by addition of co-solvents such as ethereal solvents or acetonitrile, cooling, seeding, or other methods known to those skilled in the art.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described herein above, the compounds of the present invention may be employed for the treatment of conditions mediated by DGAT1 activity. Such compounds may thus be employed therapeutically for the treatment of impaired glucose tolerance, Type 2 diabetes and obesity.

In yet another aspect, the present invention provides methods of using a compound or composition of the invention to treat or prevent a disease or condition associated with DGAT1. Disease and conditions associated with lipid metabolism and cell proliferation, and complications thereof, may be treated with the subject compounds and compositions. In one group of embodiments, diseases and conditions, including chronic diseases, of humans and other species that can be treated with inhibitors of DGAT1 function include, but are not limited to, metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris.

In yet another aspect, the present invention provides methods of using a compound or composition of the invention as an anorectic.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by DGAT1 activity. Such conditions include impaired glucose tolerance, Type 2 diabetes and obesity.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin-capsules comprising the active ingredient together with:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, welting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by DGAT1 activity, preferably, impaired glucose tolerance, Type 2 diabetes and obesity.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;

c) anti-obesity agents such as orlistat, sibutramine and Cannabinoid Receptor 1 (CB1) antagonists e.g. rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 1 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

In each case in particular in the compound claims and the final products of the working examples, the subject matter of the final products, the pharmaceutical preparations and the claims are hereby incorporated into the present application by reference to these publications and patent applications.

Thus the invention covers pharmaceutical compositions comprising;
i) a compound according to claims 1, and
ii) at least one compound selected from
    a) antidiabetic agents,
    b) hypolipidemic agents,
    c) anti-obesity agents,
    d) anti-hypertensive agents,
    e) agonists of peroxisome proliferator-activator receptors,
ii) one or more pharmaceutically acceptable carriers.

Other specific anti-diabetic compounds are described by Patel Mona in *Expert Opin Investig Drugs*, 2003, 12-(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by DGAT1 activity, preferably, impaired glucose tolerance, Type 2 diabetes and obesity.

Thus, the present invention also relates to a compound as defined in the claims and described above for use as a medicament; to the use of a compound as defined in the claims and described above for the preparation of a pharmaceutical composition for the prevention and/or treatment of conditions mediated by DGAT1 activity, and to a pharmaceutical composition for use in conditions mediated by DGAT1 activity comprising a compound as defined in the claims and described above, or a pharmaceutically acceptable salt thereof, in association with a pharmaceutically acceptable diluent or carrier therefore.

The present invention further provides a method for the prevention and/or treatment of conditions mediated by DGAT1 activity, which comprises administering a therapeutically effective amount of a compound of the present invention.

A unit dosage for a mammal of about 50-70 kg may contain between about 1 mg and 1000 mg, advantageously between about 5-500 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound as defined in the claims and described above, or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents and anti-hypertensive agents, or a pharmaceutically acceptable salt thereof. The kit may comprise instructions for its administration. The combination can be a fixed combination (e.g. in the same pharmaceutical composition) or a free combination (e.g. in separate pharmaceutical compositions).

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent and an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound as defined in the claims and described above, or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of the DGAT1 activity.

Preferably, the condition associated with DGAT1 activity is selected from impaired glucose tolerance, Type 2 diabetes and obesity.

Finally, the present invention provides a method or use which comprises administering a compound as defined in the claims and described above in combination with a therapeutically effective amount of an anti-diabetic agent, a hypolipidemic agent, an anti-obesity agent or an anti-hypertensive agent.

Ultimately, the present invention provides a method or use which comprises administering a compound as defined in the claims and described above in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the route of administration, between about 0.1 mg/kg and 1000 mg/kg, preferably between about 1 mg/kg and 100 mg/kg.

The activity of compounds according to the invention may be assessed by the following methods or methods well-described in the art:

The enzyme preparation used in this assay is a membrane preparation from Sf9 cells overexpressing human $(His)_6$ DGAT1. During all steps samples were chilled to 4° C. Sf9 cells expressing human $(His)_6$DGAT1 were thawed at RT and re-suspended at a 10:1 ratio (mL buffer/g of cells) in 50 mM HEPES, 1× Complete Protease Inhibitor, pH 7.5.

The re-suspended pellet was homogenized for 1 min using a Brinkman PT 10/35 homogenizer with a 20 mm generator. Cells were lysed using Avestin Emulsiflex (chilled to 4° C.) at 10000-15000 psi. Lysate was centrifuged at 100,000×g for 1 h at 4° C. Supernatant was removed and pellets were re-suspended in 50 mM HEPES, 1× Complete Protease Inhibitor, pH 7.5 at ⅙ the volume of supernatant. Re-suspended pellets were pooled and homogenized with 10 strokes of a Glas-Col motor driven teflon pestle on setting 70. The protein concentration of the membrane preparation was quantified using BCA protein assay with 1% SDS. The membrane preparation was aliquoted, frozen on dry ice, and stored at −80° C.

For 50 mL, 25 mL of 0.2 M HEPES stock buffer, 0.5 mL of 1 M $MgCl_2$ (5 mM final concentration), and 24.5 mL of milli-Q $H_2O$ are added to the 55 mL Wheaton Potter-Elvehjem homogenizer. Enzyme preparation (0.1 mL) is added to buffer and the mixture is homogenized with 5 strokes on ice using the Glas-Col variable speed homogenizer system on setting 70.

For 50 mL, 0.5 mL 10 mM diolein is added to 9.5 mL of EtOH in a 50 mL Falcon screw cap conical centrifuge tube. Five mL of 10 mM sodium acetate pH 4.5 is added followed by 0.5 mL of 10 mM oleoyl-CoA. Finally, the remaining 4.5 mL of 10 mM sodium acetate pH 4.5 is added followed by 30 mL of milli-Q $H_2O$. The solution should be gently agitated by hand to induce mixing. The final concentrations of EtOH and sodium acetate are 20% and 2 mM, respectively.

Dry compounds are dissolved in the appropriate volume of DMSO to a final concentration of 10 mM. A 10-point, 3-fold dose response is used to evaluate compound potency. All dilutions are performed in DMSO in a Greiner 384-well microplate.

1. 2 μL of compound in DMSO is added to the appropriate wells. 2 μL of DMSO is added to 100% activity and 100% inhibition controls.
2. 25 μL of enzyme mix is added to all wells and plate(s) are incubated for 10 min at RT.
3. 10 μL of 20% acetic acid quench is added to 100% inhibition control wells. Plate(s) are vortexed using Troemner multi-tube vortexer (setting 7 for 10 sec).

4. 25 μL of substrate mix is added to all wells. Plate(s) are vortexed using Troemner multi-tube vortexer (setting 7 for 10 sec). Plate(s) are incubated for 30 min at RT.
5. 10 μL of 20% acetic acid quench is added to all wells. Plate(s) are vortexed using Troemner multi-tube vortexer (setting 7 for 10 sec).
6. 50 μL of 1-butanol w/glyceryl tripalmitoleate internal standard is added to all wells.
7. Plate(s) are sealed with super pierce strong plate sealer using the thermo-sealer.
8. Plate(s) are vortexed using Troemner multi-tube vortexer (setting 10 for 5 min).
9. Plate(s) are centrifuged at 162×g (1000 rpm for GH-3.8 rotor) for 5 min using Beckman GS-6R tabletop centrifuge.

Samples were analyzed by LC/MS/MS using a Waters 1525μ LC and Quattro Micro API MS. Where indicated, tripalmitolein was used as an internal standard to control for instrument variation.

Data is converted to % inhibition prior to curve fitting using the following equation:

$$\% \text{ Inhibition} = \frac{(\text{response compound} - \text{response } 100\% \text{ inhibition control})}{(\text{response } 100\% \text{ activity control} - \text{response } 100\% \text{ inhibition control})} \times 100$$

Using the method described above, the compounds of the present invention were shown to possess inhibitory activity with IC50 values ranging from 0.001 uM to 100 uM.

Table 1 shows the inhibitory activity ($IC_{50}$ values) of representative compounds to human DGAT1.

| Example | $IC_{50}$ (μM) |
|---------|----------------|
| 3-15    | 0.6            |
| 3-25    | 1.4            |
| 3-33    | 11             |
| 6-29    | 0.23           |

Methods of Preparation

Compounds of the present invention may be prepared from commercially available reagents employing general synthetic techniques known to those skilled in the art. Outlined below are reaction schemes suitable for preparing such compounds. Further exemplification is found in the specific examples provided.

Scheme 1

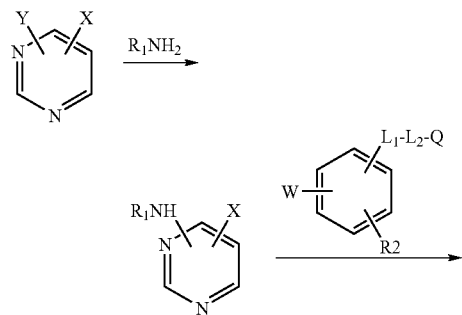

-continued

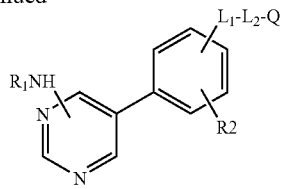

As shown in Scheme 1, compounds of the present invention where B is a pyrimidine ring may be prepared from a suitably functionalized starting material. For instance, in the synthetic sequence shown above, Y may be a halogen atom, toluenesulfonate, methanesulfonate, or trifluoromethanesulfonate. The amine derivative (described above as $R_1NH2$) may be condensed with the functionalized pyrimidine in the presence of acid (i.e., concentrated HCl, sulfuric acid, or ammonium chloride) or base (sodium hydride, alkyl lithiums, lithium amides, triethylamine, DBU), in an organic or aqueous solvent, typically at elevated temperature, to afford the aminopyrimidine adduct. This transformation may also be facilitated through transition metal catalysis; for example, copper or palladium reagents which may be complexed with additional ligands (for example, phosphine ligands such as BINAP, X-Phos, tri-t-butyl phosphine or amino ligands such as N,N-cyclohexane diamine derivatives) in the presence of a base may facilitate the amino pyrimidine synthesis.

The resulting amino pyrimidine may then be coupled to a suitably functionalized arene intermediate. For example, where X is a halogen atom, toluenesulfonate, methanesulfonate, or trifluoromethanesulfonate, W in the scheme above may be an organometallic substituent (for example, boron, tin, zinc, magnesium) that may be subjected to transition-metal cross coupling conditions known to those skilled in the art. Such cross-coupling events may be promoted by palladium complexes such as $Pd(OAc)_2$ or $Pd(PPh_3)_4$ that may be additionally supported by ligands (phosphines, N-heterocyclic carbenes). These reactions may be conducted in the presence of inorganic bases such as sodium carbonate or potassium acetate under aqueous or anhydrous conditions.

For cases where Q is a protected carboxylic acid derivative, hydrolysis may be promoted by aqueous bases such as lithium hydroxide or alternatively under acidic conditions to afford the final compound.

Scheme 2

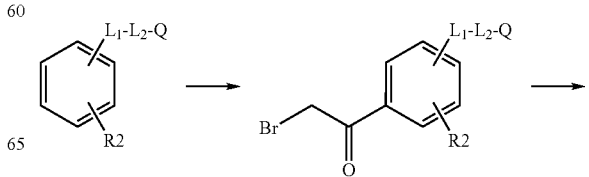

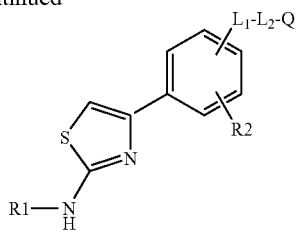

As shown in Scheme 2, compounds in the current invention where B is a thiazole ring may be prepared starting from the appropriate phenyl derivative. Acylation with an activated carboxylic acid derivative (acid chloride or acid bromide) in the presence of a Lewis acid such as aluminium trichloride may afford the bromo acetophenone derivative shown above. Condensation of this intermediate with a suitably functionalized thiourea in the presence of a base such as potassium carbonate or triethylamine may produce the amino thiazole shown above.

Scheme 3

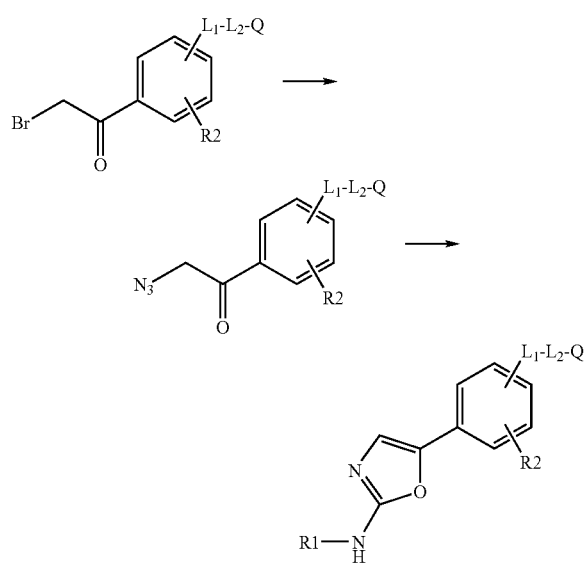

For compounds of the current invention where B is an oxazole ring, the general synthetic sequence described in Scheme 3 may be used. Conversion of the bromo acetophenone derivative to the corresponding azido intermediate may occur via reaction of sodium or lithium azide in an organic solvent which may or may not contain water. The azido ketone intermediate may then be treated with a triaryl- or trialkylphosphine (such as triphenylphosphine) in the presence of an isothiocyanate to afford the corresponding amino oxazole. This cyclization often requires heating, and is described by Dhar et al in *Bioorg. Med. Chem. Lett* 12 (2002) 3125-3128.

Scheme 4

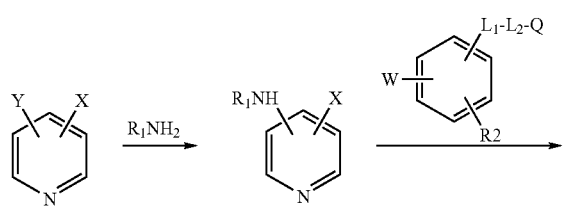

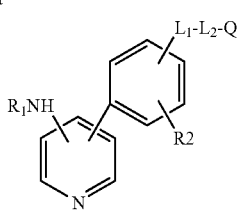

For compounds of the current invention where B is a pyridine ring, the general synthetic sequence described in Scheme 4 may be used. An amino derivative may be reacted with the appropriate pyridine derivative to afford the corresponding amino pyridine intermediate. For example, when Y is a suitably-placed leaving group (i.e., in the 2- or 4-position) such as halogen atom, toluenesulfonate, methansulfonate, or trifluoromethanesulfonate, the amino derivative $R_1NH_2$ may be reacted in the presence of acid (such as HCl or sulphuric acid) or base (such as sodium hydride, triethylamine, or DBU) to afford the amino pyridine intermediate. The use of transition metals such as palladium or copper may also facilitate this transformation, regardless of where Y is disposed. Alternatively, copper salts may mediate the process where Y is a boronic acid or ester derivative [See Tet. Lett. (1998) vol. 39, p. 2941]. The resulting amino pyridine derivative may then be coupled to the aryl-W intermediate above using transition metal-catalyzed cross-coupling methodology. For instance, where W is a boronic acid/ester, trialkyltin, or trialkylsilane, the appropriate aryl-X partner where X is a halogen atom or sulfonate may be reacted in the presence of a transition metal such as palladium with or without a supporting ligand to effect this carbon-carbon bond construction. Alternatively, W and X may be reversed in this bond disconnection.

Alternatively, the sequence above may be re-ordered as follows:

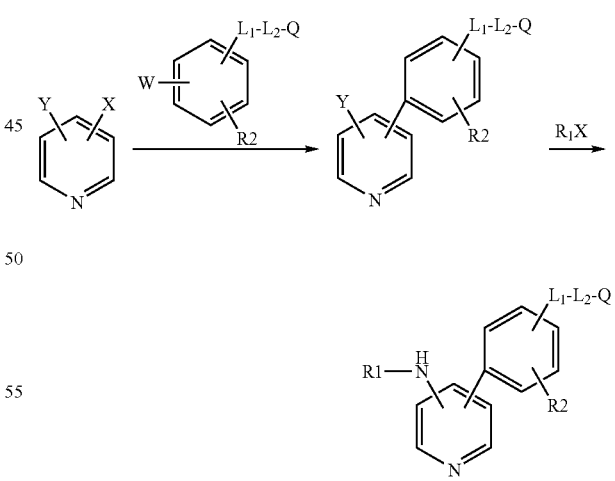

In the above scheme, W may be a boronic ester or suitable equivalent, X may be a halogen or appropriate sulfonate, and Y may be a nitrogen precursor such as nitro or protected nitrogen such as NHBoc. Y may then be elaborated to the corresponding amino derivative, which may then be coupled with the appropriate R1-X derivative under acidic, basic, or metal-promoted conditions as described above.

Scheme 5

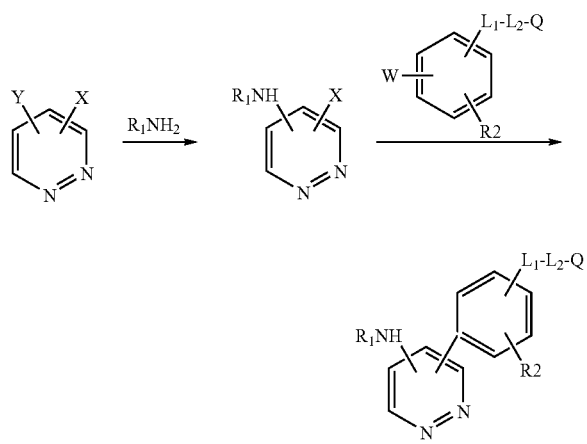

For compounds of the current invention where B is a pyridazine ring, the synthetic sequence shown in Scheme 5 may be applied. A difunctionalized pyridazine intermediate, for instance 3,6-dichloropyridazine, may be reacted with an amino nucleophile $R_1NH_2$ in the presence of acid (such as HCl or sulphuric acid) or base (such as sodium hydride, triethylamine, or DBU) to afford the amino pyridazine intermediate. The use of transition metals such as palladium or copper may also facilitate this transformation, regardless of where X and Y are disposed. The resulting amino pyridazine derivative may then be coupled to the aryl-W intermediate above using transition metal-catalyzed cross-coupling methodology. For instance, where W is a boronic acid/ester, trialkyltin, or trialkylsilane, the appropriate aryl-X partner where X is a halogen atom or sulfonate may be reacted in the presence of a transition metal such as palladium with or without a supporting ligand to effect this carbon-carbon bond construction. Alternatively, W and X may be reversed in this bond disconnection.

Scheme 6

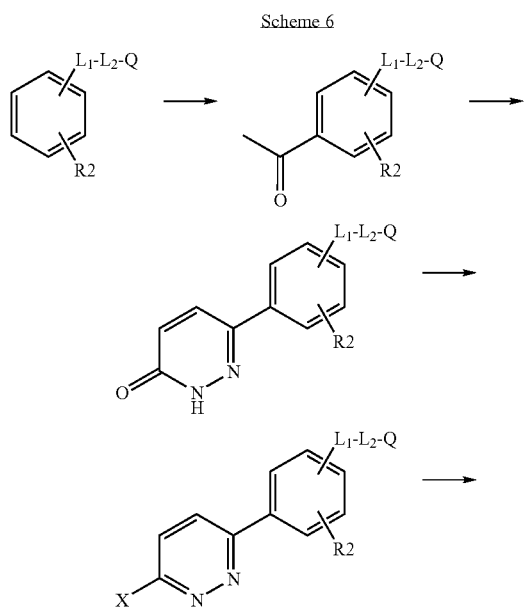

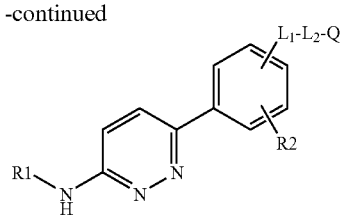

The compounds of the current invention where B is a pyridazine ring may also be prepared by the synthetic sequence shown in Scheme 6. Acylation of the starting arene derivative with the appropriate carboxylic acid derivative (i.e., an acid chloride) in the presence of a Lewis acid such as aluminium trichloride may produce the acetophenone derivative shown. Construction of the pyridazone ring may be effected by analogy to literature precedence (*Synthesis* (1993) p. 334). Activation of the pyridazone intermediate via the chloro or bromo pyridazine may be accomplished via phosphorous oxychloride, phosphorous bromide, or equivalent activating reagent. Substitution with the amine $R_1$—$NH_2$ then may occur under acidic, basic, or transition-metal promoted conditions.

Scheme 7

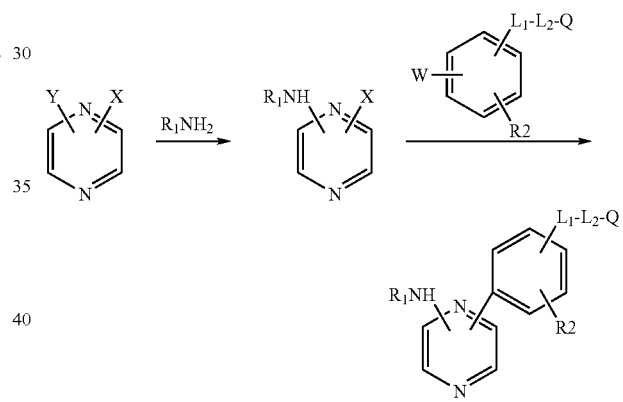

For compounds of the current invention where B is a pyrazine ring, the synthetic sequence shown in Scheme 7 may be applied. A difunctionalized pyrazine intermediate may be reacted with an amino nucleophile $R_1NH_2$ in the presence of acid (such as HCl or sulphuric acid) or base (such as sodium hydride, triethylamine, or DBU) to afford the amino pyridine intermediate. The use of transition metals such as palladium or copper may also facilitate this transformation, regardless of where X and Y are disposed. The resulting amino pyrazine derivative may then be functionalized with an X group such as halogen or sulfonate, and then coupled to the aryl-W intermediate above using transition metal-catalyzed cross-coupling methodology. For instance, where W is a boronic acid/ester, trialkyltin, or trialkylsilane, the appropriate aryl-X partner may be reacted in the presence of a transition metal such as palladium with or without a supporting ligand to effect this carbon-carbon bond construction. Alternatively, W and X may be reversed in this bond disconnection.

EXAMPLES

The following Examples are intended to illustrate the invention and are not to be construed as being limitations thereon. If not mentioned otherwise, all evaporations are performed under reduced pressure, preferably between about 50 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

HPLC Conditions:

A: Inertsil 4.6 mm×5 cm C8-3 column, 10 to 90% Acetonitrile in 5 mM ammonium formate, 2 min gradient, 4 mL/min, 50 degrees centigrade B: Inertsil 4.6 mm×5 cm C8-3 column, 40 to 90% Acetonitrile in 5 mM ammonium formate, 2 min gradient, 4 mL/min, 50 degrees centigrade C: Inertsil 4.6 mm×5 cm C8-3 column, 40 to 90% Acetonitrile in 0.1% acetic acid, 2 min gradient, 4 mL/min, 50 degrees centigrade D: Column: Atlantis C18 (Waters, Inc.), 15 cm×4.6 mm×5 µm
   Column temperature: Ambient
   Flow rate: 1.4 mL/min
   Injection volume: 3.0 µL
   Gradient: A=0.1% Trifluoroacetic Acid (TFA) in Water
   B=0.05% Trifluoroacetic Acid (TFA) in Acetonitrile
   0-95% B in 19.0 min, 1.8 min hold E: Gemini C18 4.6×50 mm, 5 um particle size; 5-100% ACN/H2O+5 mM NH40H/8 min Example 1-1

(4-{4-[2-(3-Fluorophenylamino)-pyrimidin-5-yl]-phenyl}-cyclohexyl)-acetic acid

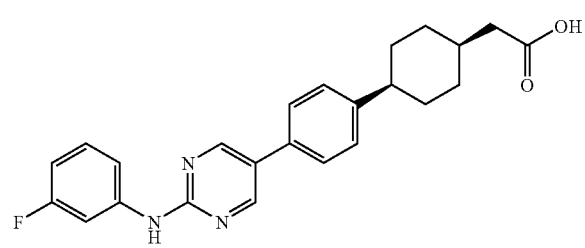 [SMILES: O=C(O)C[C@H]1CC[C@@H](c2ccc(-c3cnc(Nc4cccc(F)c4)nc3)cc2)CC1]

A. (5-Bromopyrimidin-2-yl)-(3-fluorophenyl)-amine

In a microwave vial is added 3-fluorophenylamine (0.293 mL, 2.58 mmol), 5-bromo-2-chloropyrimidine (500 mg, 2.58 mmol), EtOH (10 mL) and concentrated HCl (0.2 mL). The reaction mixture is then heated at 50° C. for 15 min. Water (20 mL) is added and it is extracted with EtOAc. The organic layer is washed with NaHCO$_3$, dried with Na$_2$SO$_4$ and concentrated. The residue is purified by column chromatography to give the title compound: 1H NMR (400 MHz, CHLOROFORM-d) δ ppm 6.83-6.88 (m, 1H) 7.24-7.26 (m, 1H) 7.28 (br. s., 1H) 7.34-7.40 (m, 1H) 7.74 (dt, J=11.37, 2.27 Hz, 1H) 8.56 (s, 2H); (M+H)+269.9.

B. (4-{4-[2-(3-Fluorophenylamino)-pyrimidin-5-yl]-phenyl}-cyclohexyl)-acetic acid methyl ester The mixture of (5-bromopyrimidin-2-yl)-(3-fluorophenyl)-amine (75 mg, 0.28 mmol), {4-[4-(4,4,5,5-tetramethyl-[1,3,2]dioxaborolan-2-yl)-phenyl]-cyclohexyl}-acetic acid methyl ester (Patent WO2004 047755) (100 mg, 0.28 mmol), PdCl$_2$dppf (12 mg, 0.014 mmol), sodium carbonate (2M solution, 0.35 mL) and DME (2 mL) is heated in a microwave at 125° C. for 15 min. The reaction mixture is extracted with EtOAc, washed with NH$_4$Cl solution. The organic phase is dried with MgSO$_4$, filtered and it is used directly in the next step: (M+H)+420.3.

C. (4-{4-[2-(3-Fluorophenylamino)-pyrimidin-5-yl]-phenyl}-cyclohexyl)-acetic acid To a solution of (4-{4-[2-(3-fluorophenylamino)-pyrimidin-5-yl]-phenyl}-cyclohexyl)-acetic acid methyl ester (crude from above) in DMF (2.5 mL) is added LiOH (10% solution, 1 mL) and the reaction mixture is heated at 60° C. for 1.5 h. The mixture is then subjected to HPLC purification to give the title compound: $^1$H NMR (400 MHz, DMSO-d6) δ 1.09-1.15 (m, 1H) 1.50 (td, J=12.44, 9.98 Hz, 1H) 1.63 (d, J=5.31 Hz, 6H) 2.37 (d, J=7.58 Hz, 2H) 6.76 (td, J=8.21, 2.27 Hz, 1H) 7.28-7.39 (m, 4H) 7.52 (dd, J=8.34, 1.26 Hz, 1H) 7.65 (s, 1H) 7.63 (t, J=4.04 Hz, 2H) 7.87 (d, J=12.38 Hz, 1H) 8.84-8.86 (m, 2H) 9.99 (s, 1H); (M+H)+=406.2.

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt.

The examples below were synthesized in analogous fashion using boronate esters (in step B) that are known in the literature: for example, 2,2-dimethyl-4-oxo-4-[4-(4,4,5,5-tetramethyl-[1,3,2]dioxaborolan-2-yl)-phenyl]-butyric acid (patent US 2004 0224997) and (1S,2S)-2-[4-(4,4,5,5-tetramethyl-[1,3,2]dioxaborolan-2-yl)-benzoyl]-cyclopentanecarboxylic acid (patent US 2004 0224997).

| Example | Chemical Name | LC rt | Method | MS (M + H)+ |
|---|---|---|---|---|
| 1-2 | {4-[4-(2-Phenylaminopyrimidin-5-yl)-phenyl]-cyclohexyl}-acetic acid | 1.44 | A | 388.2 |
| 1-3 | 4-{4-[2-(3-Fluorophenylamino)-pyrimidin-5-yl]-phenyl}-2,2-dimethyl-4-oxo-butyric acid | 1.31 | A | 394.1 |
| 1-4 | (1S,2S)-2-{4-[2-(3-Fluorophenylamino)-pyrimidin-5-yl]-benzoyl}-cyclopentanecarboxylic acid | 1.28 | A | 406.1 |
| 1-5 | (1S,2S)-2-{4-[2-(3-Chlorophenylamino)-pyrimidin-5-yl]-benzoyl}-cyclopentanecarboxylic acid | 1.33 | A | 422.1 |

Example 1-6

(4-{4-[2-(6-Trifluoromethyl-pyridin-3-ylamino)-pyrimidin-5-yl]-phenyl}-cyclohexyl)-acetic acid

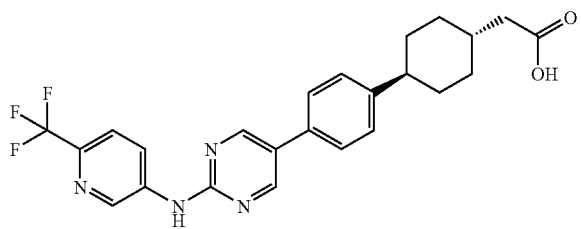 [SMILES: O=C(O)C[C@H]1CC[C@H](c2ccc(-c3cnc(Nc4ccc(C(F)(F)F)nc4)nc3)cc2)CC1]

{4-[4-(2-Chloro-pyrimidin-5-yl)-phenyl]-cyclohexyl}-acetic acid methyl ester

PdCl$_2$dppf (120 mg, 0.140 mmol) is added to a degassed mixture of {4-[4-(4,4,5,5-tetramethyl-[1,3,2]dioxaborolan-2-yl)-phenyl]-cyclohexyl}-acetic acid methyl ester (1.00 g, 2.79 mmol), 5-bromo-2-chloro-pyrimidine (540 mg, 2.79 mmol), 2 M Na$_2$CO$_3$ (2.8 mL), and DME (7.5 mL). The mixture is sealed in a glass tube and heated to 120° C. for 20 min by microwave irradiation. The reaction is diluted with EtOAc (150 mL), and the resulting suspension filtered. The filtrate is extracted with 1 N HCl (25 mL) and the organic layer dried over Na$_2$SO$_4$. Concentration followed by silica gel chromatography (20% EtOAc/Hexanes) affords {4-[4-(2-chloro-pyrimidin-5-yl)-phenyl]-cyclohexyl}-acetic acid methyl ester as a white solid: 1H NMR (400 MHz, CHLOROFORM-d) δppm 1.14-1.27 (m, 2H) 1.49-1.61 (m, 2H) 1.86-1.98 (m, 5H) 2.28 (d, J=6.82 Hz, 2H) 2.56 (tt, J=12.22, 3.19 Hz, 1H) 3.70 (s, 3H) 7.37 (d, J=8.08 Hz, 2H) 7.49 (d, J=8.34 Hz, 2H) 8.81 (s, 2H); (M+H)+345.1.

(4-{4-[2-(6-Trifluoromethyl-pyridin-3-ylamino)-pyrimidin-5-yl]-phenyl}-cyclohexyl)-acetic acid To a glass vial add 6-trifluoromethyl-pyridin-3-ylamine (35 mg, 0.217 mmol), {4-[4-(2-chloro-pyridin-5-yl)-phenyl]-cyclohexyl}-acetic acid methyl ester (50 mg, 0.145 mmol), Pd(OAc)$_2$-(5 mg, 5% mol), X-Phos (7 mg, 10% mol), and Cs$_2$CO$_3$ (118 mg, 0.363 mmol). Flush with N$_2$. Add tBuOH (0.25 mL), toluene (0.75 mL), and seal the tube. The reaction mixture is heated to 150° C. for 30 min by microwave irradiation. The reaction is diluted with EtOAc and filtered. The filtrate is concentrated and chromatographed on silica gel (25-50% EtOAc/Hexanes) to afford (4-{4-[2-(6-Trifluoromethyl-pyridin-3-ylamino)-pyrimidin-5-yl]-phenyl}-cyclohexyl)-acetic acid methyl ester as 90% pure. (4-{4-[2-(6-Trifluoromethyl-pyridin-3-ylamino)-pyrimidin-5-yl]-phenyl}-cyclohexyl)-acetic acid methyl ester (45 mg, 0.096 mmol) is taken up in DMF (1.5 mL) and 4 M LiOH (0.5 mL) and stirred at room temperature for 16 h. The reaction is heated to 50° C. for 12 h and then heated to 70° C. for 8 h. The reaction is diluted with 1 N HCl (2 mL) and H$_2$O (2 mL). The precipitate is collected by filtration and purified by HPLC (Xterra C8 30×100 mm, 22-50% ACN/H2O+5 mM NH4OH) to afford (4-{4-[2-(6-Trifluoromethyl-pyridin-3-ylamino)-pyrimidin-5-yl]-phenyl}-cyclohexyl)-acetic acid as a white solid: 1H NMR (400 MHz, DMSO-d6) δ ppm 1.05-1.18 (m, 2H) 1.43-1.56 (m, J=12.95, 12.66, 12.66, 3.16 Hz, 2H) 1.68-1.87 (m, 6H) 2.08 (d, J=6.57 Hz, 2H) 7.35 (d, J=8.34 Hz, 2H) 7.65 (d, J=8.34 Hz, 2H) 7.85 (d, J=8.59 Hz, 1H) 8.55 (dd, J=8.59, 2.02 Hz, 1H) 8.91 (s, 2H) 9.06 (d, J=2.27 Hz, 1H) 10.42 (s, 1H); (M+H)+457.0.

Using analogous procedures, the following compounds may also be prepared:

| Example | Name | LC rt | Method | (M + H)+ |
|---|---|---|---|---|
| Ex. 1-7 | (4-{4-[2-(5-Chloro-pyridin-2-ylamino)-pyrimidin-5-yl]-phenyl}-cyclohexyl)-acetic acid | 13 | D | 423.1 |

Example 2-1

(4-{4-[2-(3-Methoxyphenylamino)-thiazol-4-yl]-phenyl}-cyclohexyl)-acetic acid

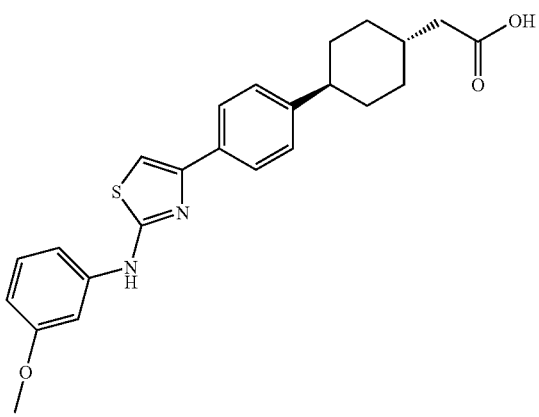 [SMILES: COc1cccc(Nc2nc(-c3ccc([C@H]4CC[C@H](CC(=O)O)CC4)cc3)cs2)c1]

A. {4-[4-(2-Bromoacetyl)-phenyl]-cyclohexyl}-acetic acid ethyl ester

To a solution of (4-phenylcyclohexyl)-acetic acid ethyl ester (10.0 g, 40.6 mmol) (patent WO2004 047755) in DCM (100 mL) at 0° C. is added AlCl$_3$ (9.94 g, 74 mmol) portionwise. After it is stirred at −1.8° C. for 10 min, bromoacetyl bromide (3.59 mL, 40.6 mmol) is added dropwise over 2 min. The reaction mixture is allowed to stir at −1.8° C. for 2 h. It is then poured slowly to water/ice mixture (200 mL) and stirred for 30 min. The mixture is extracted with DCM (2×50 mL). The organic phase is separated and washed with NaHCO$_3$ (3×100 mL), and brine (3×100 mL), dried with Na$_2$SO$_4$, concentrated and dried under high vacuum to give the title compound (12.8 g) as a yellow solid: 1H NMR (400 MHz, CHLOROFORM-d) δ ppm 1.05-1.17 (m, 2H) 1.20 (t, J=8.00 Hz, 3H) 1.39-1.51 (m, 2H) 1.56-1.68 (m, 1H) 1.76-1.87 (m, 4H) 2.18 (d, J=4.29 Hz, 2H) 2.48 (td, J=12.32, 2.65 Hz, 1H) 4.08 (q, J=7.24 Hz, 2H) 4.35 (s, 2H) 7.25 (d, J=8.34 Hz, 2H) 7.85 (d, J=8.59 Hz, 2H).

B. (4-{4-[2-(3-Methoxyphenylamino)-thiazol-4-yl]-phenyl}-cyclohexyl)-acetic acid ethyl ester To a solution of {4-[4-(2-bromoacetyl)-phenyl]-cyclohexyl}-acetic acid ethyl ester (100 mg, 0.272 mmol) in EtOH/THF (4:1 v/v, 5 mL) is added 3-methoxyphenylthiourea (99.6 mg, 0.272 mmol) and $Na_2CO_3$ (58 mg, 0.545 mmol). The reaction mixture is allowed to stir at 50° C. for 3 h. The reaction mixture is used directly in the next step: $(M+H)+$ 451.1.

C. (4-{4-[2-(3-Methoxyphenylamino)-thiazol-4-yl]-phenyl}-cyclohexyl)-acetic acid General Saponification Procedure To the reaction mixture of (4-{4-[2-(3-methoxyphenylamino)-thiazol-4-yl]-phenyl}-cyclohexyl)-acetic acid ethyl ester from step B is added LiOH (10% solution, 1 mL). It is then heated at 50° C. for 18 h. The mixture is then acidified with HCl solution (1N) to pH=5. The resulting solid is filtered and dried under high vacuum to give the title compound (26.8 mg) as a solid; $^1H$ NMR (400 MHz, DMSO-d6) δ ppm 0.96-1.07 (m, 2H) 1.31-1.43 (m, 2H) 1.50-1.52 (m, 1H) 1.58-1.64 (m, 1H) 1.71 (d, J=9.60 Hz, 4H) 2.03 (d, J=6.57 Hz, 2H) 2.27 (br. s., 1H) 3.67 (s, 3H) 6.43 (dd, J=7.83, 1.77 Hz, 1H) 7.03 (dd, J=7.20, 0.88 Hz, 1H) 7.09-7.20 (m, 4H) 7.44 (br. s., 1H) 7.70 (d, J=8.08 Hz, 2H) 10.13 (br. s., 1H); MS $(M+H)^+=423.2$.

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt.

The following compounds are prepared in analogous fashion:

| Example | Chemical Name | LC rt | Method | MS $(M + H)^+$ |
|---|---|---|---|---|
| 2-2 | (4-{4-[2-(3-Fluorophenylamino)-thiazol-4-yl]-phenyl}-cyclohexyl)-acetic acid | 1.53 | A | 411.2 |
| 2-3 | (4-{4-[2-(2-Chlorophenylamino)-thiazol-4-yl]-phenyl}-cyclohexyl)-acetic acid | 1.65 | A | 427.1 |
| 2-4 | (4-{4-[2-(3-Cyanophenylamino)-thiazol-4-yl]-phenyl}-cyclohexyl)-acetic acid | 1.41 | A | 418.1 |
| 2-5 | (4-{4-[2-(3-Trifluoromethylphenylamino)-thiazol-4-yl]-phenyl}-cyclohexyl)-acetic acid | 1.59 | A | 461.1 |

Example 2-6

(4-{4-[2-(3-Fluorophenylamino)-thiazol-4-yl]-phenyl}-cyclohexyl)-acetic acid

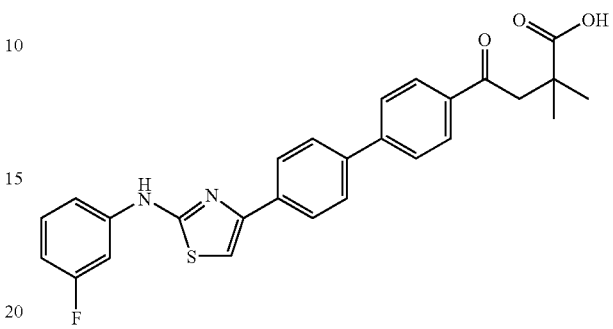

A. [4-(4-Bromophenyl)-thiazol-2-yl]-(3-fluorophenyl)-amine

The title compound is prepared analogously to Example 2-1 step B using 2-bromo-1-(4-bromophenyl)-ethanone and 3-fluorophenylthiourea: $(M+H)+350.9$.

B. 2,2-Dimethyl-4-oxo-4-[4-(4,4,5,5-tetramethyl-[1,3,2]dioxaborolan-2-yl)-phenyl]-butyric acid To a microwave vial is added 4-(4-bromophenyl)-2,2-dimethyl-4-oxo-butyric acid (150 mg, 0.526 mmol), bis(pinacolato)diboron (160 mg, 0.631 mmol), KOAc (155 mg, 1.58 mmol) and $PdCl_2dppf\ CH_2Cl_2$ (13 mg, 0.015 mmol). Then DME (2 mL) is added and the mixture is sparged with nitrogen for 2 min. The vial is then sealed and heated in a microwave at 120° C. for 20 min. The reaction mixture is then used directly in the next step: $(M+H)+333.1$.

C. (4-{4-[2-(3-Fluorophenylamino)-thiazol-4-yl]-phenyl}-cyclohexyl)-acetic acid

To a microwave vial is added [4-(4-bromophenyl)-thiazol-2-yl]-(3-fluorophenyl)-amine (92 mg, 0.26 mmol), 2,2-dimethyl-4-oxo-4-[4-(4,4,5,5-tetramethyl-[1,3,2]dioxaborolan-2-yl)-phenyl]-butyric acid (half of the crude from last step), sodium carbonate (2M solution, 0.526 mL) and resin bound $Pd(PPh_3)_4$ (130 mg, 0.013 mmol). The reaction mixture is sparged with nitrogen for 2 min and then heated in a microwave at 120° C. for 20 min. The resin is then filtered off and the filtrate is concentrated. The residue is titrate with ether. The resulting yellow solid is purified by reverse-phase preparative HPLC to give the title compound: 1H NMR (400 MHz, DMSO-D6) δ ppm 1.24 (s, 6H), 2.49 (d, J=3.54 Hz, 4H), 3.34 (s, 8H), 6.73-6.82 (m, 1H), 7.05 (s, 2H), 7.17 (s, 3H), 7.33 (s, 2H), 7.35-7.40 (m, 2H), 7.50 (s, 1H), 7.81-7.90 (m, 5H), 8.04 (dd, J=8.34, 2.53 Hz, 4H), 10.56 (s, 1H); $(M+H)^+=475.0$.

The following compounds are prepared in analogous fashion:

| Example | Chemical Name | LC rt | Method | MS (M + H)+ |
|---|---|---|---|---|
| 2-7 | 3-{4'-[2-(3-Fluorophenylamino)-thiazol-4-yl]-biphenyl-4-yl}-propionic acid | 1.42 | A | 419.1 |
| 2-8 | {4'-[2-(3-Fluorophenylamino)-thiazol-4-yl]-biphenyl-4-yl}-acetic acid | 1.35 | A | 405.1 |

Example 3-1

(4-{4-[2-(3-Chlorophenylamino)-oxazol-5-yl]-phenyl}-cyclohexyl)-acetic acid

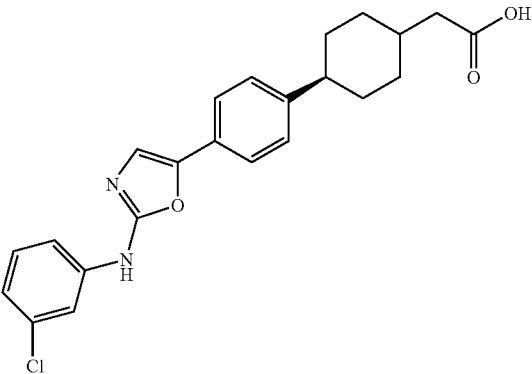

A. {4-[4-(2-Azidoacetyl)-phenyl]-cyclohexyl}-acetic acid ethyl ester

To a solution of {4-[4-(2-bromoacetyl)-phenyl]-cyclohexyl}-acetic acid ethyl ester (166 mg, 0.451 mmol) in acetone/water (4:1, v/v, 5 mL) is added NaN$_3$ (44 mg, 0.676 mmol) and the mixture is stirred at ambient temperature for 2 h. Water (10 mL) is added and EtOAc is used to extract. The organic phase is dried with MgSO$_4$, concentrated, and dried under high vacuum to give the title compound (154 mg): 1H NMR (400 MHz, CHLOROFORM-d) δ ppm 1.05-1.16 (m, 2H) 1.20 (t, J=7.07 Hz, 3H) 1.40-1.49 (m, 2H) 1.84 (d, J=10.11 Hz, 4H) 1.76-1.87 (m, 1H) 2.17 (d, J=6.82 Hz, 2H) 2.48 (tt, J=112.25, 3.03 Hz, 1H) 4.08 (q, J=7.16 Hz, 2H) 4.45 (s, 2H) 7.25 (d, J=8.34 Hz, 2H) 7.76 (d, J=8.34 Hz, 2H).

B. (4-{4-[2-(3-Chlorophenylamino)-oxazol-5-yl]-phenyl}-cyclohexyl)-acetic acid ethyl ester To a solution of {4-[4-(2-azidoacetyl)-phenyl]-cyclohexyl}-acetic acid ethyl ester (154 mg, 0.967 mmol) in 1,4-dioxane (5 mL) is added triphenylphosphine (122 mg, 0.967 mmol) and 1-chloro-3-isothiocyanatobenzene (0.051 mL, 0.389 mmol). The reaction mixture is then heated at 90° C. for 30 min. Water (10 mL) is added and EtOAc (20 mL) is used to extract. The organic phase is washed with brine (1×15 mL), dried with MgSO$_4$, and concentrated to give the title compound (109 mg) as an off-white solid: 1H NMR (400 MHz, DMSO-d6) δ ppm 1.19 (t, J=7.20 Hz, 3H) 1.12-1.19 (m, 2H) 1.43-1.52 (m, 2H) 1.81 (d, J=10.61 Hz, 4H) 1.73-1.84 (m, 1H) 2.23 (d, J=6.82 Hz, 2H) 4.07 (q, J=7.07 Hz, 2H) 6.99 (ddd, J=7.83, 2.02, 0.76 Hz, 1H) 7.28-7.36 (m, 3H) 7.41 (s, 1H) 7.47-7.53 (m, 3H) 7.85 (t, J=2.02 Hz, 1H) 10.52 (s, 1H); (M+H)+439.2.

C. (4-{4-[2-(3-Chlorophenylamino)-oxazol-5-yl]-phenyl}-cyclohexyl)-acetic acid

To a solution of (4-{4-[2-(3-Chlorophenylamino)-oxazol-5-yl]-phenyl}-cyclohexyl)-acetic acid ethyl ester (0.10 g) in 6 mL THF/water (2:1) was added 2 mL of a 10% aqueous LiOH solution. The reaction mixture was then heated to 150° C. under microwave heating for 20 min. Acidification with concentrated HCl afforded a precipitate which was filtered to afford the title compound: $^1$H NMR (400 MHz, DMSO-d6) δ ppm 1.14-1.25 (m, 2H) 1.48-1.60 (m, 2H) 1.76-1.83 (m, 1H) 1.86-1.94 (m, 4H) 2.21 (d, J=7.07 Hz, 2H) 7.06 (dd, J=8.21, 1.64 Hz, 1H) 7.34-7.43 (m, 3H) (s, 1H) 7.53-7.59 (m, 3H) 7.91 (t, J=2.02 Hz, 1H) 10.59 (s, 1H) 12.03 (br. s., 1H); MS (M+H)+=411.1.

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt.

The following compounds are prepared in analogous fashion:

| Example | Chemical Name | LC rt | Method | MS (M + H)+ |
|---|---|---|---|---|
| 3-2 | (4-{4-[2-(4-Chlorophenylamino)-oxazol-5-yl]-phenyl}-cyclohexyl)-acetic acid | 1.57 | A | 411.2 |
| 3-3 | (4-{4-[2-(4-Methoxyphenylamino)-oxazol-5-yl]-phenyl}-cyclohexyl)-acetic acid | 1.40 | A | 407.2 |
| 3-4 | (4-{4-[2-(2-Fluorophenylamino)-oxazol-5-yl]-phenyl}-cyclohexyl)-acetic acid | 1.40 | A | 359.1 |
| 3-5 | {4-[4-(2-Phenylaminooxazol-5-yl)-phenyl]-cyclohexyl}-acetic acid | 1.37 | A | 377.2 |
| 3-6 | (4-{4-[2-(3-Fluorophenylamino)-oxazol-5-yl]-phenyl}-cyclohexyl)-acetic acid | 1.42 | A | 395.2 |
| 3-7 | (4-{4-[2-(2-Chlorophenylamino)-oxazol-5-yl]-phenyl}-cyclohexyl)-acetic acid | 1.51 | A | 410.9 |
| 3-8 | (4-{4-[2-(3-Cyanophenylamino)-oxazol-5-yl]-phenyl}-cyclohexyl)-acetic acid | 1.34 | A | 402.1 |
| 3-9 | {4-[4-(2-Cyclohexylaminooxazol-5-yl)-phenyl]-cyclohexyl}-acetic acid | 1.4 | A | 383.0 |

| Example | Chemical Name | LC rt | Method | MS (M + H)+ |
|---|---|---|---|---|
| 3-10 | (4-{4-[2-(3,4-Dichlorophenylamino)-oxazol-5-yl]-phenyl}-cyclohexyl)-acetic acid | 1.58 | A | 445.1 |
| 3-11 | (4-{4-[2-(3-Chloro-4-fluorophenylamino)-oxazol-5-yl]-phenyl}-cyclohexyl)-acetic acid | 1.50 | A | 429.1 |
| 3-12 | (4-{4-[2-(4-Chloro-3-trifluoromethylphenylamino)-oxazol-5-yl]-phenyl}-cyclohexyl)-acetic acid | 1.61 | A | 479.1 |
| 3-13 | (4-{4-[2-(3,5-Difluorophenylamino)-oxazol-5-yl]-phenyl}-cyclohexyl)-acetic acid | 1.48 | A | 412.1 |
| 3-14 | (4-{4-[2-(3,5-Dichlorophenylamino)-oxazol-5-yl]-phenyl}-cyclohexyl)-acetic acid | 1.61 | A | 445.0 |
| 3-15 | (4-{4-[2-(2-Chloro-4-trifluoromethylphenylamino)-oxazol-5-yl]-phenyl}-cyclohexyl)-acetic acid | 1.62 | A | 479.0 |
| 3-16 | (4-{4-[2-(2-Trifluoromethylphenylamino)-oxazol-5-yl]-phenyl}-cyclohexyl)-acetic acid | 1.50 | A | 445.2 |
| 3-17 | (4-{4-[2-(3-Fluoro-4-methylphenylamino)-oxazol-5-yl]-phenyl}-cyclohexyl)-acetic acid | 1.44 | A | 409.2 |
| 3-18 | {4-[4-(2-p-Tolylaminooxazol-5-yl)-phenyl]-cyclohexyl}-acetic acid | 1.40 | A | 391.2 |
| 3-19 | (4-{4-[2-(3-Chloro-4-methylphenylamino)-oxazol-5-yl]-phenyl}-cyclohexyl)-acetic acid | 1.54 | A | 425.1 |

Example 3-20

4-(4-{4-[2-(3-Chlorophenylamino)-oxazol-5-yl]-phenyl}-cyclohexyl)-butyric acid

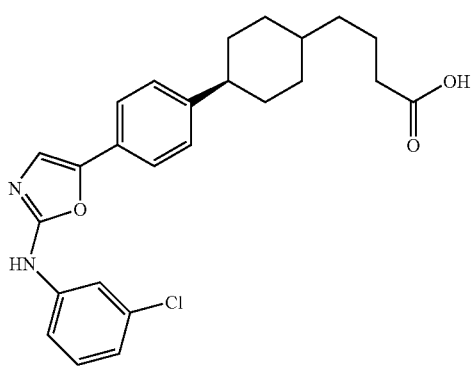

A. (4-{4-[2-(3-Chlorophenylamino)-oxazol-5-yl]-phenyl}-cyclohexyl)-acetaldehyde

To a solution of (4-{4-[2-(3-Chlorophenylamino)-oxazol-5-yl]-phenyl}-cyclohexyl)-acetic acid ethyl ester (500 mg, 1.14 mmol) in DCM (20 mL) at −78° C. is added DIBAL-H (1 M in toluene, 2.14 mL, 2.14 mmol) and the mixture is allowed to stir at −78° C. for 2 h. Methanol (3 mL) is added to quench the reaction. The reaction mixture is then poured in ice and Rochelle's salt (4 g). Water (20 mL) is added and the mixture is extracted with EtOAc (3×30 mL). The organic phase is washed with brine (3×30 mL), dried with $Na_2SO_4$ and concentrated to give the title compound (253 mg) as a white solid: (M+H)+395.2.

B. (E)-4-(4-{4-[2-(3-Chlorophenylamino)-oxazol-5-yl]-phenyl}-cyclohexyl)-but-2-enoic acid benzyl ester To a mixture of (benzyloxycarbonylmethyl)-triphenylphosphionium bromide (315 mg, 0.642 mmol) in THF (6 mL) at 0° C. is added NaH (60% in mineral oil, 27 mg, 0.642 mmol) and the suspension is allowed to stir at 0° C. for 30 min. (4-{4-[2-(3-Chlorophenylamino)-oxazol-5-yl]-phenyl}-cyclohexyl)-acetaldehyde (253 mg, 0.642 mmol) in THF (4 mL) is added dropwise. The reaction mixture is then stirred a 0° C. for 30 min and the at ambient temperature for 18 h. Water (10 mL) and HCl solution (1N, 15 mL) is added, and the reaction mixture is extracted with EtOAc (3×15 mL). The organic phase is washed with water (1×5 mL), brine (3×20 mL), dried and concentrated to give the title compound (279 mg) as an off-white solid: 1H NMR (400 MHz, CHLOROFORM-d) δ ppm 1.02-1.14 (m, 2H) 1.34-1.49 (m, 3H) 1.59-1.73 (m, 1H) 1.80-1.87 (m, 3H) 2.11 (t, J=8.00 Hz, 2H) 2.46 (ddd, J=11.68, 9.16, 2.91 Hz, 1H) 5.11 (s, 2H) 5.82 (d, J=15.66 Hz, 1H) 6.90-6.99 (m, 1H) 7.14-7.17 (d, 8.08 Hz, 2H) 7.24-7.28 (m, 3H) 7.28-7.32 (m, 6H) 7.40 (d, J=8.08 Hz, 1H) 7.49 (s, 1H); (M+H)+527.2.

C. 4-(4-{4-[2-(3-Chlorophenylamino)-oxazol-5-yl]-phenyl}-cyclohexyl)-butyric acid To a solution of (E)-4-(4-{4-[2-(3-chlorophenylamino)-oxazol-5-yl]-phenyl}-cyclohexyl)-but-2-enoic acid benzyl ester (139 mg, 0.283 mmol) in EtOAc/EtOH (5:1 v/v, 6 mL) is added Pd(OH)$_2$ (100 mg) the mixture is stirred in an hydrogenated at 1 atm for 72 h. The catalyst is filtered and washed with EtOAc. The filtrated is then concentrated and dried under high vacuum to give the title compound (107 mg) as a white solid: 1H NMR (400 MHz, DMSO-d6) δ ppm 0.98-1.09 (m, 2H) 1.18-1.25 (m, 2H) 1.39-1.48 (m, 2H) 1.49-1.57 (m, 2H) 1.82 (d, J=10.11 Hz, 4H) 1.74-1.85 (m, 1H) 2.18 (t, J=7-33 Hz, 2H) 6.99 (ddd, J=7.96, 2.02, 0.88 Hz, 1H) 7.28-7.33 (m, 3H) 7.40 (s, 1H) 7.47-7.52 (m, 3H) 7.85 (t, J=2.02 Hz, 1H); (M+H)$^+$=439.0.

Example 3-21

(E)-4-(4-{4-[2-(3-Chlorophenylamino)-oxazol-5-yl]-phenyl}-cyclohexyl)-but-2-enoic acid

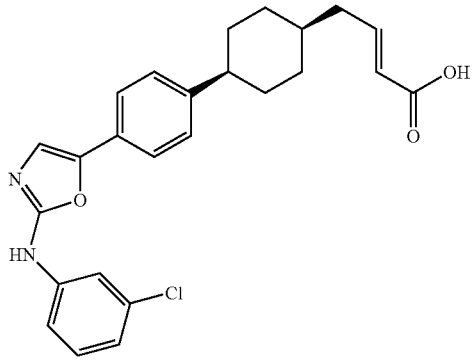 [SMILES: O=C(O)/C=C/C[C@H]1CC[C@@H](c2ccc(-c3cnc(Nc4cccc(Cl)c4)o3)cc2)CC1]

To a solution of (E)-4-(4-{4-[2-(3-chlorophenylamino)-oxazol-5-yl]-phenyl}-cyclohexyl)-but-2-enoic acid benzyl ester (139 mg, 0.283 mmol) in 3 mL of THF/water (2:1) was added 1 mL of 10% aqueous LiOH. The homogeneous reaction was allowed to stir at 50° C. overnight. Acidification with concentrated HCl afforded a precipitate which was filtered and then purified by reverse-phase preparative HPLC to afford the title compound: 1H NMR (400 MHz, DMSO-d6) δ ppm 0.98-1.09 (m, 2H) 1.41 (td, J=11.62, 3.28 Hz, 3H) 1.71-1.78 (m, 4H) 2.07 (t, J=6.82 Hz, 2H) 5.72 (d, J=15.41 Hz, 1H) 6.76 (ddd, J=15.47, 7.64, 7.45 Hz, 1H) 6.92 (ddd, J=7.89, 1.96, 0.76 Hz, 1H) 7.21-7.28 (m, 2H) 7.23 (d, J=8.34 Hz, 1H) 7.34 (s, 1H) 7.41-7.45 (m, 3H) 7.78 (t, J=2.02 Hz, 1H) 10.47 (br. s., 1H); (M+H)+437.2.

Example 3-22

3-[2-(4-{4-[2-(3-Chlorophenylamino)-oxazol-5-yl]-phenyl}-cyclohexyl)-acetylamino]-propionic acid

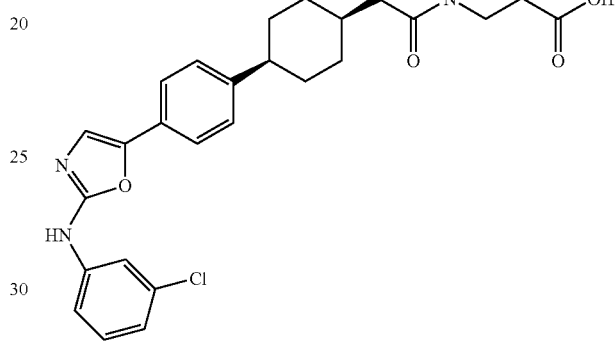

A. 3-[2-(4-{4-[2-(3-Chlorophenylamino)-oxazol-5-yl]-phenyl}-cyclohexyl)-acetylamino]-propionic acid ethyl ester To a solution of 3-aminopropionic acid ethyl ester (41 mg, 0.268 mmol) and Et3N (0.082 mL, 0.730 mmol) is added a solution of (4-{4-[2-(3-Chlorophenylamino)-oxazol-5-yl]-phenyl}-cyclohexyl)-acetic acid (100 mg, 0.243 mmol) in DMF (4 mL), HATU (102 mg, 0.268 mmol) and iPr$_2$NEt (0.127 mL, 0.73 mmol). The reaction mixture is allowed to stir at ambient temperature for 18 h. Water is added and EtOAc is used to extract. The organic layer is washed with brine, dried with Na$_2$SO$_4$ and concentrated to give the title compound (140 mg) as a tan solid: 1H NMR (400 MHz, DMSO-d6) δ ppm 1.02-1.13 (m, 2H) 1.18 (t, J=7.07 Hz, 3H) 1.38-1.50 (m, 2H) 1.71 (dd, J=7.71, 4.17 Hz, 1H) 1.78 (t, J=12.63 Hz, 4H) 1.98 (d, J=6.57 Hz, 2H) 2.44 (t, J=6.82 Hz, 2H) 3.25-3.28 (m, 2H) 4.06 (q, J=7.07 Hz, 2H) 6.99 (ddd, J=7.89, 1.96, 1.01 Hz, 1H) 7.27-7.35 (m, 1H) 7.29 (d, J=8.59 Hz, 2H) 7.40 (s, 1H) 7.50 (d, J=8.34 Hz, 1H) 7.47-7.52 (m, 1H) 7.85 (t, J=2.02 Hz, 1H) 7.88 (t, J=5.81 Hz, 1H) 10.52 (s, 1H); (M+H)+510.2.

B. 3-[2-(4-{4-[2-(3-Chlorophenylamino)-oxazol-5-yl]-phenyl}-cyclohexyl)-acetylamino]-propionic acid The title compound is prepared in analogous fashion to the procedures described above: 1H NMR (400 MHz, DMSO-d6) δ ppm 0.98-1.10 (m, 2H) 1.35-1.46 (m, 2H) 1.63-1.70 (m, 1H) 1.71-1.79 (m, 4H) 1.95 (d, J=6.82 Hz, 2H) 2.30 (t, J=6.95 Hz, 2H) 2.38-2.44 (m, 1H) 3.20 (d, J=19.45 Hz, 1H) 3.20 (d, J=5.81 Hz, 1H) 6.96 (ddd, J=7.96, 2.02, 0.88 Hz, 1H) 7.27 (dd, J=9.85, 8.34 Hz, 3H) 7.38 (s, 1H) 7.44-7.49 (m, 3H) 7.82 (t, J=2.02 Hz, 2H) (M+H)=482.2.

Example 3-23

{[2-(4-{4-[2-(3-Chlorophenylamino)-oxazol-5-yl]-phenyl}-cyclohexyl)-acetyl]-methyl-amino}-acetic acid

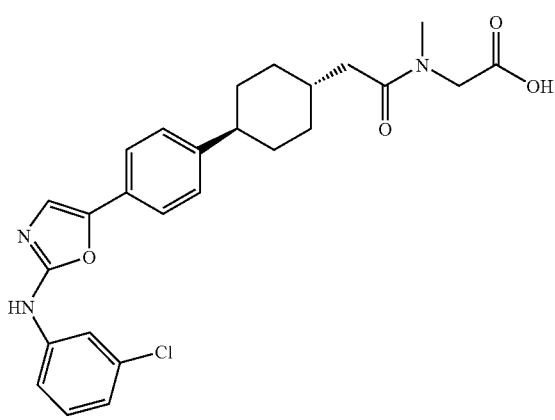 [SMILES: CN(CC(=O)O)C(=O)C[C@H]1CC[C@H](c2ccc(-c3cnc(Nc4cccc(Cl)c4)o3)cc2)CC1]

The title compound is prepared in analogous fashion to Example 3-22 using methylamino-acetic acid ethyl ester: 1H NMR (400 MHz, DMSO-d6) δ ppm 0.90-0.99 (m, 2H), 1.24-1.36 (m, 2H), 1.60-1.70 (m, 5H), 1.96 and 2.11 (d rotamers, J=6.57 Hz and 6.82 Hz, 2H), 2.64 and 2.86 (s rotamers, 3H), 3.78 and 3.80 (br.s. and s rotamers, 2H), 6.84 (dt, J=7.83, 1.01 Hz, 1H), 7.12-7.20 (m, 3H), 7.26 (d, J=1.52 Hz, 1H), 7.32-7.37 (m, 3H), 7.70 (t, J=2.02 Hz, 1H), 10.40 (br. s., 1H); (M+H)⁺=482.2.

Example 3-24

{4'-[2-(3-Chlorophenylamino)-oxazol-5-yl]-biphenyl-4-yl}-acetic acid

The title compound is prepared analogously to Example 3-1 using 2-bromo-1-(4-bromophenyl)-ethanone and [4-(4,4,5,5-tetramethyl-[1,3,2]dioxaborolan-2-yl)-phenyl]-acetic acid as starting materials: 1H NMR (400 MHz, DMSO-d6) δ ppm 3.80 (s, 2H) 7.19 (d, J=7.83 Hz, 1H) 7.50-7.58 (m, 3H) 7.72-7.76 (m, 2H) 7.83-7.90 (m, 4H) 7.95 (m, 2H) 8.05 (t, J=2.15 Hz, 1H) 10.78 (s, 1H) 12.51 (br. s., 1H); (M+H)⁺=405.1.

The following compounds are prepared in similar fashion:

| Example | Chemical Name | LC rt | Method | MS (M + H)⁺ |
|---|---|---|---|---|
| 3-25 | 3-{4'-[2-(3-Chlorophenylamino)-oxazol-5-yl]-biphenyl-4-yl}-propionic acid | 0.84 | B | 419.0 |
| 3-26 | 4-{4'-[2-(3-Chlorophenylamino)-oxazol-5-yl]-biphenyl-4-yl}-2,2-dimethyl-4-oxo-butyric acid | 1.02 | B | 475.0 |
| 3-27 | 4-{4'-[2-(3-Chlorophenylamino)-oxazol-5-yl]-biphenyl-4-yl}-4-oxo-butyric acid | 1.36 | A | 445.0 |
| 3-28 | 4-{4'-[2-(3-Chlorophenylamino)-oxazol-5-yl]-biphenyl-4-carbonyl}-cyclohexanecarboxylic acid | 1.13 | C | 501.1 |

Example 3-29

(4-{4-[2-(3-Chlorophenylamino)-oxazol-5-yl]-phenyl}-3,6-dihydro-2H-pyridin-1-yl)-oxo-acetic acid

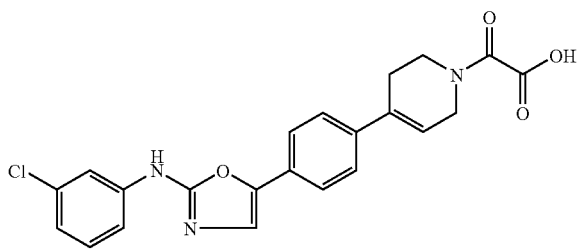 [SMILES: O=C(O)C(=O)N1CC=C(c2ccc(-c3cnc(Nc4cccc(Cl)c4)o3)cc2)CC1]

A. 4-{4-[2-(3-Chlorophenylamino)-oxazol-5-yl]-phenyl}-3,6-dihydro-2H-pyridine-1-carboxylic acid tert-butyl ester Preparation of -(4,4,5,5-tetramethyl-[1,3,2]dioxaborolan-2-yl)-3,6-dihydro-2H-pyridine-1-carboxylic acid tert-butyl ester has been described [Tet. Lett. 41-(19), 3705-3708, 2000]. The boronate ester (1.1 g, 3.6 mmol, 1.5 equiv) and [5-(4-bromo-phenyl)-oxazol-2-yl]-(3-chloro-phenyl)-amine (0.84 g, 2.4 mmol, 1.0 equiv) were dissolved in 12 mL DME and then charged with 3 mL of a 2M $Na_2CO_3$ solution. $Pd(Ph_3)_4$ on polystyrene resin (0.72 g, 0.072 mmol) was added, and the suspension was sparged with nitrogen for 10 min, then heated to 100° C. overnight. The reaction was then filtered to remove catalyst, and following solvent removal the product was triturated with hexanes and ether to afford the title compound: (M+H)+452.1.

B. (3-Chlorophenyl)-{5-[4-(1,2,3,6-tetrahydro-pyridin-4-yl)-phenyl]-oxazol-2-yl}-amine To a solution of 4-{4-[2-(3-chlorophenylamino)-oxazol-5-yl]-phenyl}-3,6-dihydro-2H-pyridine-1-carboxylic acid tert-butyl ester (2.5 g, 5.5 mmol) in MeOH (1 mL) is added 4M HCl in dioxane (3 mL) and the mixture is stirred at RT for 2 h. It is concentrated and used in the next step as the bis HCl salt: (M+H)+352.1.

C. (4-{4-[2-(3-Chlorophenylamino)-oxazol-5-yl]-phenyl}-3,6-dihydro-2H-pyridin-1-yl)-oxo-acetic acid ethyl ester To a solution of (3-chlorophenyl)-{5-[4-(1,2,3,6-tetrahydro-pyridin-4-yl)-phenyl]-oxazol-2-yl}-amine bis HCl salt (50 mg, 0.12 mmol) in DCM (1 mL) at 0° C. is added DIEA (0.052 mL, 0.3 mmol) and after stirring for 5 min, ethyl chlorooxoacetate (0.016 mL, 0.14 mmol) is added dropwise. The mixture is stirred for 2 h and the mixture is purified by RP-HPLC to give the title compound: $^1$H NMR (400 MHz, DMSO-D6) δ 1.30 (q, J=7.07 Hz, 3H) 2.58 (m, 2H) 3.55-3.90 (m, 2H) 4.07-4.20 (m, 1H) 4.32 (m, 2H) 6.21-6.29 (m, 1H) 7.00 (dd, J=7.45, 1.64 Hz, 1H) 7.34 (t, J=8.08 Hz, 1H) 7.47-7.60 (m, 6H) 7.86 (t, J=2.02 Hz, 1H); (M+H)+452.1.

D. (4-{4-[2-(3-Chlorophenylamino)-oxazol-5-yl]-phenyl}-3,6-dihydro-2H-pyridin-1-yl)-oxo-acetic acid Using the saponification procedures described above, the title compound is obtained: $^1$H NMR (400 MHz, DMSO-d6) δ 3.37 (br. s., 2H) 3.64 (d, J=15.92 Hz, 2H) 4.08 (br.s., 2H) 6.30 (br. s., 1H) 7.05 (dd, J=7.83, 2.02 Hz, 1H) 7.39 (t, J=8.08 Hz, 1H) 7.53-7.60 (m, 4H) 7.60-7.64 (m, 2H) 7.92 (t, J=1.89 Hz, 1H) 10.73 (d, J=4.04 Hz, 1H); (M+H)+=424.1.

Example 3-30

4-{4-[2-(3-Chloro-phenylamino)-oxazol-5-yl]-phenyl}-3,6-dihydro-2H-pyridine-1-sulfonic acid amide

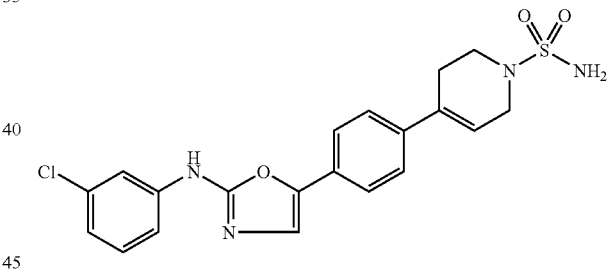

The title compound is prepared from (3-chlorophenyl)-{5-[4-(1,2,3,6-tetrahydro-pyridin-4-yl)-phenyl]-oxazol-2-yl}-amine bis HCl salt in analogous fashion using N-Boc chlorosulfonamide followed by TFA-mediated deprotection: $^1$H NMR (400 MHz, DMSO-d6) δ 2.55 (br. s., 2H) 3.15 (t, J=5.56 Hz, 2H) 3.65 (d, J=2.78 Hz, 2H) 6.22 (t, J=3.28 Hz, 1H) 6.92 (dd, J=7.83, 1.52 Hz, 1H) 7.26 (t, J=8.08 Hz, 1H) 7.39-7.53 (m, 7H) 7.79 (t, J=2.02 Hz, 1H); (M+H)+431.1.

Using the appropriate acylating agent, the following compounds may also be prepared:

| Example | Chemical Name | LC rt | Method | MS (M + H)+ |
|---|---|---|---|---|
| 3-31 | 4-{4-[2-(3-Chloro-phenylamino)-oxazol-5-yl]-phenyl}-3,6-dihydro-2H-pyridine-1-sulfonic acid amide-N-carboxylic acid tert-butyl ester | 1.55 | A | 531.2 |
| 3-32 | 4-(4-{4-[2-(3-Chloro-phenylamino)-oxazol-5-yl]-phenyl}-3,6-dihydro-2H-pyridin-1-yl)-2,2-dimethyl-4-oxo-butyric acid | 1.37 | A | 480.0 |

| Example | Chemical Name | LC rt | Method | MS (M + H)+ |
|---|---|---|---|---|
| 3-33 | 4-(4-{4-[2-(3-Chloro-phenylamino)-oxazol-5-yl]-phenyl}-3,6-dihydro-2H-pyridin-1-yl)-4-oxo-butyric acid | 1.19 | A | 452.0 |
| 3-34 | 2-(4-{4-[2-(3-Chloro-phenylamino)-oxazol-5-yl]-phenyl}-3,6-dihydro-2H-pyridine-1-carbonyl)-benzoic acid | 1.23 | A | 500.1 |

Example 3-35

(1R,2R)-2-{4'-[2-(3-Chlorophenylamino)-oxazol-5-yl]-biphenyl-4-carbonyl}-cyclohexanecarboxylic acid

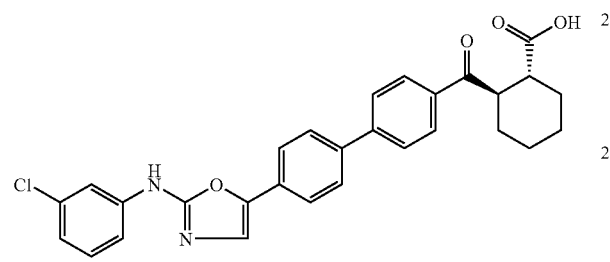

A. (3-Chloro-phenyl)-{5-[4-(4,4,5,5-tetramethyl-[1,3,2]dioxaborolan-2-yl)-phenyl]-oxazol-2-yl}-amine The title compound is prepared from [5-(4-bromophenyl)-oxazol-2-yl]-(3-chlorophenyl)-amine using bis(pinacolato)diboron, KOAc, and PdCl₂dppf CH₂Cl₂ in DME at 120° C. for 20 min under microwave heating. The reaction mixture is then used directly in the next step: (M+H)+397.1.

B. (1R,2R)-2-{4'-[2-(3-Chlorophenylamino)-oxazol-5-yl]-biphenyl-4-carbonyl}-cyclohexanecarboxylic acid Using (1R,2R)-2-(4-Bromo-benzoyl)-cyclohexanecarboxylic acid, the title compound may be prepared: ¹H NMR (400 MHz, DMSO-d6) δ 1.16-1.28 (m, 1H) 1.36-1.58 (m, 3H) 1.77-1.91 (m, 2H) 2.01 (d, J=10.61 Hz, 1H) 2.17 (dd, J=12.25, 2.91 Hz, 1H) 2.75 (dd, J=11.75, 2.91 Hz, 1H) 3.66-3.75 (m, 1H) 7.08 (dd, J=7.83, 1.26 Hz, 1H) 7.42 (t, J=8.08 Hz, 1H) 7.59 (dd, J=8.34, 1.26 Hz, 1H) 7.68 (s, 1H) 7.79 (d, J=8.34 Hz, 2H) 7.94 (t, J=8.59 Hz, 5H) 8.15 (d, J=8.59 Hz, 2H) 10.70 (br. s., 1H); (M+H)+=501.0.

The following compounds are prepared in analogous fashion:

| Example | Chemical Name | LC rt | Method | MS (M + H)+ |
|---|---|---|---|---|
| Ex. 3-36 | (trans)-2-{4'-[2-(3-Chlorophenylamino)-oxazol-5-yl]-biphenyl-4-carbonyl}-cyclohexanecarboxylic acid | 1.1 | B | 501.1 |
| Ex. 3-37 | (trans)-2-{4'-[2-(3-Chlorophenylamino)-oxazol-5-yl]-biphenyl-4-carbonyl}-cyclopentanecarboxylic acid | 1.52 | A | 487.0 |
| Ex-3-38 | (4-{4'-[2-(3-Chloro-phenylamino)-oxazol-5-yl]-biphenyl-4-yl}-cyclohexyl)-acetic acid | 1.22 | B | 487.1 |

Example 4-1

(4-{5-[6-(6-Trifluoromethyl-pyridin-3-ylamino)-pyridin-3-yl]-spirocyclohexylidenyl-1,1'-indanyl}-acetic acid

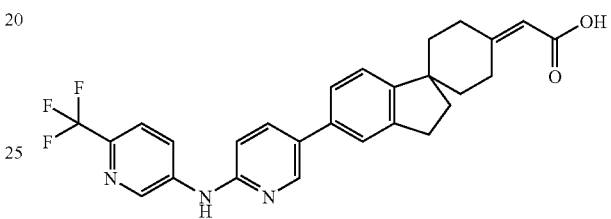

A. {4-[5-(4,4,5,5-tetramethyl-[1,3,2]dioxaborolan-2-yl)]-spirocyclohexylidenyl-1,1'-indanyl}-acetic acid methyl ester To a solution of (5-bromo-spirocyclohexylidenyl-1,1'-indanyl)-acetic acid methyl ester (reported in WO2004 047755, 6.9 g, 20.7 mmol, 1.0 equiv) in 35 mL dimethoxyethane was added bis(pinacolato)diboron (6.4 g, 24.8 mmol, 1.2 equiv), potassium acetate (5.0 g, 51.8 mmol, 2.5 equiv) and PdCl₂dppf (dichloromethane) complex (0.67 g, 0.83 mmol, 0.04 equiv). The reaction mixture was sparged with nitrogen for 10 minutes, then sealed and heated to 100° C. for 18 h. The reaction was cooled to room temperature, filtered, and concentrated in vacuo. Purification by flash chromatography (5-15% EtOAc in hexanes) afforded the title compound as a white solid: ¹H NMR (400 MHz, CDCl₃) δ 1.26 (s, 12H) 1.65-1.78 (m, 4H) 2.00-2.15 (m, 3H) 2.25 (m, 1H) 2.33 (m, 1H) 2.87 (t, J=7.33 Hz, 2H) 3.63 (s, 3H) 3.74 (m, 1H) 5.63 (s, 1H) 7.07 (d, J=7.58 Hz, 1H) 7.58 (dd, J=7.58, 0.76 Hz, 1H) 7.62 (s, 1H); (M+H)+383.2.

B. (5-Bromo-pyridin-2-yl)-(6-trifluoromethyl-pyridin-3-yl)-amine

A mixture of 5-amino-2-(trifluoromethyl)pyridine (0.5 g, 3.0 mmol, 1.0 equiv) and 5-bromo-2-fluoropyridine (0.47 mL, 4.6 mmol, 1.5 equiv) in 2 mL 1-butanol was charged with 0.15 mL of 4.0 M HCl (in dioxane) and heated to 150° C. via microwave heating. After cooling to room temperature, the reaction mixture was partitioned between ethyl acetate and saturated bicarbonate, and the organic extracts were washed with brine and dried over sodium sulphate. Purification of the crude product by flash chromatography afforded the title compound: ¹H NMR (400 MHz, CDCl₃) δ 6.63 (br. s., 1H) 6.67 (d, J=9.35 Hz, 1H) 7.56 (d, J=8.59 Hz, 1H) 7.62 (dd, J=8.84, 2.53 Hz, 1H) 8.22-8.66 (m, 2H) 8.57 (d, J=2.78 Hz, 1H); (M+H)+320.0.

C. (4-{5-[6-(6-Trifluoromethyl-pyridin-3-ylamino)-pyridin-3-yl]-spirocyclohexylidenyl-1,1'-indanyl}-acetic acid methyl ester A microwave vial was charged with 5-Bromopyridin-2-yl)-(6-trifluoromethyl-pyridin-3-yl)-amine (0.23 g, 0.71 mmol, 1.0 equiv) and {4-[5-(4,4,5,5-tetramethyl-[1,3,2]dioxaborolan-2-yl)]-spirocyclohexylidenyl-1,1'-indanyl}-acetic acid methyl ester (0.30 g, 0.78 mmol, 1.0 equiv) in 4 mL dimethoxyethane. To this solution was added 2M Na2CO3 (0.89 mL, 2.5 equiv) followed by PdCl₂dppf (dichloromethane) complex (0.023 g, 0.028 mmol, 0.04 equiv). The mixture was sparged with nitrogen for 5 minutes and then heated to 150° C. for 30 min. The reaction was partitioned between EtOAc and water, and the organic extracts were washed with brine and dried over magnesium sulphate. Purification of the crude product by flash chromatography afforded the title compound: ¹H NMR (400 MHz, CDCl₃) δ 1.69-1.80 (m, 4H) 2.07-2.19 (m, 3H) 2.24-2.32 (m, 1H) 2.37 (m, 1H) 2.94 (t, J=7.33 Hz, 2H) 3.65 (s, 3H) 3.77 (m, 1H) 5.66 (s, 1H) 6.84 (d, J=8.59 Hz, 1H) 6.90 (br. s., 1H) 7.13 (d, J=7.83 Hz, 1H) 7.29 (dd, J=7.96, 1.64 Hz, 1H) 7.33 (s, 1H) 7.57 (d, J=8.59 Hz, 1H) 7.75 (dd, J=8.59, 2.53 Hz, 1H) 8.29 (dd, J=8.72, 2.15 Hz, 1H) 8.42 (d, J=2.02 Hz, 1H) 8.60 (d, J=2.53 Hz, 1H); (M+H)+494.2.

D. (4-{5-[6-(6-Trifluoromethyl-pyridin-3-ylamino)-pyridin-3-yl]-spirocyclohexylidenyl-1,1'-indanyl}-acetic acid (4-{5-[5-(6-Trifluoromethyl-pyridin-3-ylamino)-pyridin-2-yl]-spirocyclohexylidenyl-1,1'-indanyl}-acetic acid methyl ester (0.36 g, 0.73 mmol, 1.0 equiv) was dissolved in 3 mL THF/MeOH (2:1) and charged with 1 mL 10% aqueous LiOH. The reaction was stirred at 60° C. for 3 hours. The volatile organics were removed, and then the pH was adjusted to pH 1 using a few drops of concentrated HCl. The resulting precipitate was filtered and dried overnight to afford the title compound: ¹H NMR (400 MHz, DMS-d6) δ 1.56-1.71 (m, 4H) 2.08 (dd, J=14.91, 1.77 Hz, 2H) 2.07 (5, 1H) 2.26 (dd, J=3.54, 1.77 Hz, 1H) 2.34 (dd, J=13.14, 8.84 Hz, 1H) 2.88 (t, J=7.33 Hz, 2H) 3.68 (d, J=13.89 Hz, 1H) 5.60 (s, 1H) 6.95 (d, J=8.84 Hz, 1H) 7.20 (d, J=7.83 Hz, 1H) 7.36 (d, J=7.83 Hz, 1H) 7.42 (s, 1H) 7.72 (d, J=8.84 Hz, 1H) 7.89 (dd, J=8.84, 2.53 Hz, 1H) 8.46 (d, J=2.53 Hz, 1H) 8.50 (dd, J=8.84, 2.27 Hz, 1H) 8.84 (d, J=2.53 Hz, 1H) 9.79 (s, 1H); (M+H)+480.2.

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt.

Example 4-2

(4-{5-[6-(6-Trifluoromethyl-pyridin-3-ylamino)-pyridin-3-yl]-spirocyclohexyl-1,1'-indanyl}-acetic acid

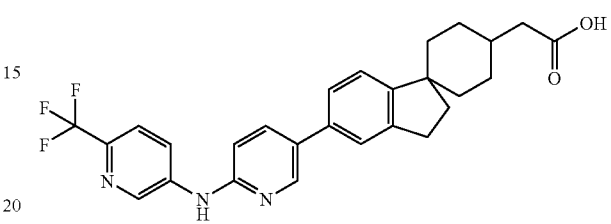

To a solution of (4-{5-[5-(6-Trifluoromethyl-pyridin-3-ylamino)-pyridin-2-yl]-spirocyclohexylidenyl-1,1'-indanyl}-acetic acid (0.15 g, 0.31 mmol, 1.0 equiv) in 5 mL EtOH was added 20 mg platinum oxide. The reaction vessel was then purged with hydrogen, and then stirred under balloon pressure overnight. The reaction was filtered through Celite and concentrated in vacuo. Purification by reverse-phase HPLC afforded two separable diastereomers (cis and trans): Diastereomer 1: ¹H NMR (400 MHz, DMSO-d6) δ 1.27 (m, 2H) 1.55-1.63 (m, 2H) 1.67-1.81 (m, 4H) 1.84 (br. s., 1H) 2.03 (t, J=7.33 Hz, 2H) 2.24 (d, J=6.82 Hz, 2H) 2.95 (t, J=7.45 Hz, 2H) 7.09 (d, J=8.59 Hz, 1H) 7.33 (d, J=7.83 Hz, 1H) 7.53 (s, 1H) 7.51 (d, J=7.83 Hz, 1H) 7.86 (d, J=8.84 Hz, 1H) 8.03 (dd, J=8.59, 2.53 Hz, 1H) 8.60 (d, J=2.02 Hz, 1H) 8.64 (dd, J=8.46, 2.15 Hz, 1H) 8.98 (d, J=2.53 Hz, 1H) 9.91 (s, 1H) Diastereomer 2: ¹H NMR (400 MHz, DMSO-d6) δ 1.20 (m, 2H) 1.25-1.35 (m, 2H) 1.43-1.57 (m, 4H) 1.72 (t, J=7.33 Hz, 2H) 1.80 (br. s., 1H) 2.17 (d, J=7.33 Hz, 2H) 2.66 (t, J=7.07 Hz, 2H) 6.80 (d, J=8.84 Hz, 1H) 7.24 (d, J=7.58 Hz, 2H) 7.19-7.26 (m, 1H) 7.57 (br. s., 1H) 7.75 (dd, J=8.59, 2.53 Hz, 1H) 8.31 (d, J=2.27 Hz, 1H) 8.35 (dd, J=8.84, 2.53 Hz, 1H) 8.69 (d, J=2.53 Hz, 1H) 9.63 (s, 1H); (M+H)+482.2.

Example 4-3

(4-{4-[6-(3-Chloro-phenylamino)-pyridin-3-yl]-phenyl}-cyclohexyl)-acetic acid

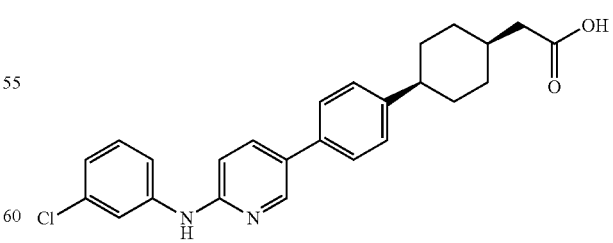

A. (5-Bromo-pyridin-2-yl)-(3-chlorophenyl)-amine

A 1-dram vial was charged with 2,5-dibromopyridine (0.5 g, 2.1 mmol, 1.0 equiv) and 3-chlorophenyl amine (0.89 mL, 8.4 mmol, 4 equiv). The neat reaction mixture was heated to 180° C. for 3 hours. The reaction was cooled, then purified by flash chromatography to afford the title compound. (M+H)+ 285.0.

B. (4-{4-[6-(3-Chloro-phenylamino)-pyridin-3-yl]-phenyl}-cyclohexyl)-acetic acid The title compound was synthesized using {(4-[4-(4,4,5,5-tetramethyl-[1,3,2]dioxaborolan-2-yl)-phenyl]-cyclohexyl}-acetic acid methyl ester and the procedures described above: $^1$H NMR (400 MHz, DMSO-d6) δ 1.30-1.36 (m, 1H) 1.65-1.78 (m, 1H) 1.85 (m, 5H) 1.89-1.97 (m, 1H) 2.00-2.11 (m, 1H) 2.53 (d, J=7.58 Hz, 2H) 2.80 (d, J=9.60 Hz, 1H) 7.16 (t, J=8.21 Hz, 2H) 7.57 (d, J=8.34 Hz, 2H) 7.52 (t, J=8.08 Hz, 2H) 7.81 (d, J=8.08 Hz, 2H) 7.74-7.83 (m, 1H) 8.15 (dd, J=8.59, 2.53 Hz, 1H) 8.31 (t, J=2.02 Hz, 1H) 8.76 (d, J=2.78 Hz, 1H) 9.65 (s, 1H); (M+H)+421.2.

The following compounds may be prepared in analogous fashion using and the appropriate aniline:

| Example | Chemical Name | LC rt | Method | MS (M + H)+ |
|---|---|---|---|---|
| Ex. 4-4 | (4-{4-[6-(3-methylphenylamino)-pyridin-3-yl]-phenyl}-cyclohexyl)-acetic acid | 1.53 | A | 401.2 |
| Ex. 4-5 | (4-{4-[6-(3-Trifluoromethylphenylamino)-pyridin-3-yl]-phenyl}-cyclohexyl)-acetic acid | 1.62 | A | 455.2 |
| Ex. 4-6 | (4-{4-[6-(3-Methoxyphenylamino)-pyridin-3-yl]-phenyl}-cyclohexyl)-acetic acid | 1.55 | A | 417.2 |
| Ex. 4-7 | (4-{4-[6-(2-Fluorophenylamino)-pyridin-3-yl]-phenyl}-cyclohexyl)-acetic acid | 1.49 | A | 405.2 |
| Ex. 4-8 | (4-{4-[6-(2-Methoxyphenylamino)-pyridin-3-yl]-phenyl}-cyclohexyl)-acetic acid | 1.55 | A | 417.2 |
| Ex. 4-9 | (4-{4-[6-(6-Trifluoromethyl-pyridin-3-ylamino)-pyridin-3-yl]-phenyl}-cyclohexyl)-acetic acid | 1.53 | A | 456.3 |

The following compounds may also be prepared in similar fashion from the corresponding aniline and haloarene:

| Example | Name | LC rt | Method | (M + H)+ |
|---|---|---|---|---|
| Ex. 4-10 | (4-{4-[6-(6-Methoxy-pyridin-3-ylamino)-5-methyl-pyridin-3-yl]-phenyl}-cyclohexyl)-acetic acid | 1.47 | A | 432.1 |
| Ex. 4-11 | (4-{4-[5-Fluoro-6-(6-methoxy-pyridin-3-ylamino)-pyridin-3-yl]-phenyl}-cyclohexyl)-acetic acid | 1.44 | A | 436.1 |

Example 4-12

(4-{4-[6-(2-Methyl-6-trifluoromethyl-pyridin-3-ylamino)-pyridin-3-yl]-phenyl}-cyclohexyl)-acetic acid

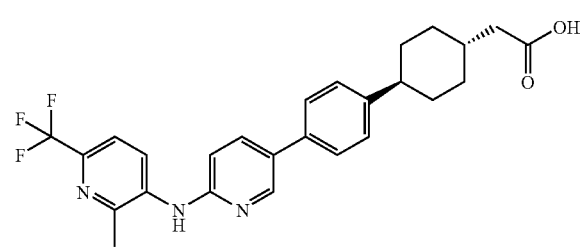 [SMILES: Cc1nc(C(F)(F)F)ccc1Nc1ccc(-c2ccc([C@H]3CC[C@H](CC(=O)O)CC3)cc2)cn1]

A. (5-Bromo-pyridin-2-yl)-2-methyl-6-trifluoromethyl-pyridin-3-yl)-amine 2,5-dibromopyridine (474 mg, 2 mmol) and 2-Methyl-6-trifluoromethyl-pyridin-3-ylamine (352 g, 2 mmol) were dissolved in 1,4-dioxane (4 mL) in a pressure vessel. Pd$_2$ dba$_3$ (55 mg, 0.06 mmol) and XANTPHOS (46 mg, 0.08 mmol) were added, followed by cesium carbonate (1.3 g, 4 mmol). The mixture was sparged with nitrogen for 10 minutes, then the vessel was sealed and heated at 100° C. for 18 hours. The mixture was partitioned between EtOAc and saturated aqueous NH$_4$Cl, then the organic layer was washed with brine, dried with magnesium sulfate, filtered, and concentrated via rotary evaporation. The crude material was purified via column chromatography on silica gel, eluting with a gradient of EtOAc/hexanes (7-60%) to obtain the target compound as a solid: $^1$H NMR (400 MHz, CDCl$_3$) δ ppm 2.62 (s, 3H) 6.36 (br. s., 1H) 6.75 (d, J=8.59 Hz, 1H) 7.53 (d, J=8.34 Hz, 1H) 7.69 (dd, J=8.84, 2.53 Hz, 1H) 8.32-8.37 (m, 2H); MS (M+H)+334.7.

B. (4-{4-[6-(2-Methyl-6-trifluoromethyl-pyridin-3-ylamino)-pyridin-3-yl]-phenyl}-cyclohexyl)-acetic acid methyl ester (5-Bromo-pyridin-2-yl)-(2-methyl-6-trifluoromethyl-pyridin-3-yl)-amine (290 mg, 0.87 mmol) and {4-[4-(4,4,5,5-Tetramethyl-[1,3,2]dioxaborolan-2-yl)-phenyl]-cyclohexyl}-acetic acid methyl ester (312 mg, 0.87 mmol) were dissolved in anhydrous DME (3 mL) in a pressure vessel. PdCl$_2$dppf (21 mg, 0.026 mmol) was added, followed by aqueous sodium carbonate (2M, 0.870 mL, 1.74 mmol). The mixture was sparged with nitrogen for 10 minutes, then the vessel was sealed and heated at 80° C. for 18 hours. The mixture was partitioned between EtOAc and water, washed with brine, dried with magnesium sulfate, filtered, and concentrated via rotary evaporation. The crude material was purified via column chromatography on silica gel, eluting with a gradient of EtOAc/hexanes (7-50%) to obtain the target compound as a solid: $^1$H NMR (400 MHz, DMSO-d6) δ ppm 1.08-1.21 (m, 2H) 1.50 (td, J=12.44, 10.23 Hz, 2H) 1.81 (m, 4H) 2.25 (d, J=6.57 Hz, 2H) 2.59 (s, 3H) 3.60 (s, 3H) 7.22 (d, J=8.59 Hz, 1H) 7.31 (d, J=8.34 Hz, 2H) 7.57 (d, J=8.34 Hz, 2H) 7.66 (d, J=8.59 Hz, 1H) 7.97 (dd, J=8.59, 2.53 Hz, 1H) 8.48 (d, J=2.53 Hz, 1H) 8.64 (s, 1H) 8.66 (d, J=8.34 Hz, 1H); MS-(M+H)+484.3.

C. (4-{4-[6-(2-Methyl-6-trifluoromethyl-pyridin-3-ylamino)-pyridin-3-yl]-phenyl}cyclohexyl)-acetic acid (4-{4-[6-(2-Methyl-6-trifluoromethyl-pyridin-3-ylamino)-pyridin-3-yl]-phenyl}-cyclohexyl)-acetic acid methyl ester (332 g, 0.69 mmol) was dissolved in THF/MeOH (3:1, 4 mL) and to it was added aqueous LiOH (4M, 1 mL). The mixture was stirred at room temperature for 18 hours, then the organic solvent was removed via rotary evaporation. The remaining crude was diluted with water and the pH was adjusted to 2 with 1 M HCl. The resulting precipitate was collected by filtration and dried under vacuum to obtain the title compound as a white solid: $^1$H NMR (400 MHz, DMSO-d6) δ ppm 0.95-1.04 (m, 2H) 1.44 (dd, J=12.51, 2.91 Hz, 2H) 1.67 (br. s., 1H) 1.74-1.87 (m, 6H) 2.47 (m, 1H) 2.60 (s, 3H) 7.25 (d, J=8.59 Hz, 1H) 7.30 (d, J=8.34 Hz, 2H) 7.56 (d, J=8.34 Hz, 2H) 7.66 (d, J=8.34 Hz, 1H) 7.97 (dd, J=8.72, 2.65 Hz, 1H) 8.48 (d, J=2.27 Hz, 1H) 8.67 (d, J=8.34 Hz, 1H) 8.80 (s, 1H); MS (M+H)+470.3.

Example 4-13

Oxo-(4-{4-[6-(6-trifluoromethyl-pyridin-3-ylamino)-pyridin-3-yl]-phenyl}-piperidin-1-yl)-acetic acid

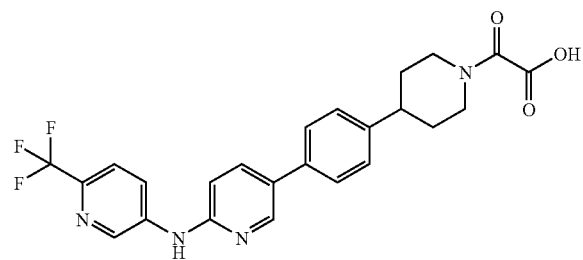 [SMILES: O=C(O)C(=O)N1CCC(c2ccc(-c3ccc(Nc4ccc(C(F)(F)F)nc4)nc3)cc2)CC1]

A. 4-(4-Bromo-phenyl)-piperidine-1-carboxylic acid tert-butyl ester

To a solution of 4-(4-Bromo-phenyl)-piperidine (1 g, 4.2 mmol) in DMF (8 mL) was added NaH (168 mg, 4.2 mmol, 60% in mineral oil). The slurry was stirred for 15 minutes, then di-$^t$butyl dicarbonate (915 mg, 4.2 mmol) was added. The mixture was stirred for 18 hours, then quenched with methanol, and partitioned between 30% EtOAc/hexanes and water. The organic layer was dried with magnesium sulfate, filtered, and concentrated via rotary evaporation to yield the title compound as a white solid, which was taken on to the next step without further purification; $^1$H NMR (400 MHz, CDCl$_3$-d) δ ppm 1.49 (s, 9H) 1.58 (qd, J=12.67, 4.42 Hz, 2H) 1.80 (d, J=13.14 Hz, 2H) 2.61 (tt, J=12.22, 3.57 Hz, 1H) 2.79 (t, J=12.63 Hz, 2H) 4.24 (d, J=6.57 Hz, 2H) 7.08 (m, 2H) 7.43 (m, 2H); MS (M+H)+340.8 and 342.8.

B. 4-[4-(4,4,5,5-Tetramethyl-[1,3,2]dioxaborolan-2-yl)-phenyl]-piperidine-1-carboxylic acid tert-butyl ester 4-(4-Bromo-phenyl)-piperidine-1-carboxylic acid tert-butyl ester (1.4 g, 4.1 mmol) and bispinacolatodiboron (1.15 g, 4.53 mmol) were dissolved in DME (3 mL) in a pressure vessel, and to the solution was added PdCl$_2$dppf (100 mg, 0.12 mmol) and KOAc (808 mg, 8.2 mmol). The mixture was sparged with nitrogen for 10 minutes, then the vessel was sealed and stirred at 80° C. for 18 hours. The reaction mixture was partitioned between EtOAc and water, washed with brine, dried with magnesium sulfate, filtered, and concentrated via rotary evaporation. The crude material was purified via flash chromatography on silica gel eluting with a gradient of EtOAc/hexanes (5-20%) to obtain the target compound as a solid: MS (M+H)+388.3.

C. 4-{4-[6-(6-Trifluoromethyl-pyridin-3-ylamino)-pyridin-3-yl]-phenyl}-piperidine-1-carboxylic acid tert-butyl ester 4-[4-(4,4,5,5-Tetramethyl-[1,3,2]dioxaborolan-2-yl)-phenyl]-piperidine-1 carboxylic acid tert-butyl ester (1.56 g, 4.1 mmol) and (5-Bromo-pyridin-2-yl)-(6-trifluoromethyl-pyridin-3-yl)-amine (1.28 g, 4.0 mmol) were dissolved in DME (8 mL) in a pressure vessel, and to the solution was added PdCl$_2$dppf (100 mg, 0.12 mmol) and Na$_2$CO$_3$ (2.0M, 4.0 mL, 8.1 mmol). The mixture was sparged with nitrogen for 10 minutes, then the vessel was sealed and stirred at 80° C. for 18 hours. The mixture was partitioned between EtOAc and saturated aqueous NH$_4$Cl, washed with brine, dried with magnesium sulfate, filtered, and concentrated via rotary evaporation. The crude material was purified via column chromatography on silica gel, eluting with a gradient of EtOAc/hexanes (10-50%) to obtain the target compound as a solid: $^1$H NMR (400 MHz, DMSO-d6) δ ppm 1.25 (br. s., 2H) 1.42 (s, 9H) 1.52 (qd, J=12.63, 4.55 Hz, 2H) 1.77 (m, 2H) 2.66-2.76 (m, 1H) 4.09 (m, 2H) 7.03 (d, J=8.59 Hz, 1H) 7.34 (d, J=8.34 Hz, 2H) 7.60 (d, J=8.08 Hz, 2H) 7.79 (d, J=8.84 Hz, 1H) 7.99 (dd, J=8.72, 2.65 Hz, 1H) 8.56 (d, J=2.53 Hz, 1H) 8.91 (d, J=2.53 Hz, 1H) 9.87 (s, 1H); MS (M+H)+499.3.

D. [5-(4-Piperidin-4-yl-phenyl)-pyridin-2-yl]-(6-trifluoromethyl-pyridin-3-yl)-amine 4-{4-[6-(6-Trifluoromethyl-pyridin-3-ylamino)-pyridin-3-yl]-phenyl}-piperidine-1-carboxylic acid tert-butyl ester (1.02 g, 2.0 mmol) was slurried in 1,4-dioxane/MeOH (5:1, 6 mL) and was treated with HCl (4M in 1,4-dioxane, 2 mL). After 18 hours, added more HCl (4M, 1,4-dioxane, 3 mL) and stirred 2 days. The solvents were removed via rotary evaporation and the crude was dried under vacuum to obtain the hydrochloride salt of the title compound as a sticky yellow solid which was used in the next step without further purification: MS (M+H)+399.4.

E. Oxo-(4-{4-[6-(6-trifluoromethyl-pyridin-3-ylamino)-pyridin-3-yl]-phenyl}-piperidin-1-yl)-acetic acid ethyl ester

[5-(4-Piperidin-4-yl-phenyl)-pyridin-2-yl]-(6-trifluoromethyl-pyridin-3-yl)-amine hydrochloride (200 mg, 0.46 mmol) was slurried in DCM (2 mL) and to it was added N,N-diisopropylethylamine (1.320 mL, 7.6 mmol). Chloro-oxo-acetic acid ethyl ester (0.076 mL, 0.69 mmol) was added dropwise, and the reaction was stirred for 18 hours. The reaction mixture was partitioned between EtOAc and water, washed with brine, dried with magnesium sulfate, filtered, and concentrated via rotary evaporation to obtain 229 mg of the title compound as a crude oil, which was taken to the next step without purification: MS (M+H)+499.2.

F. Oxo-(4-{4-[6-(6-trifluoromethyl-pyridin-3-ylamino)-pyridin-3-yl]-phenyl}-piperidin-1-yl)-acetic acid Oxo-(4-{4-[6-(6-trifluoromethyl-pyridin-3-ylamino)-pyridin-3-yl]-phenyl}-piperidin-1-yl)-acetic acid ethyl ester (229 mg, 0.46 mmol) was dissolved in THF/MeOH/DMF (3:1:1, 5 mL) and to the solution was added aqueous LiOH (4M, 1 mL). The mixture was stirred at room temperature for 18 hours, then the reaction mixture was filtered and purified by reverse-phase preparative HPLC to give the title compound: $^1$H NMR (400 MHz, DMSO-$d_6$) δ ppm 1.41 (m, 1H) 1.52 (m, 1H) 1.76 (td, J=13.89, 1.52 Hz, 2H) 2.72-2.81 (m, 1H) 2.96 (td, J=12.63, 2.27 Hz, 1H) 3.16 (d, J=5.31 Hz, 1H) 3.85 (dd, J=11.37, 2.27 Hz, 1H) 4.37 (ddd, J=12.69, 1.83, 1.64 Hz, 1H) 7.03 (d, J=8.59 Hz, 1H)-7.31 (d, J=8.34 Hz, 2H) 7.60 (d, V=8.34 Hz, 2H) 7.78 (d, J=8.84 Hz, 1H) 7.98 (dd, J=8.72, 2.65 Hz, 1H) 8.55 (d, J=2.53 Hz, 1H) 8.58 (dd, J=8.59, 2.02 Hz, 1H) 8.90 (d, J=2.27 Hz, 1H) 9.91 (s, 1H); MS (M+H)+471.2.

Example 4-14

(4-Hydroxy-4-{4-[6-(6-trifluoromethyl-pyridin-3-ylamino)-pyridin-3-yl]-phenyl}-piperidin-1-yl)-acetic acid

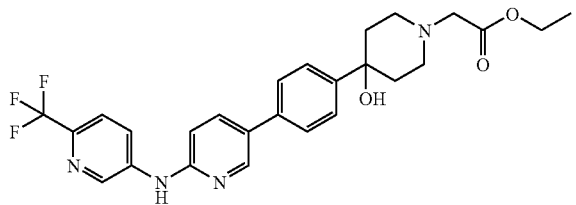 [SMILES: CCOC(=O)CN1CCC(O)(c2ccc(-c3ccc(Nc4ccc(C(F)(F)F)nc4)nc3)cc2)CC1]

A. (4-Hydroxy-4-{4-[6-(6-trifluoromethyl-pyridin-3-ylamino)-pyridin-3-yl]-phenyl}-piperidin-1-yl)-acetic acid ethyl ester 4-{4-[6-(6-Trifluoromethyl-pyridin-3-ylamino)-pyridin-3-yl]-phenyl}-piperidin-4-ol (153 mg, 0.37 mmol, prepared by analogous procedures described above) was dissolved in DMF (2 mL) and to it was added $K_2CO_3$ (128 mg, 0.93 mmol) followed by bromo-acetic acid ethyl ester (0.050 mL, 0.44 mmol) added dropwise, and the reaction was stirred for 18 hours. The reaction mixture was partitioned between 40% EtOAc/hexanes and water, washed with brine, dried with magnesium sulfate, filtered, and concentrated via rotary evaporation to obtain the title compound as a crude oil, which was taken to the next step without purification: MS (M+H)+ 499.4.

B. (4-Hydroxy-4-{4-[6-(6-trifluoromethyl-pyridin-3-ylamino)-pyridin-3-yl]-phenyl}-piperidin-1-yl)-acetic acid (4-Hydroxy-4-{4-[6-(6-trifluoromethyl-pyridin-3-ylamino)-pyridin-3-yl]-phenyl}-piperidin-1-yl)-acetic acid ethyl ester (137 mg, 0.27 mmol) was dissolved in THF/MeOH/DMF (3:1:1, 5 mL) and to the solution was added aqueous LiOH (4M, 1 mL). The mixture was stirred at room temperature for 18 hours, then the reaction mixture was filtered and purified by reverse-phase preparative HPLC to give the title compound: $^1$H NMR (400 MHz, DMSO-$d_6$) δ ppm 1.54 (qd, J=12.38, 4.29 Hz, 1H) 1.42 (qd, J=12.51, 4.42 Hz, 1H) 1.77 (td, J=14.08, 1.14 Hz, 2H) 2.78 (m, 1H) 2.98 (td, J=12.63, 2.27 Hz, 1H) 3.29 (s, 2H) 3.87 (dd, J=11.37, 2.27 Hz, 1H) 4.39 (ddd, J=12.69, 1.83, 1.64 Hz, 1H) 7.04 (d, J=8.59 Hz, 1H) 7.32 (d, J=8.34 Hz, 2H) 7.61 (d, J=8.34 Hz, 2H) 7.80 (d, J=8.84 Hz, 1H) 7.99 (dd, J=8.72, 2.65 Hz, 1H) 8.55-8.62 (m, 1H) 8.57 (d, J=2.53 Hz, 1H) 8.92 (d, J=2.27 Hz, 1H) 9.93 (s, 1H); (M+H)+473.3.

Example 5-1

(4-{4-[5-(6-Trifluoromethyl-pyridin-3-ylamino)-pyridin-2-yl]-phenyl}-cyclohexyl)-acetic acid

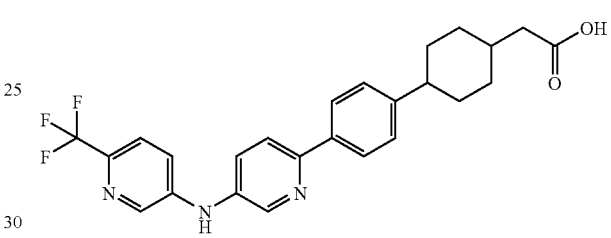

A. {4-[4-(5-Bromo-pyridin-2-yl)-phenyl]-cyclohexyl}-acetic acid methyl ester

To a solution of {4-[4-(4,4,5,5-tetramethyl-[1,3,2]dioxaborolan-2-yl)-phenyl]-cyclohexyl}-acetic acid methyl ester (4.0 g, 11.2 mmol, 1.0 equiv) and 2,5-dibromopyridine (3.2 g, 13.4 mmol, 1.2 equiv) in 50 Ml toluene/ethanol (1:1) was added 2 M $Na_2CO_3$ (16.8 Ml, 3 equiv) followed by Pd(PPh$_3$)$_4$ (0.38 g, 0.34 mmol, 0.03 equiv). The biphasic mixture was sparged with nitrogen for 10 min, then heated to 60° C. for 3 days. The reaction was cooled to room temperature and then partitioned between ethyl acetate and saturated ammonium chloride solution. The organic extracts were washed with brine, then dried over sodium sulphate and concentrated in vacuo. Purification by silica gel chromatography (7-40% EtOAc in hexanes) afforded the title compound as a yellow solid: $^1$H NMR (400 MHz, CDCl$_3$) δ 1.11 (dd, J=13.01, 2.15 Hz, 2H) 1.41-1.54 (m, 2H) 1.76-1.90 (m, 5H) 2.20 (d, J=6.57 Hz, 2H) 2.46 (tt, J=12.09, 3.19 Hz, 1H) 3.62 (s, 3H) 7.23 (d, J=8.08 Hz, 2H) 7.53 (dd, J=8.59, 0.76 Hz, 1H) 7.77 (dd, J=8.46, 2.40 Hz, 1H) 7.81 (q, J=3.87 Hz, 1H) 7.81 (d, J=8.34 Hz, 1H) 8.64 (d, J=1.77 Hz, 1H); (M+H)+390.0.

B. (4-{4-[5-(6-Trifluoromethyl-pyridin-3-ylamino)-pyridin-2-yl]-phenyl}-cyclohexyl)-acetic acid methyl ester A microwave vial was charged with {4-[4-(5-bromo-pyridin-2-yl)-phenyl]-cyclohexyl}-acetic acid methyl ester (3.4 g, 8.8 mmol, 1.0 equiv), 3-amino-6-trifluoromethyl pyridine (2.1 g, 13.1 mmol, 1.2 equiv), cesium carbonate (7.1 g, 21.9 mmol, 2.5 equiv), 2-dicyclohexylphosphino-2',4',6'-triisopropylbiphenyl (X-Phos, 0.42 g, 0.88 mmol, 0.1 equiv) and palladium acetate (0.30 g, 0.44 mmol, 0.05 equiv) in 20 Ml of toluene/t-butanol (9:1). The suspension was sparged with nitrogen for 10 min, then heated to 150° C. under microwave heating for 45 min. The reaction was cooled to room temperature, partitioned between ethyl acetate and water. The organic extracts were washed with brine, then dried over sodium sulphate and concentrated in vacuo. Purification by silica gel chromatography afforded the title compound: ¹H NMR (400 MHz, DMSO-d6) δ 1.10-1.21 (m, 1H) 1.51 (qd, J=12.72, 2.78 Hz, 2H) 1.70-1.87 (m, 5H) 2.26 (d, J=6.57 Hz, 2H) 2.50 (m, 1H) 3.61 (s, 3H) 7.33 (d, J=8.34 Hz, 2H) 7.65 (d, J=2.53 Hz, 1H) 7.67-7.74 (m, 2H) 7.89 (d, J=8.59 Hz, 1H) 7.95 (d, J=8.34 Hz, 2H) 8.46 (d, J=2.53 Hz, 1H) 8.54 (d, J=2.53 Hz, 1H) 9.18 (s, 1H); (M+H)+427.3.

C. (4-{4-[5-(6-Trifluoromethyl-pyridin-3-ylamino)-pyridin-2-yl]-phenyl}-cyclohexyl)-acetic acid A THF solution of (4-{4-[5-(6-trifluoromethyl-pyridin-3-ylamino)-pyridin-2-yl]-phenyl}-cyclohexyl)-acetic acid methyl ester was treated with 10% aqueous LiOH and heated to 50° C. overnight. Upon reaction completion, the mixture was acidified with concentrated HCl. The resulting precipitate was isolated by filtration to afford the title compound: ¹H NMR (400 MHz, DMSO-d6) δ 1.08-1.19 (m, 1H) 1.14 (dd, J=12.63, 2.27 Hz, 1H) 1.44-1.56 (m, 1H) 1.50 (dd, J=12.51, 2.65 Hz, 1H) 1.75 (br. S., 1H) 1.84 (d, J=10.61 Hz, 4H) 2.14 (d, J=6.82 Hz, 2H) 2.54 (m, 1H) 7.33 (d, J=8:34 Hz, 2H) 7.65 (d, J=2.53 Hz, 1H) 7.68-7.74 (m, 1H) 7.70 (d, J=8.34 Hz, 1H) 7.89 (d, J=8.59 Hz, 1H) 7.95 (d, J=8.59 Hz, 2H) 8.46 (d, J=2.78 Hz, 1H) 8.54 (d, J=2.53 Hz, 1H) 9.20 (s, 1H); (M+H)+ 456.3. Alternatively, the methyl ester can be dissolved in a mixture of THF and water, and treated with aqueous sodium hydroxide (4 equiv). The mixture can then be stirred at 50 degrees for 12 hours, at which point the THF is removed under reduced pressure to yield an opaque, white slurry, which affords the title compound as the corresponding sodium salt upon filtration. ¹H NMR (DMSO-d6, 500 MHz) δ 10.05 (s, 1H), 8.59 (d, 1H, J=2.8 Hz), 8.54 (s, 1H), 7.92 (d, 2H, J=8.2 Hz), 7.86 (d, 1H, J=8.8 Hz), 7.75 (dd, 1H, J=8.7.2.7 Hz), 7.69 (s, 2H), 7.27 (d, 2H, J=8.5 Hz), 2.45 (m, 1H), 1.84 (m, 4H), 1.67-1.80 (m, 3H), 1.41 (m, 2H), 1.02 (m, 2H); MS m/z 456 (M-Na+2H)⁺.

Using the appropriate amino derivative, the following compounds may also be prepared:

Example 5-13

{4-[4-(3-Methoxy-5-phenylamino-pyridin-2-yl)-phenyl]-cyclohexyl}-acetic acid

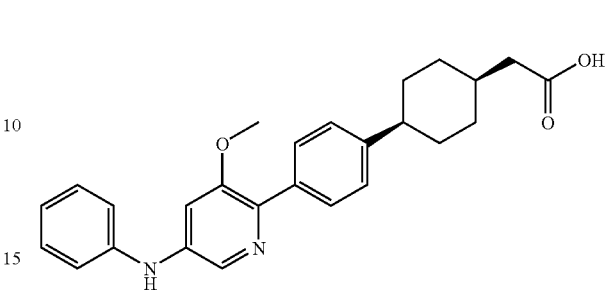

A. {4-[4-(3-Methoxy-5-nitro-pyridin-2-yl)-phenyl] cyclohexyl}-acetic acid methyl ester To a solution of 2-chloro-3-methoxy-5-nitro-pyridine (0.10 g, 0.53 mmol, 1.0 equiv) and {4-[4-(4,4,5,5-tetramethyl-[1,3,2]dioxaborolan-2-yl)-phenyl]-cyclohexyl}-acetic acid methyl ester (0.2 g, 0.56 mmol, 1.05 equiv) in 5 Ml DME was added 0.5 Ml saturated potassium carbonate solution and 10 mg Pd(PPh₃)₄ catalyst. The reaction was heated to 100° C. for 2 h. The crude reaction mixture was then concentrated in vacuo and then loaded directly onto a silica gel column. Elution with 30% EtOAc/hexanes afforded the title compound: 1H NMR (400 MHz, DMSO-d6) δ ppm 1.12-1.19 (m, 2H) 1.15 (d, J=13.14 Hz, 1H) 1.46-1.59 (m, 1H) 1.51 (dd, J=112.38, 2.78 Hz, 2H) 1.81 (d, J=5.56 Hz, 4H) 2.26 (d, J=6.82 Hz, 2H) 3.61 (s, 3H) 4.00 (s, 3H) 7.36 (d, J=8.34 Hz, 2H) 7.90 (d, J=8.34 Hz, 2H) 8.20 (d, J=2.02 Hz, 1H) 9.05 (s, 1H); (M+H)+385.1.

B. {4-[4-(5-Amino-3-methoxy-pyridin-2-yl)-phenyl]-cyclohexyl}-acetic acid methyl ester To a solution of {4-[4-(3-Methoxy-5-nitro-pyridin-2-yl)-phenyl]-cyclohexyl}-acetic acid methyl ester (0.14 g) in 10

| Example | Chemical Name | LC rt | Method | MS (M + H)⁺ |
|---|---|---|---|---|
| Ex. 5-2 | (4-{4-[5-(Pyridin-2-ylamino)-pyridin-2-yl]-phenyl}-cyclohexyl)-acetic acid | 1.30 | A | 388.3 |
| Ex. 5-3 | {4-[4-(5-Phenylaminopyridin-2-yl)-phenyl]-cyclohexyl}-acetic acid | 1.42 | A | 387.3 |
| Ex. 5-4 | (4-{4-[5-(5-Cyanopyridin-3-ylamino)-pyridin-2-yl]-phenyl}-cyclohexyl)-acetic acid | 1.28 | A | 413.3 |
| Ex. 5-5 | (4-{4-[5-(5-Trifluoromethylpyridin-2-ylamino)-pyridin-2-yl]-phenyl}-cyclohexyl)-acetic acid | 1.47 | A | 456.4 |
| Ex. 5-6 | (4-{4-[5-(4-Trifluoromethylphenylamino)-pyridin-2-yl]-phenyl}-cyclohexyl)-acetic acid | 1.54 | A | 455.4 |
| Ex. 5-7 | (4-{4-[5-(5-Methylpyridin-2-ylamino)-pyridin-2-yl]-phenyl}-cyclohexyl)-acetic acid | 1.44 | A | 402.3 |
| Ex. 5-8 | (4-{4-[5-(5-Trifluoromethylpyridin-2-ylamino)-pyridin-2-yl]-phenyl}-cyclohexyl)-acetic acid methyl ester | 1.36 | B | 470.4 |
| Ex. 5-9 | (4-{4-[5-(5-Chloropyridin-2-ylamino)-pyridin-2-yl]-phenyl}-cyclohexyl)-acetic acid | 1.48 | A | 422.3 |
| Ex. 5-10 | (4-{4-[5-(6-Methoxypyridin-3-ylamino)-pyridin-2-yl]-phenyl}-cyclohexyl)-acetic acid | 1.35 | A | 418.4 |
| Ex. 5-11 | (4-{4-[5-(5-Fluoropyridin-2-ylamino)-pyridin-2-yl]-phenyl}-cyclohexyl)-acetic acid | 1.39 | A | 406.4 |
| Ex. 5-12 | (4-{4-[5-(6-Acetylaminopyridin-3-ylamino)-pyridin-2-yl]-phenyl}-cyclohexyl)-acetic acid | 1.09 | A | 445.4 |

Ml EtOAc was added 30 mg Pd/C. The reaction vessel was purged with hydrogen, then stirred overnight under a balloon atmosphere of hydrogen. Filtration through Celite followed by removal of solvent in vacuo afforded the title compound: 1H NMR (400 MHz, DMSO-d6) δ ppm 0.94-1.02 (m, 1H) 1.01 (s, 3H) 1.31 (td, J=12.57, 9.98 Hz, 2H) 1.64 (d, J=11.37 Hz, 4H) 2.09 (d, J=6.82 Hz, 2H) 3.44 (s, 3H) 3.59 (s, 3H) 5.25 (s, 2H) 6.52 (d, J=2.02 Hz, 1H) 7.02 (d, J=8.34 Hz, 2H) 7.47 (d, J=2.02 Hz, 1H) 7.54 (d, J=8.34 Hz, 2H); (M+H)+355.1.

C. {4-[4-(3-Methoxy-5-phenylamino-pyridin-2-yl)-phenyl]-cyclohexyl}-acetic acid methyl ester To a solution of {4-[4-(5-Amino-3-methoxy-pyridin-2-yl)-phenyl]-cyclohexyl}-acetic acid methyl ester (0.12 g, 0.3 mmol, 1.0 equiv) and phenyl boronic acid (0.082 g, 0.67 mmol, 2.0 equiv) in 5 Ml dichloromethane was added pyridine (0.054 Ml, 0.67 mmol, 2.0 equiv), copper (II) acetate (0.092 g, 0.50 mmol, 1.5 equiv), and 4 Å molecular sieves. The heterogeneous reaction mixture was allowed to stir open to atmosphere for 18 h. Removal of solvent and purification by silica gel chromatography (40% EtOAc in hexanes) afforded the title compound: 1H NMR (400 MHz, DMSO-d6) δ ppm 1.14-1.31 (m, 2H) 1.50 (br. S., 1H) 1.55 (dd, J=12.51, 2.40 Hz, 2H) 1.87 (d, J=12.38 Hz, 5H) 2.31 (d, J=6.57 Hz, 2H) 3.66 (s, 3H) 3.86 (s, 3H) 6.96 (t, J=7.33 Hz, 1H) 7.20-7.38 (m, 7H) 7.82 (d, J=8.34 Hz, 2H) 8.11 (d, J=2.02 Hz, 1H) 8.53 (s, 1H); (M+H)+431.2.

D. {4-[4-(3-Methoxy-5-phenylamino-pyridin-2-yl)-phenyl]-cyclohexyl}-acetic acid To a solution of {4-[4-(3-Methoxy-5-phenylamino-pyridin-2-yl)phenyl]-cyclohexyl}-acetic acid methyl ester (0.082 g) in 5 Ml THF was added 5 Ml of a 4 M LiOH solution. The reaction was stirred overnight at room temperature, then heated to 60° C. for 5 h. Acidification to Ph 1 using concentrated HCl afforded a precipitate which was filtered to afford the title compound: 1H NMR (400 MHz, DMSO-d6) δ ppm 1.02-1.13 (m, 1H) 1.07 (dd, J=12.38, 2.27 Hz, 2H) 1.39-1.59 (m, J=12.88, 12.63, 12.63, 3.03 Hz, 3H) 1.77 (d, J=10.36 Hz, 4H) 2.09 (d, J=6.82 Hz, 2H) 3.84 (s, 3H) 7.00 (t, J=7.33 Hz, 1H) 7.20-7.24 (m, 2H) 7.31 (dd, J=7.71, 1.89 Hz, 4H) 7.34 (s, 1H) 7.51 (d, J=1.52 Hz, 1H) 7.61 (d, J=8.34 Hz, 2H) 7.91 (d, J=2.27 Hz, 1H) 9.27 (br. S., 1H); (M+H)+417.1.

The following compounds may be prepared in analogous fashion:

| Example | Chemical Name | LC rt | Method | MS (M + H)+ |
|---|---|---|---|---|
| Ex. 5-14 | {4-[4-(3-Methoxy-5-(3-fluorophenyl)amino-pyridin-2-yl)-phenyl]-cyclohexyl}-acetic acid | 1.4 | A | 435 |
| Ex. 5-15 | {4-[4-(3-Methoxy-5-(4-trifluoromethyl-phenyl)amino-pyridin-2-yl)-phenyl]-cyclohexyl}-acetic acid | 1.5 | A | 485 |
| Ex. 5-16 | {4-[4-(3-Methoxy-5-(3-chlorophenyl)amino-pyridin-2-yl)-phenyl]-cyclohexyl}-acetic acid | 1.5 | A | 451 |

Example 5-17

(4-{4-[5-(3-Fluoro-phenylamino)-pyridin-2-yl]-phenyl}-cyclohexyl)-acetic acid

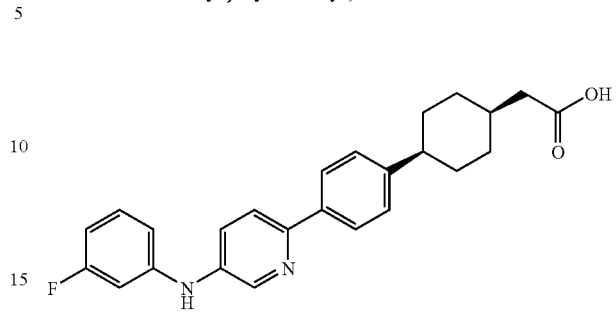

A. {4-[4-(5-Nitro-pyridin-2-yl)-phenyl]-cyclohexyl}-acetic acid methyl ester To a solution of 2-bromo-5-nitropyridine (0.81 g, 4.0 mmol, 1.0 equiv) and {4-[4-(4,4,5-tetramethyl-[1,3,2]dioxaborolan-2-yl)-phenyl]-cyclohexyl}-acetic acid methyl ester (1.5 g, 4.0 mmol, 1.05 equiv) in 20 Ml DME was added 2 Ml saturated potassium carbonate solution followed by 50 mg Pd(PPh3)4 catalyst. The reaction was then heated to 80° C. over the weekend. Removal of volatiles in vacuo followed by silica gel chromatography (20% EtOAc in hexanes) afforded the title compound: 1H NMR (400 MHz, DMSO-d6) δ ppm 0.94-1.06 (m, 1H) 1.00 (dd, J=12.76, 2.15 Hz, 2H) 1.30-1.42 (m, J=12.82, 12.60, 12.60, 2.91 Hz, 2H) 1.65 (br. S., 2H) 1.68 (d, J=3.54 Hz, 3H) 2.11 (d, J=6.82 Hz, 2H) 3.46 (s, 3H) 7.27 (d, J=8.34 Hz, 2H) 7.98 (d, J=8.34 Hz, 2H) 8.08 (dd, J=8.84, 0.51 Hz, 1H) 8.47 (dd, J=8.84, 2.78 Hz, 1H) 9.27 (d, J=2.27 Hz, 1H) (M+H)+355.1.

B. {4-[4-(5-Amino-pyridin-2-yl)-phenyl]-cyclohexyl}-acetic acid methyl ester To a solution of {4-[4-(5-Nitropyridin-2-yl)-phenyl]-cyclohexyl}-acetic acid methyl ester (1.4 g, 4.0 mmol) in 20 Ml EtOH was added Pd/C (0.4 g) followed by ammonium formate (2 g). The reaction mixture was heated to reflux for 4 h, then cooled to room temperature and filtered through Celite. Removal of solvent in vacuo afforded the title compound: 1H NMR (400 MHz, DMSO-d6) δ ppm 1.08-1.20 (m, 2H) 1.43-1.54 (m, 1H) 1.48 (dd, J=12.57, 2.46 Hz, 2H) 1.81 (d, J=11.75 Hz, 6H) 2.26 (d, J=6.69 Hz, 2H) 3.61 (s, 3H) 6.98 (dd, J=8.59, 2.78 Hz, 1'H) 7.24 (d, J=8.34 Hz, 2H) 7.57 (d, J=8.59 Hz, 1H) 7.81 (d, J=8.34 Hz, 2H) 8.00 (d, J=2.65 Hz, 1H); (M+H)+ 325.2.

C. (4-{4-[5-(3-Fluoro-phenylamino)-pyridin-2-yl]-phenyl}-cyclohexyl)-acetic acid methyl ester To a solution of {4-[4-(5-amino-pyridin-2-yl)-phenyl]-cyclohexyl}-acetic acid methyl ester (0.10 g, 0.3 mmol, 1.0 equiv) and 3-fluorophenyl boronic add (0.086 g, 0.61 mmol, 2.0 equiv) in 5 Ml dichloromethane was added pyridine (0.05 Ml, 0.61 mmol, 2.0 equiv), copper (II) acetate (0.084 g, 0.46 mmol, 1.5 equiv) and 4 Å molecular sieves. The heterogeneous mixture was allowed to stir open to atmosphere for 18 h. Purification by silica gel chromatography (20-45% EtOAc in hexanes) afforded the title compound: 1H NMR (400 MHz, DMSO-d6) δ ppm 1.12-1.27 (m, 2H) 1.47 (br. S., 1H) 1.53 (dd, J=12.51, 2.65 Hz, 1H) 1.67 (br. S., 1H) 1.85 (d, J=12.38

Hz, 4H) 2.29 (d, J=6.57 Hz, 2H) 3.34 (s, 2H) 3.64 (s, 3H) 6.69 (td, J=8.46, 2.53 Hz, 1H) 6.89 (dt, J=11.62, 2.15 Hz, 1H) 6.96 (dd, J=7.83, 1.77 Hz, 1H) 7.33 (d, J=8.34 Hz, 2H) 7.63 (dd, J=8.59, 2.78 Hz, 1H) 7.84 (d, J=8.59 Hz, 1H) 7.95 (d, J=8.34 Hz, 2H) 8.47 (s, 1H) 8.71 (s, 1H); (M+H)+419.3.

D. (4-{4-[5-(3-Fluoro-phenylamino)-pyridin-2-yl]-phenyl}-cyclohexyl)-acetic acid To a solution of (4-{4-[5-(3-Fluoro-phenylamino)-pyridin-2-yl]-phenyl}-cyclohexyl)-acetic acid methyl ester (0.10 g) in 5 Ml THF was added 5 Ml of a 4 M LiOH solution. The reaction was stirred overnight at room temperature, then heated to 60° C. overnight. Acidification to Ph 1 using concentrated HCl afforded a precipitate which was filtered to afford the title compound: 1H NMR (400 MHz, DMSO-d6) δ ppm 0.95-1.12 (m, 1H) 1.02 (dd, J=11.62, 9.35 Hz, 2H) 1.33 (br. S., 1H) 1.38 (dd, J=12.51, 2.65 Hz, 2H) 1.62 (d, J=9.35 Hz, 2H) 1.71 (d, J=10.11 Hz, 4H) 2.03 (d, J=6.82 Hz, 2H) 6.64-6.73 (m, 1H) 6.86-6.93 (m, 2H) 7.29 (d, J=8.34 Hz, 2H) 7.21-7.35 (m, 1H) 7.78 (d, J=8.34 Hz, 2H) 7.83-7.89 (m, 1H) 7.89-7.97 (m, 1H) 8.30 (s, 1H) 9.26 (br. S., 1H); (M+H)+405.1.

The following compounds may be prepared in analogous fashion:

| Example | Chemical Name | LC rt | Method | MS (M + H)+ |
|---|---|---|---|---|
| Ex. 5-18 | (4-{4-[5-(3-Chloro-phenylamino)-pyridin-2-yl]-phenyl}-cyclohexyl)-acetic acid | 1.5 | 10 | 421.1 |

Example 5-19

(4-{4-[5 (1-Methyl-1H-pyrazol-3-ylamino)-pyridin-2-yl]-phenyl}-cyclohexyl)-acetic acid

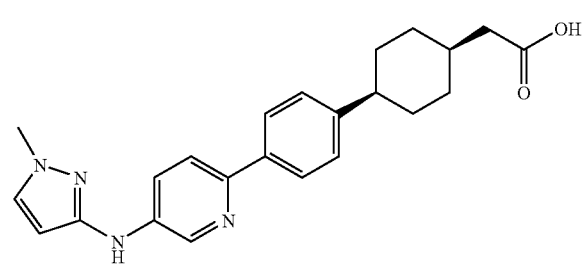 [SMILES: Cn1ccc(Nc2ccc(-c3ccc([C@H]4CC[C@@H](CC(=O)O)CC4)cc3)nc2)n1]

A. (6-Bromo-pyridin-3-yl)-(1-methyl-1H-pyrazol-3-yl)-amine

To a solution of 1-methyl-1H-pyrazol-3-ylamine (0.23 g, 2.3 mmol, 1.0 equiv) and 2-bromopyridyl-5-boronic acid (0.70 g, 3.5 mmol, 1.5 equiv) in 10 Ml dichloromethane was added pyridine (0.43 Ml, 5.4 mmol, 2.4 equiv), copper (II) acetate (0.63 g, 3.5 mmol, 1.5 equiv) and 4 Å molecular sieves. The heterogeneous reaction mixture was allowed to stir vigorously open to air overnight. The reaction was then filtered through Celite, concentrated in vacuo, and purified by silica gel chromatography to afford the title compound: 1H NMR (400 MHz, DMSO-d6) δ ppm 3.80 (s, 3H) 5.84 (s, 1H) 7.45 (d, J=8.59 Hz, 1H) 7.60 (d, J=2.02 Hz, 1H) 7.86 (dd, J=8.59, 3.03 Hz, 1H) 8.41 (d, J=2.78 Hz, 1H) 8.92 (s, 1H); (M+H)+255.1.

B. (4-{4-[5-(1-Methyl-1H-pyrazol-3-ylamino)-pyridin-2-yl]-phenyl}-cyclohexyl)-acetic acid methyl ester To a solution of (6-bromopyridin-3-yl)-(1-methyl-1H-pyrazol-3-yl)-amine (0.15 g, 0.6 mmol, 1.0 equiv) and {4-[4-(4,4,5,5-tetramethyl-[1,3,2]dioxaborolan-2-yl)-phenyl]-cyclohexyl}-acetic acid methyl ester (0.23 g, 0.7 mmol, 1.1 equiv) in 5 Ml DME was added 0.5 Ml saturated potassium carbonate solution followed by 5 mg Pd(PPh3)4 catalyst. The reaction was then heated to 80° C. for 2 h. Removal of volatiles in vacuo followed by silica gel chromatography (20% EtOAc in hexanes) afforded the title compound: 1H NMR (400 MHz, DMSO-d6) δ ppm 1.14-1.26 (m, 2H) 1.54 (qd, J=12.59, 2.40 Hz, 2H) 1.68 (br. S., 1H) 1.87 (d, J=11.12 Hz, 5H) 2.31 (d, J=6.57 Hz, 2H) 3.66 (s, 3H) 3.82 (s, 3H) 5.86 (s, 1H) 7.33 (d, J=8.34 Hz, 2H) 7.59 (d, J=2.02 Hz, 1H) 7.80 (d, J=8.84 Hz, 1H) 7.93 (d, J=8.34 Hz, 2H) 7.97 (dd, J=8.84, 2.78 Hz, 1H) 8.65 (d, J=2.27 Hz, 1H) 8.83 (s, 1H); (M+H)+405.2.

C. (4-{4-[5-(1-Methyl-1H-pyrazol-3-ylamino)-pyridin-2-yl]-phenyl}-cyclohexyl)-acetic acid To a solution of (4-{4-[5-(1-Methyl-1H-pyrazol-3-ylamino)-pyridin-2-yl]-phenyl}-cyclohexyl)-acetic acid methyl ester (0.12 g) in 5 Ml THF was added 5 Ml of a 4 M LiOH solution. The reaction was stirred overnight at room temperature, then heated to 60° C. overnight. Acidification to Ph 1 using concentrated HCl afforded a precipitate which was filtered to afford the title compound: 1H NMR (400 MHz, DMSO-d6) δ ppm 1.02-1.13 (m, 2H) 1.40-1.59 (m, J=12.82, 12.66, 12.66, 3.03 Hz, 3H) 1.77 (d, J=9.60 Hz, 5H) 2.09 (d, J=6.82 Hz, 2H) 2.48-2.54 (m, 1H) 3.74 (s, 3H) 5.84 (s, 1H) 7.38 (d, J=8.34 Hz, 2H) 7.58 (s, 1H) 7.83 (d, J=8.34 Hz, 2H) 8.09 (d, J=9.09 Hz, 1. H) 8.23 (d, J=11.62 Hz, 1H) 8.88 (s, 1H) 9.79 (br. S., 1H); (M+H)+391.1.

The following compounds may be prepared in analogous fashion:

| Example | Chemical Name | LC rt | Method | MS (M + H)+ |
|---|---|---|---|---|
| Ex. 5-20 | (4-{4-[5-(Isoxazol-3-ylamino)-pyridin-2-yl]-phenyl}-cyclohexyl)-acetic acid | 1.2 | A | 378.1 |

Example 5-21

(4-{4-[5-(5-Fluoro-4-methoxy-pyridin-3-ylamino)-pyridin-2-yl]-phenyl}-cyclohexyl)-acetic acid

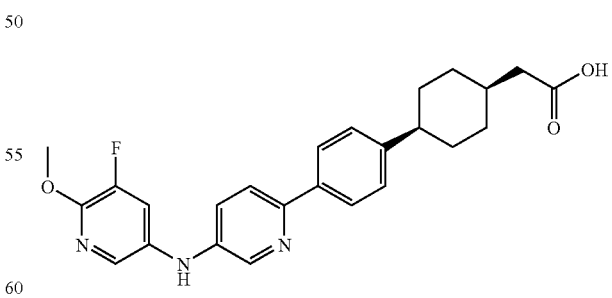

A. (6-Bromo-pyridin-3-yl)-(5-fluoro-6-methoxy-pyridin-3-yl)-amine

To a solution of 6-bromopyridin-3-ylamine (0.20 g, 1.2 mmol, 1.0 equiv) and 2-methoxy-3-fluoropyridyl-5-boronic acid (0.39 g, 2.3 mmol, 2.0 equiv) in 10 Ml dichloromethane was added pyridine (0.24 Ml, 3.0 mmol, 2.5 equiv), copper (II) acetate (0.32 g, 1.7 mmol, 1.5 equiv) and 4 Å molecular sieves. The heterogeneous reaction mixture was allowed to stir vigorously open to air overnight. The reaction was then filtered through Celite, concentrated in vacuo, and purified by silica gel chromatography to afford the title compound: 1H NMR (400 MHz, DMSO-d6) 3 ppm 3.96 (s, 3H) 7.35 (d, J=3.03 Hz, 1H) 7.37 (d, J=3.03 Hz, 1H) 7.42-7.46 (m, 1H) 7.62 (dd, J=11.87, 2.27 Hz, 1H) 7.88 (d, J=2.53 Hz, 1H) 8.09 (s, 1H) 8.52 (s, 1H); (M+H)+300.0.

B. (4-{4-[5-(5-Fluoro-6-methoxy-pyridin-3-ylamino)-pyridin-2-yl]-phenyl}-cyclohexyl)-acetic acid methyl ester To a solution of (6-bromo-pyridin-3-yl)-(5-fluoromethoxy-pyridin-3-yl)-amine (0.17 g, 0.6 mmol, 1.0 equiv) and {4-[4-(4,4,5,5-tetramethyl-[1,3,2]dioxaborolan-2-yl)-phenyl]-cyclohexyl}-acetic add methyl ester (0.22 g, 0.6 mmol, 1.0 equiv) in 15 Ml DME was added 1 Ml saturated sodium carbonate solution followed by 10 mg Pd(PPh3)4 catalyst. The reaction was then heated to 80° C. overnight. Removal of volatiles in vacuo followed by silica gel chromatography (20% EtOAc in hexanes) afforded the title compound: 1H NMR (400 MHz, DMSO-d6) δ ppm 0.93-1.08 (m, 1H) 1.01 (d, J=2.78 Hz, 1H) 1.31-1.52 (m, 3H) 1.62 (s, 2H) 1.69 (d, J=9.85 Hz, 4H) 2.02 (d, J=7.07 Hz, 2H) 3.81 (s, 3H) 7.28 (d, J=8.34 Hz, 2H) 7.58 (d, J=13.89 Hz, 1H) 7.75 (d, J=8.34 Hz, 3H) 7.70 (d, J=8.59 Hz, 1H) 7.81 (d, J=2.27 Hz, 1H) 7.89 (d, J=8.84 Hz, 1H) 8.15 (s, 1H) 9.04 (br. S., 1H); (M+H)+450.3.

C. (4-{4-[5-(5-Fluoro-6-methoxy-pyridin-3-ylamino)-pyridin-2-yl]-phenyl}-cyclohexyl)-acetic acid Using the saponification procedures outlined above, the title compound was produced: 1H NMR (400 MHz, DMSO-d6) δ ppm 0.93-1.08 (m, 1H) 1.01 (d, J=2.78 Hz, 1H) 1.31-1.52 (m, J=12.95, 12.66, 12.66, 3.16 Hz, 3H) 1.62 (s, 2H) 1.69 (d, J=9.85 Hz, 4H) 2.02 (d, J=7.07 Hz, 2H) 3.81 (s, 3H) 7.28 (d, J=8.34 Hz, 2H) 7.58 (d, J=13.89 Hz, 1H) 7.75 (d, J=8.34 Hz, 3H) 7.70 (d, J=8.59 Hz, 1H) 7.81 (d, J=2.27 Hz, 1H) 7.89 (d, J=8.84 Hz, 1H) 8.15 (s, 1H) 9.04 (br. S., 1H); (M+H)+436.1.

Example 5-22

(4-{5-[5-(6-Trifluoromethyl-pyridin-3-ylamino)-pyridin-2-yl]-spirocyclohexylidenyl-1,1'-indanyl}-acetic acid

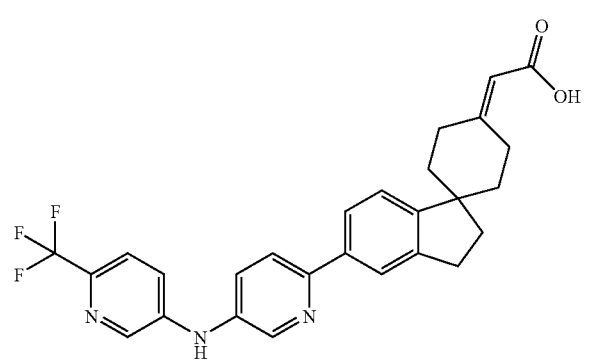 [SMILES: O=C(O)C=C1CCC2(CC1)CCc1cc(-c3ccc(Nc4ccc(C(F)(F)F)nc4)cn3)ccc12]

A. (6-Bromo-pyridin-3-yl)-(6-trifluoromethyl-pyridin-3-yl)-amine

To a solution of 3-amino-6-trifluoromethyl pyridine (0.25 g, 1.2 mmol, 2.0 equiv) and 2-bromopyridyl-5-boronic acid (0.10 g, 0.62 mmol, 1.0 equiv) in 5 Ml dichloromethane was added pyridine (0.10 Ml, 1.2 mmol, 2.0 equiv), copper (II) acetate (0.17 g, 0.93 mmol, 1.5 equiv) and 4 Å molecular sieves. The heterogeneous reaction mixture was allowed to stir vigorously open to air overnight. The reaction was then filtered through Celite, concentrated in vacuo, and purified by silica gel chromatography to afford the title compound: (M+H)+319.9.

B. (4-{5-[5-(6-Trifluoromethyl-pyridin-3-ylamino)-pyridin-2-yl]-spirocyclohexylidenyl-1,1'-indanyl}-acetic acid methyl ester A microwave vial was charged with (6-Bromopyridin-3-yl)-(6-trifluoromethyl-pyridin-3-yl)-amine (0.087 g, 0.28 mmol, 1.0 equiv) and {4-[5-(4,4,5,5-tetramethyl-[1,3,2]dioxaborolan-2-yl)]-spirocyclohexylidenyl-1,1'-indanyl}-acetic acid methyl ester (0.10 g, 0.28 mmol, 1.0 equiv) in 3 Ml dimethoxyethane. To this solution was added 2M Na2CO3 (0.35 Ml, 2.5 equiv) followed by PdCl2dppf (dichloromethane) complex (0.011 g, 0.014 mmol, 0.05 equiv). The mixture was sparged with nitrogen for 5 minutes and then heated to 150° C. for 30 min. The reaction was partitioned between EtOAc and water, and the organic extracts were washed with brine and dried over magnesium sulphate. Purification of the crude product by flash chromatography afforded the title compound: (M+H)+494.2.

C. (4-{5-[5-(6-Trifluoromethyl-pyridin-3-ylamino)-pyridin-2-yl]-spirocyclohexylidenyl-1,1'-indanyl}-acetic acid A solution of (4-{5-[5-(6-Trifluoromethyl-pyridin-3-ylamino)-pyridin-2-yl]-spirocyclohexylidenyl-1,1'-indanyl}-acetic acid methyl ester (0.020 g, 0.041 mmol, 1.0 equiv) in 1.5 Ml DMF was charged with 0.5 Ml of a 10% LiOH solution. The homogeneous solution was heated to 60° C. for 3 h. Purification by reverse-phase HPLC afforded the title compound: $^1$H NMR (400 MHz, DMSO-d6) δ 1.62-1.79 (m, 4H) 2.01-2.10 (m, 1H) 2.14 (td, J=7.58, 1.01 Hz, 2H) 2.31-2.44 (m, 2H) 2.95 (t, J=7.33 Hz, 2H) 3.79 (d, J=14.15 Hz, 1H) 5.63 (s, 1H)-7.25 (d, J=7.83 Hz, 1H) 7.65 (d, J=2.53 Hz, 1H) 7.68-7.74 (m, 2H) 7.82 (d, J=8.08 Hz, 1H) 7.88 (br. S., 1H) 7.86 (d, J=4.04 Hz, 1H) 8.46 (d, J=2.53 Hz, 1H) 8.53 (d, J=3.03 Hz, 1H) 9.20 (s, 1H); (M+H)+480.2.

Example 5-23

(4-{4-[5-(Benzooxazol-2-ylamino)-pyridin-2-yl]-phenyl}-cyclohexyl)-acetic acid

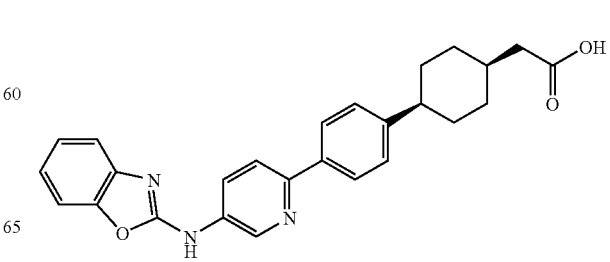

A. (4-{4-[5-(Benzooxazol-2-ylamino)-pyridin-2-yl]-phenyl}-cyclohexyl)-acetic acid methyl ester 65 mg of {4-[4-(5-Amino-pyridin-2-yl)-phenyl]-cyclohexyl}-acetic acid methyl ester and 0.3 Ml of 2-chlorobenzoxazole were dissolved in 1.5 Ml of t-BuOH/DME (1:1) in a 5 Ml microwave tube with a stirring bar. 0.1 Ml of 4N—HCl in dioxane was added and the reaction vessel was sealed and heated at 120° C. for 2 hours by microwave. The reaction was diluted with ethyl acetate and the resulting precipitates were filtered and washed with ethyl acetate. The filter cake was dried by air in the suction funnel and analyzed by $^1$H-NMR (400 MHz, DMSO-d$_6$) δ ppm 1.2 (s, 3H) 1.5 (s, 2H) 1.8 (s, 6H) 2.3 (d, J=6.8 Hz, 2H) 3.6 (s, 4H) 7.2 (m, 1H) 7.3 (m, 1H) 7.3 (d, J=8.3 Hz, 2H) 7.5 (d, J=13.9 Hz, 2H) 8.0 (m, 3H) 8.4 (m, 1H) 8.9 (d, J=2.3 Hz, 1H) 11.0 (s, 1H); (M+H)+442.2.

B. (4-{4-[5-(Benzooxazol-2-ylamino)-pyridin-2-yl]-phenyl}-cyclohexyl)-acetic acid (4-{4-[5 (Benzooxazol-2-ylamino)-pyridin-2-yl]-phenyl}-cyclohexyl)-acetic acid methyl ester was stirred in 4 Ml of THF/water (1:1) and treated with 30 mg of LiOH at ambient temperature. The reaction was then heated at 50° C. and stirred overnight. LC-MS analysis indicated the reaction was complete. The reaction was diluted with water (2 Ml) and neutralized with 6N HCl. The resulting precipitate was filtered and washed with water and ethyl acetate. The precipitate was dried and analyzed by 1H NMR (400 MHz, DMSO-D6) δ ppm 1.1 (m, 2H) 1.5 (s, 2H) 1.8 (t, J=6.7 Hz, 1H) 1.8 (s, 4H) 2.2 (d, J=6.8 Hz, 2H) 7.2 (td, J=7.8, 1.3 Hz, 1H) 7.3 (td, J=7.6, 1.1 Hz, 1H) 7.3 (d, J=8.3 Hz, 2H) 7.5 (dd, J=13.9, 7.3 Hz, 2H) 8.0 (d, J=8.1 Hz, 3H) 8.3 (dd, J=8.7, 2.7 Hz, 1H) 8.9 (d, J=3.0 Hz, 1H); (M+H)=428.1.

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt: $^1$H NMR (DMSO-d6, 500 MHz) δ 8.73 (s, 1H), 8.29 (dd, 1H, J=8.7, 2.7 Hz), 7.86 (d, 2H, J=8.2 Hz), 7.81 (d, 1H, J=8.8 Hz), 7.31 (m, 2H), 7.21 (d, 2H, J=8.2 Hz), 7.09 (t, 1H, J=7.6 Hz), 6.97 (t, 1H, J=7.7 Hz), 2.40 (m, 1H), 1.83 (d, 2H, J=6.9 Hz), 1.75 (m, 4H), 1.65 (m, 1H), 1.40 (m, 2H), 1.02 (m, 2H); MS m/z 428 (M-Na+2H)$^+$.

Example 5-24

(4-{4-[5-(2,2-Dimethyl-propionylamino)-pyridin-2-yl]-phenyl}-cyclohexyl)-acetic acid

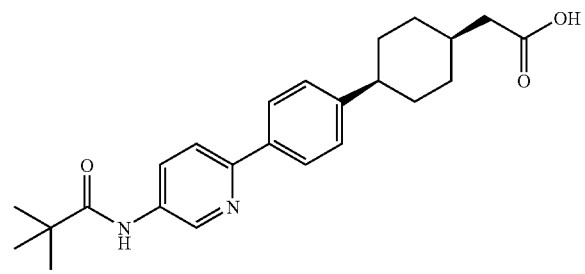 [SMILES: CC(C)(C)C(=O)Nc1ccc(-c2ccc([C@H]3CC[C@@H](CC(=O)O)CC3)cc2)nc1]

A. (4-{4-[5-(2,2-Dimethyl-propionylamino)-pyridin-2-yl]-phenyl}-cyclohexyl)-acetic acid methyl ester To a mixture of {4-[4-(5-amino-pyridin-2-yl)-phenyl]-cyclohexyl}-acetic acid methyl ester (100 mg, 0.3 mmol) in methylene chloride (10 ml) was added triethylamine (43 ul, 0.3 mmol) and trimethylacetyl chloride (40 ul, 0.3 mmol). After 15 hours at room temperature, the reaction was diluted with hexanes to afford a precipitate which was collected by filtration: 1H NMR (400 MHz, DMSO-d6) δ ppm 1.15 (dd, J=12.69, 1.71 Hz, 2H) 1.26 (s, 10H) 1.42-1.56 (m, 1H) 1.50 (d, J=9.85 Hz, 1H) 1.82 (d, J=11.37 Hz, 5H) 2.26 (d, J=6.69 Hz, 2H) 3.61 (s, 3H) 7.32 (d, J=8.34 Hz, 2H) 7.87 (d, J=8.72 Hz, 1H) 7.95 (d, J=8.34 Hz, 2H) 8.15 (dd, J=8.72, 2.53 Hz, 1H) 8.88 (d, J=2.53 Hz, 1H) 9.53 (s, 1H); (M+H)+409.2.

B. (4-{4-[5-(2,2-Dimethyl-propionylamino)-pyridin-2-yl]-phenyl}-cyclohexyl)-acetic acid A mixture of (4-{4-[5-(2,2-dimethyl-propionylamino)-pyridin-2-yl]-phenyl}-cyclohexyl)-acetic acid methyl ester (90 mg, 0.2 mmol) was stirred for 15 hours in a 1:1 mixture of THF/4M LiOH (10 ml). Neutralization with concentrated HCl afforded a precipitate which was isolated by filtration: 1H NMR (400 MHz, DMSO-d6) δ ppm 1.02 (dd, J=12.25, 1.89 Hz, 2H) 1.19 (s, 10H) 1.41 (dd, J=112.44, 2.59 Hz, 2H) 1.77 (t, J=13.14 Hz, 6H) 1.95 (d, J=6.95 Hz, 2H) 7.24 (d, J=8.34 Hz, 2H) 7.78 (d, J=18.72 Hz, 1H) 7.87 (d, J=8.34 Hz, 2H) 8.09 (dd, J=8.72, 2.53 Hz, 1H) 8.83 (d, J=2.40 Hz, 1H) 9.52 (s, 1H); (M+H)+395.1.

Example 5-25

[4-(4-{5-[3-(4-Trifluoromethoxy-phenyl)-ureido]-pyridin-2-yl}-phenyl)-cyclohexyl]-acetic acid

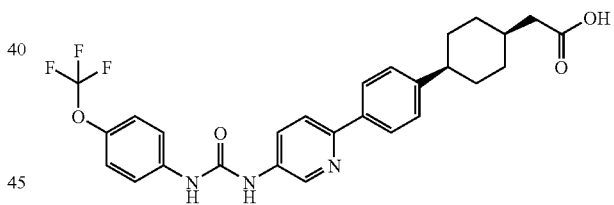

To 150 mg (0.5 mmol) {4-[4-(5-Amino-pyridin-2-yl)-phenyl]-cyclohexyl}-acetic acid methyl ester in 5 mL DCM, 102 mg (0.5 mmol) 1-Isocyanato-4-trifluoromethoxy-benzene was added and the resulting mixture was stirred at room temperature over night. Dilution of reaction mixture with hexanes caused desired product to precipitate which was collected by filtration to afford [4-(4-{5-[3-(4-Trifluoromethoxy-phenyl)-ureido]-pyridin-2-yl}-phenyl)-cyclohexyl]-acetic acid methyl ester: M+1=528.2. $^1$H NMR (400 MHz, DMSO-D6) δ ppm 1.09-1.20 (m, 2H) 1.50 (td, J=112.63, 10.11 Hz, 2H) 1.80 (s, 3H) 1.83 (d, J=3.28 Hz, 2H) 2.25 (d, J=6.82 Hz, 2H) 2.51-2.54 (m, 1H) 3.61 (s, 3H) 7.31 (dd, J=8.72, 3.16 Hz, 4H) 7.55-7.61 (m, 2H) 7.86 (d, J=8.59 Hz, 1H) 7.94 (d, J=8.34 Hz, 2H) 8.02 (dd, J=8.72, 2.65 Hz, 1H) 8.66 (d, J=2.78 Hz, 1H) 8.99 (s, 1H) 9.05 (s, 1H).

To 210 mg (0.4 mmol) [4-(4-{5-[3-(4-Trifluoromethoxy-phenyl)-ureido]-pyridin-2-yl}-phenyl)-cyclohexyl]-acetic acid methyl ester in THF/H$_2$O (10 mL; 4:1), 5 mL (4M) aqueous Lithium Hydroxide solution was added and the mixture stirred at 60° C. for 5 hours. Acidified with concentrated hydrochloric acid which precipitated the desired compound. Filtered and dried under vacuum to afford [4-(4-{5-[3-(4-Trifluoromethoxy-phenyl)-ureido]-pyridin-2-yl}-phenyl)-cyclohexyl]-acetic acid, which was subsequently dissolved in methanol (5 mL) one equivalent of potassium hydroxide and 2 mL of H$_2$O were added and the resulting mixture was stirred at 40° C. for 2 hours. Evaporated to dryness to afford [4-(4-{5-[3-(4-Trifluoromethoxy-phenyl)-ureido]-pyridin-2-yl}phenyl)-cyclohexyl]-acetic acid as the potassium salt: $^1$H NMR (400 MHz, MeOD) δ ppm 1.03-1.14 (m, 2H) 1.45 (td, J=12.57, 9.98 Hz, 2H) 1.75-1.87 (m, 5H) 2.03 (d, J=7.07 Hz, 2H) 2.37-2.47 (m, 1H) 7.12 (d, J=8.34 Hz, 2H) 7.21 (d, J=8.34 Hz, 2H) 7.43-7.51 (m, 2H) 7.64-7.73 (m, 3H) 7.96 (dd, J=8.72, 2.65 Hz, 1H) 8.58 (d, J=2.27 Hz, 1H); (M+H)+514.2.

Using analogous procedures to those described above, the following compounds may also be prepared:

| Example # | Name | LC rt | Method | (M + H)+ |
| --- | --- | --- | --- | --- |
| Ex. 5-26 | {4-[4-(5-Acetylamino-pyridin-2-yl)-phenyl]-cyclohexyl}-acetic acid | 1.11 | A | 353.2 |
| Ex. 5-27 | (4-{4-[5-(3-Trifluoromethyl-benzoylamino)-pyridin-2-yl]-phenyl}-cyclohexyl)-acetic acid | 1.53 | A | 483.2 |
| Ex. 5-28 | [4-(4-{5-[(Pyridine-2-carbonyl)-amino]-pyridin-2-yl}-phenyl)-cyclohexyl]-acetic acid | 1.4 | A | 416.2 |
| Ex. 5-29 | [4-(4-{5-[3-(2-Trifluoromethyl-phenyl)-ureido]-pyridin-2-yl}-phenyl)-cyclohexyl]-acetic acid | 12.9 | D | 498.2 |
| Ex. 5-30 | (4-{4-[5-(3-o-Tolyl-ureido)-pyridin-2-yl]-phenyl}-cyclohexyl)-acetic acid | 12 | D | 444.2 |
| Ex. 5-31 | [4-(4-{5-[(1-Methyl-1H-indole-3-carbonyl)-amino]-pyridin-2-yl}-phenyl)-cyclohexyl]-acetic acid | 12.5 | D | 468.2 |
| Ex. 5-32 | [4-(4-{5-[(1H-Indole-3-carbonyl)-amino]-pyridin-2-yl}-phenyl)-cyclohexyl]-acetic | 11.9 | D | 454.2 |
| Ex. 5-33 | [4-(4-{5-[(Pyridine-3-carbonyl)-amino]-pyridin-2-yl}-phenyl)-cyclohexyl]-acetic acid | 9.8 | D | 416.1 |
| Ex. 5-34 | [4-(4-{5-[(6-Methyl-pyridine-3-carbonyl)-amino]-pyridin-2-yl}-phenyl)-cyclohexyl]-acetic acid | 9.6 | D | 430.1 |
| Ex. 5-35 | [4-(4-{5-[(5-Bromo-pyridine-3-carbonyl)-amino]-pyridin-2-yl}-phenyl)-cyclohexyl]-acetic acid | 12 | D | 495.8 |
| Ex. 5-36 | [4-(4-{5-[(5-Chloro-6-methoxy-pyridine-3-carbonyl)-amino]-pyridin-2-yl}-phenyl)-cyclohexyl]-acetic acid | 1.42 | A | 480 |
| Ex. 5-37 | [4-(4-{5-[(5-Isobutyl-isoxazole-3-carbonyl)-amino]-pyridin-2-yl}-phenyl)-cyclohexyl]-acetic acid | 13.9 | D | 462.1 |
| Ex. 5-38 | [4-(4-{5-[(3-tert-Butyl-1-methyl-1H-pyrazole-4-carbonyl)-amino]-pyridin-2-yl}-phenyl)-cyclohexyl]-acetic acid | 13.2 | D | 475.2 |
| Ex. 5-39 | [4-(4-{5-[(5-tert-Butyl-1H-pyrazole-3-carbonyl)-amino]-pyridin-2-yl}-phenyl)-cyclohexyl]-acetic acid | 12.3 | D | 461.2 |
| Ex. 5-40 | [4-(4-{5-[(5-Isopropyl-isoxazole-3-carbonyl)-amino]-pyridin-2-yl}-phenyl)-cyclohexyl]-acetic acid | 13.2 | D | 448.2 |
| Ex. 5-41 | {4-[4-(5-Isobutoxycarbonylamino-pyridin-2-yl)-phenyl]-cyclohexyl}-acetic acid | 12.4 | D | 411.1 |
| Ex. 5-42 | [4-(4-{5-[((S)-5-Oxo-pyrrolidine-2-carbonyl)-amino]-pyridin-2-yl}-phenyl)-cyclohexyl]-acetic acid | 9.4 | D | 422.1 |
| Ex. 5-43 | (4-{4-[5-(4-Fluoro-3-trifluoromethyl-benzoylamino)-pyridin-2-yl]-phenyl}-cyclohexyl)-acetic acid | 1.51 | A | 501.2 |
| Ex. 5-44 | (4-{4-[5-(4-Trifluoromethyl-benzoylamino)-pyridin-2-yl]-phenyl}-cyclohexyl)-acetic acid | 1.49 | A | 482.9 |
| Ex. 5-45 | [4-(4-{5-[(6-Trifluoromethyl-pyridine-3-carbonyl)-amino]-pyridin-2-yl}-phenyl)-cyclohexyl]-acetic acid | 1.39 | A | 483.9 |
| Ex. 5-46 | (4-{4-[5-(3-Fluoro-5-trifluoromethyl-benzoylamino)-pyridin-2-yl]-phenyl}-cyclohexyl)-acetic acid | 1.56 | A | 501 |
| Ex. 5-47 | [4-(4-{5-[(Tetrahydro-pyran-4-carbonyl)-amino]-pyridin-2-yl}-phenyl)-cyclohexyl]-acetic acid | 1.12 | A | 422.9 |
| Ex. 5-48 | [4-(4-{5-[(5-Bromo-2-methoxy-pyridine-3-carbonyl)-amino]-pyridin-2-yl}-phenyl)-cyclohexyl]-acetic acid | 1.55 | A | 523.9 |
| Ex. 5-49 | [4-(4-{5-[(1,5-Dimethyl-1H-pyrazole-3-carbonyl)-amino]-pyridin-2-yl}-phenyl)-cyclohexyl]-acetic acid | 1.24 | A | 432.9 |
| Ex. 5-50 | [4-(4-{5-[(5-Methoxy-1H-indole-3-carbonyl)-amino]-pyridin-2-yl}-phenyl)-cyclohexyl]-acetic acid | 11.9 | D | 484.1 |

-continued

| Example # | Name | LC rt | Method | (M + H)+ |
|---|---|---|---|---|
| Ex. 5-51 | [4-(4-{5-[(2,5-Dimethyl-1H-pyrrole-3-carbonyl)-amino]-pyridin-2-yl}-phenyl)-cyclohexyl]-acetic acid | 11.3 | D | 432.1 |
| Ex. 5-52 | [4-(4-{5-[(1-Methyl-5-trifluoromethyl-1H-pyrazole-4-carbonyl)-amino]-pyridin-2-yl}-phenyl)-cyclohexyl]-acetic acid | 11.8 | D | 487 |
| Ex. 5-53 | {4-[4-(5-{[4-(Morpholine-4-sulfonyl)-1H-pyrrole-2-carbonyl]-amino}-pyridin-2-yl)-phenyl]-cyclohexyl}-acetic acid | 11.1 | D | 553.1 |
| Ex. 5-54 | (4-{4-[5-(2-Fluoro-2-methyl-propionylamino)-pyridin-2-yl]-phenyl}-cyclohexyl)-acetic acid | 1.15 | A | 398.9 |
| Ex. 5-55 | [4-(4-{5-[(1-Methyl-3-trifluoromethyl-1H-pyrazole-4-carbonyl)-amino]-pyridin-2-yl}-phenyl)-cyclohexyl]-acetic acid methyl ester | 13.5 | D | 501.2 |
| Ex. 5-56 | (4-{4-[5-(2-Methyl-2-pyrazol-1-yl-propionylamino)-pyridin-2-yl]-phenyl}-cyclohexyl)-acetic acid | 1.18 | A | 447.3 |
| Ex. 5-57 | [4-(4-{5-[(5-Isopropyl-isoxazole-4-carbonyl)-amino]-pyridin-2-yl}-phenyl)-cyclohexyl]-acetic acid | 12 | D | 448.3 |
| Ex. 5-58 | [4-(4-{5-[(1-Methyl-3-trifluoromethyl-1H-pyrazole-4-carbonyl)-amino]-pyridin-2-yl}-phenyl)-cyclohexyl]-acetic acid | 11.8 | D | 487.3 |
| Ex. 5-59 | [4-(4-{5-[(5-Cyclopropyl-isoxazole-4-carbonyl)-amino]-pyridin-2-yl}-phenyl)-cyclohexyl]-acetic acid | 3.2 | E | 446 |
| Ex. 5-60 | [4-(4-{5-[(5-Cyclopropyl-isoxazole-4-carbonyl)-amino]-pyridin-2-yl}-phenyl)-cyclohexyl]-acetic acid methyl ester | 13.7 | D | 460.2 |
| Ex. 5-61 | [4-(4-{5-[(5-Cyclopropyl-isoxazole-3-carbonyl)-amino]-pyridin-2-yl}-phenyl)-cyclohexyl]-acetic acid | 4.01 | E | 446 |
| Ex. 5-62 | [4-(4-{5-[(6-Methoxy-pyridine-3-carbonyl)-amino]-pyridin-2-yl}-phenyl)-cyclohexyl]-acetic acid | 1.26 | A | 446 |
| Ex. 5-63 | (4-{4-[5-(2,2-Dimethyl-butyrylamino)-pyridin-2-yl]-phenyl}-cyclohexyl)-acetic acid | 1.4 | A | 409 |
| Ex. 5-64 | (4-{4-[5-(2-Methoxy-2-methyl-propionylamino)-pyridin-2-yl]-phenyl}-cyclohexyl)-acetic acid | 1.17 | A | 411 |
| Ex. 5-65 | [4-(4-{5-[(1,5-Dimethyl-1H-pyrazole-4-carbonyl)-amino]-pyridin-2-yl}-phenyl)-cyclohexyl]-acetic acid | 3.58 | E | 433 |
| Ex. 5-66 | (4-{4-[5-(Tetrahydro-pyran-4-yloxycarbonylamino)-pyridin-2-yl]-phenyl}-cyclohexyl)-acetic acid | 3.35 | E | 439 |
| Ex. 5-67 | {4-[4-(5-Cyclopropylmethoxycarbonylamino-pyridin-2-yl)-phenyl]-cyclohexyl}-acetic acid | 3.61 | E | 409 |
| Ex. 5-68 | (4-{4-[5-(Tetrahydro-furan-2-ylmethoxycarbonylamino)-pyridin-2-yl]-phenyl}-cyclohexyl)-acetic acid | 3.35 | E | 439 |
| Ex. 5-69 | (4-{4-[5-(Tetrahydro-pyran-2-ylmethoxycarbonylamino)-pyridin-2-yl]-phenyl}-cyclohexyl)-acetic acid | 3.59 | E | 453.1 |
| Ex. 5-70 | (4-{4-[5-(3-Methyl-oxetan-3-ylmethoxycarbonylamino)-pyridin-2-yl]-phenyl}-cyclohexyl)-acetic acid | 3.36 | E | 439.1 |
| Ex. 5-71 | (4-{4-[5-(Tetrahydro-pyran-4-ylmethoxycarbonylamino)-pyridin-2-yl]-phenyl}-cyclohexyl)-acetic acid | 3.45 | E | 453.1 |
| Ex. 5-72 | (4-{4-[5-(2-Methyl-pyridin-3-ylmethoxycarbonylamino)-pyridin-2-yl]-phenyl}-cyclohexyl)-acetic acid | 3.47 | E | 460.1 |
| Ex. 5-73 | [4-(4-{5-[3-(4-Chloro-3-trifluoromethyl-phenyl)-ureido]-pyridin-2-yl}-phenyl)-cyclohexyl]-acetic acid | 4.41 | E | 532.2 |

Example 5-74

(4-{4-[5-(5-Methylsulfanyl-pyridin-2-ylamino)-pyridin-2-yl]-phenyl}-cyclohexyl)-acetic acid

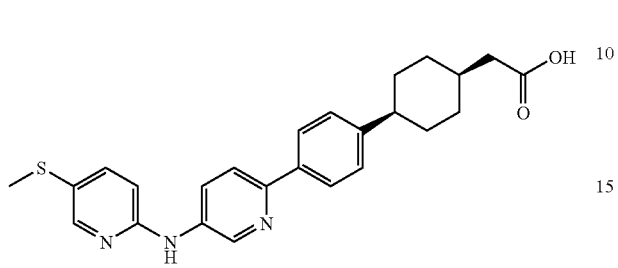

2-Bromo-5-methylsulfanyl-pyridine (51 mg, 0.25 mmol) and {4-[4-(5-Amino-pyridin-2-yl)-phenyl]-cyclohexyl}-acetic acid methyl ester (75 mg, 0.25 mmol) were dissolved in 1,4-dioxane (2 mL) in a pressure vessel. $Pd_2dba_3$ (7 mg, 0.008 mmol) and XANTPHOS (6 mg, 0.01 mmol) were added, followed by cesium carbonate (163 mg, 0.50 mmol). The mixture was sparged with nitrogen for 10 minutes, then the vessel was sealed and heated at 80° C. for 18 hours. The mixture was partitioned between EtOAc and water, then the organic layer was washed with brine, dried with magnesium sulfate, filtered, and concentrated via rotary evaporation. The crude material was used in the next step without further purification; MS (M+H)+448.3.

The crude (4-{4-[5-(5-Methylsulfanyl-pyridin-2-ylamino)-pyridin-2-yl]-phenyl}-cyclohexyl)-acetic acid methyl ester was dissolved in THF/MeOH (4:1, 2.5 mL) and to it was added aqueous LiOH (4M, 0.5 mL). The mixture was stirred at room temperature for 18 hours, then was immediately purified via reverse-phase HPLC to yield the title compound as a white solid: $^1$H NMR (400 MHz, DMSO-d6) δ ppm 1.08-1.20 (m, 2H) 1.44-1.57 (m, 2H) 1.84 (m, 5H) 2.16 (d, J=6.82 Hz, 2H) 2.50 (m, 1H) 6.91 (d, J=8.59 Hz, 1H) 7.36 (d, J=8.34 Hz, 2H) 7.70 (dd, J=8.59, 2.53 Hz, 1H) 7.91 (d, J=8.34 Hz, 2H) 7.95 (d, J=8.84 Hz, 1H) 8.21 (d, J=2.27 Hz, 1H) 8.33 (dd, J=9.09, 2.53 Hz, 1H) 8.98 (br. s., 1H) 9.64 (br. s., 1H); MS (M+H)+434.2.

Example 5-75

((4-{4-[5-(5-Trifluoromethyl-[1,3,4]oxadiazol-2-ylamino)-pyridin-2-yl]-phenyl}-cyclohexyl)-acetic acid)

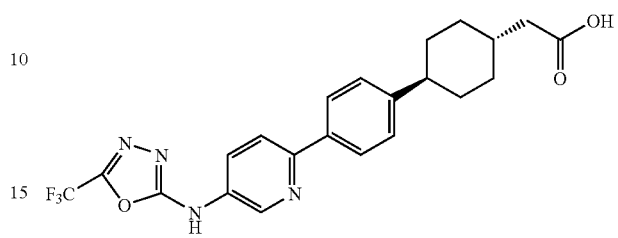

128 mg of trifluoroacetyl hydrazide was stirred in 3 ml of DMF and treated with 178 mg of thiocarbonyl diimidazole at room temperature. It was stirred for 3 hours and analyzed by LC-MS. The crude reaction mixture was then treated with 330 mg of {4-[4-(5-Amino-pyridin-2-yl)-phenyl]-cyclohexyl}-acetic acid methyl ester and stirred overnight at room temperature followed by heating at 60° C. for 8 hours. The reaction was analyzed by LC-MS which indicated complete consumption of the starting material. This crude reaction mixture was treated with 100 mg of EDCl at 60° C. and stirred overnight at the same temperature. The reaction was then cooled to room temperature and diluted with water. The resulting precipitates were collected by filtration and purified by column chromatography using hepthane and ethyl acetate as its eluents to afford ((4-{4-[5-(5 trifluoromethyl-[1,3,4] oxadiazol-2-ylamino)-pyridin-2-yl]-phenyl}-cyclohexyl)-acetic acid methyl ester. The whole material was taken for the next hydrolysis step and dissolved in 4 ml of THF and water (1:1 mixture). 80 mg of LiOH was added and the reaction was stirred at room temperature for 24 hours. LCMS indicated the reaction was completed. The reaction mixture was then neutralized with 6N—HCl and the resulting precipitates were triturated in hepthane and ethyl acetate 1:1 mixture and collected by filtration. The creamy filter cake was dried by air in the suction funnel to afford the title compound: $^1$H-NMR (400 MHz, DMSO-d$_6$, δ ppm 1.17 (br. s., 1H) 1.14 (d, J=12.38 Hz, 2H) 1.49 (d, J=10.36 Hz, 3H) 1.82 (br. s., 5H) 2.15 (d, J=6.82 Hz, 2H) 7.31 (d, J=8.59 Hz, 2H) 7.92 (t, J=9.09 Hz, 3H) 8.07 (dd, J=8.72, 2.65 Hz, 1H) 8.67 (d, J=2.53 Hz, 1H); LCMS (M+H)+=447.2.

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt.

Using analogous procedures to those described above, the following compounds may also be prepared:

| Example | Name | LC rt | Method | (M + H)+ |
|---|---|---|---|---|
| Ex. 5-76 | (4-{4-[5-(5-Fluoro-pyridin-3-ylamino)-pyridin-2-yl]-phenyl}-cyclohexyl)-acetic acid | 11.1 | D | 406.2 |
| Ex. 5-77 | (4-{4-[5-(6-Isopropoxy-pyridin-3-ylamino)-pyridin-2-yl]-phenyl}-cyclohexyl)-acetic acid | 1.49 | A | 446.2 |
| Ex. 5-78 | (4-{4-[5-(5-Bromo-pyridin-2-ylamino)-pyridin-2-yl]-phenyl}-cyclohexyl)-acetic acid | 1.51 | A | 468.1 |
| Ex. 5-79 | (4-{4-[5-(2-Methoxy-pyrimidin-5-ylamino)-pyridin-2-yl]-phenyl}-cyclohexyl)-acetic acid | 1.21 | A | 419.1 |

-continued

| Example | Name | LC rt | Method | (M + H)+ |
|---|---|---|---|---|
| Ex. 5-80 | (4-{4-[5-(6-Methylsulfanyl-pyridin-3-ylamino)-pyridin-2-yl]-phenyl}-cyclohexyl)-acetic acid | 11.2 | D | 434.3 |
| Ex. 5-81 | (4-{4-[5-([1,2,4]Triazin-3-ylamino)-pyridin-2-yl]-phenyl}-cyclohexyl)-acetic acid | 7.6 | D | 390.2 |
| Ex. 5-82 | (4-{4-[5-(2-Dimethylamino-pyrimidin-5-ylamino)-pyridin-2-yl]-phenyl}-cyclohexyl)-acetic acid | 1.3 | A | 432.2 |
| Ex. 5-83 | (4-{4-[5-(3,5-Difluoro-pyridin-2-ylamino)-pyridin-2-yl]-phenyl}-cyclohexyl)-acetic acid | 0.87 | B | 424.1 |
| Ex. 5-84 | (4-{4-[5-(6-Trifluoromethyl-pyridin-3-ylamino)-pyridin-2-yl]-phenyl}-cyclohexyl)-acetic acid methyl ester | 1.72 | A | 470.2 |
| Ex. 5-85 | (4-{4-[5-(5-Chloro-6-methoxy-pyridin-3-ylamino)-pyridin-2-yl]-phenyl}-cyclohexyl)-acetic acid | 1.5 | A | 452.1 |
| Ex. 5-86 | (4-{4-[5-(5-Fluoro-4-methyl-pyridin-2-ylamino)-pyridin-2-yl]-phenyl}-cyclohexyl)-acetic acid | 0.89 | B | 420.1 |
| Ex. 5-87 | (4-{4-[5-(3-Chloro-5-methyl-pyridin-2-ylamino)-pyridin-2-yl]-phenyl}-cyclohexyl)-acetic acid | 1.62 | A | 436.2 |
| Ex. 5-88 | (4-{4-[5-(5-Difluoromethyl-6-methoxy-pyridin-3-ylamino)-pyridin-2-yl]-phenyl}-cyclohexyl)-acetic acid | 1.41 | A | 468.1 |
| Ex. 5-89 | (4-{4-[5-(5-Methanesulfonyl-pyridin-2-ylamino)-pyridin-2-yl]-phenyl}-cyclohexyl)-acetic acid | 1.1 | A | 466.2 |
| Ex. 5-90 | (4-{4-[3-Fluoro-5-(6-trifluoromethyl-pyridin-3-ylamino)-pyridin-2-yl]-phenyl}-cyclohexyl)-acetic acid | 1.48 | A | 474.1 |
| Ex. 5-91 | (4-{4-[5-(1H-Benzoimidazol-2-ylamino)-pyridin-2-yl]-phenyl}-cyclohexyl)-acetic acid | 10.8 | D | 427.1 |
| Ex. 5-92 | (4-{4-[5-(6-Methyl-benzooxazol-2-ylamino)-pyridin-2-yl]-phenyl}-cyclohexyl)-acetic acid | 4.43 | E | 442 |
| Ex. 5-93 | (4-{4-[5-(2-Methyl-5-trifluoromethyl-2H-pyrazol-3-ylamino)-pyridin-2-yl]-phenyl}-cyclohexyl)-acetic acid | 1.42 | A | 459 |
| Ex. 5-94 | (4-{4-[5-(6-Chloro-benzooxazol-2-ylamino)-pyridin-2-yl]-phenyl}-cyclohexyl)-acetic acid methyl ester | 15.4 | D | 476.1 |
| Ex. 5-95 | (4-{4-[5-(6-Chloro-benzooxazol-2-ylamino)-pyridin-2-yl]-phenyl}-cyclohexyl)-acetic acid | 13.6 | D | 462 |
| Ex. 5-96 | (4-{4-[5-(5-Chloro-6-methoxy-benzooxazol-2-ylamino)-pyridin-2-yl]-phenyl}-cyclohexyl)-acetic acid | 13.4 | D | 492.2 |
| Ex. 5-97 | (4-{4-[5-(5-tert-Butyl-[1,3,4]oxadiazol-2-ylamino)-pyridin-2-yl]-phenyl}-cyclohexyl)-acetic acid | 13 | D | 435 |

Example 5-98

(4-{4-[5-(4-Trifluoromethyl-benzenesulfonylamino)-pyridin-2-yl]-phenyl}-cyclohexyl)-acetic acid

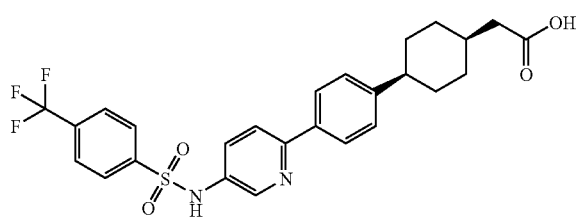 [SMILES: O=C(O)C[C@H]1CC[C@@H](c2ccc(-c3ccc(NS(=O)(=O)c4ccc(C(F)(F)F)cc4)cn3)cc2)CC1]

(4-{4-[5-(4-Trifluoromethyl-benzenesulfonylamino)-pyridin-2-yl]-phenyl}-cyclohexyl)-acetic acid methyl ester. To a solution of 0.300 g (0.925 mmol) of {4-[4-(5-Amino-pyridin-2-yl)-phenyl]-cyclohexyl}-acetic acid methyl ester, and 8 mL of dichloromethane was added 0.112 mL (1.39 mmol) of pyridine, 0.271 g (1.11 mmol) of 4-Trifluoromethyl-benzenesulfonyl chloride and 0.004 g (0.0277 mmol) DMAP. The dark orange solution was stirred at r.t. for 4 h. The mixture was extracted with dichloromethane, then washed with water, 1 N HCl, and brine. Dried with Na$_2$SO$_4$. Purified on silica gel (EtOAc/Heptane, 9:1 to 6:4) to afford the title compound. 1H NMR (400 MHz, CHLOROFORM-d$_6$) 0.99-1.10 (m, 2H) 1.34-1.46 (m, 2H) 1.71-1.82 (m, 5H) 2.14 (d, J=6.82 Hz, 2H) 2.39 (tt, J=-12.16, 3.25 Hz, 1H) 3.57 (s, 3H) 7.16 (d, J=8.34 Hz, 2H) 7.54 (dd, J=2.53, 1.77 Hz, 2H) 7.61 (d, J=8.34 Hz, 2H) 7.73 (d, J=8.34 Hz, 2H) 7.78 (d, J=8.08 Hz, 2H) 8.14 (dd, J=2.27, 1.01 Hz, 1'H).

(4-{4-[5-(4-Trifluoromethyl-benzenesulfonylamino)-pyridin-2-yl]-phenyl}-cyclohexyl)-acetic acid. To a solution of 0.136 g (0.256 mmol) of (4-{4-[5-(4-Trifluoromethyl-benzenesulfonylamino)-pyridin-2-yl]-phenyl}-cyclohexyl)-acetic acid methyl ester in THF/MeOH (4:1) was added 0.500 mL of LiOH (4 M) and let stir at r.t. for 72 h. Removed solvent in vacuo. The residue was taken up in water, brought to pH 4 and the solid filtered to afford the title compound. 1H NMR (400 MHz, DMSO d6) δ ppm 1.20-1.31 (m, 2H) 1.55-1.66 (m, 2H) 1.81-1.89 (m, 1H) 1.92-1.97 (m, 4H) 2.27 (d, J=6.82 Hz, 2H) 7.43 (d, J=8.34 Hz, 2H) 7.69 (dd, J=8.59, 2.78 Hz, 1H) 7.97 (d, J=8.59 Hz, 1H) 8.02 (d, J=8.34 Hz, 2H) 8.12 (m, 4H) 8.47 (d, J=0.51 Hz, 1H) 10.96 (br. s., 1H) 12.13 (br. s., 1H); (M+H)+=519.1.

Using analogous procedures, the following compounds may also be prepared:

| Example | Name | LC rt | Method | (M + H)+ |
|---|---|---|---|---|
| Ex. 5-99 | (4-{4-[5-(3-Trifluoromethyl-benzenesulfonylamino)-pyridin-2-yl]-phenyl}-cyclohexyl)-acetic acid | 1.48 | A | 519.2 |
| Ex. 5-100 | (4-{4-[5-(1,2-Dimethyl-1H-imidazole-4-sulfonylamino)-pyridin-2-yl]-phenyl}-cyclohexyl)-acetic acid | 1.07 | A | 469 |

Example 6-1

(4-{4-[6-(3-Chloro-phenylamino)-pyridazin-3-yl]-phenyl}-cyclohexyl)-acetic acid

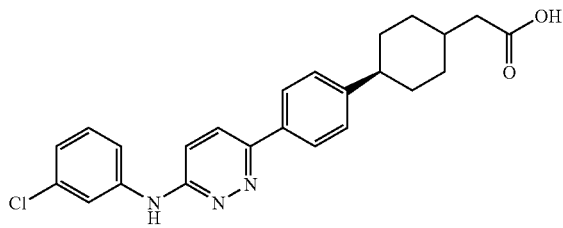

A. [4-(4-Acetyl-phenyl)-cyclohexyl]-acetic acid ethyl ester

To a 0° C. solution of (4-phenyl-cyclohexyl)-acetic acid ethyl ester (15 g, 61 mmol, 1.0 equiv) in 200 Ml DCM was added aluminum trichloride (16 g, 122 mmol, 2.0 equiv) portionwise over 15 min. Acetyl chloride (4.7 Ml, 67 mmol, 1.10 equiv) was then added dropwise via syringe. The homogeneous solution was allowed to stir at 0° C. for 2 h, then carefully quenched with 300 Ml ice water. The mixture was extracted with DCM (3×150 Ml), and the organic extracts were washed with saturated bicarbonate and brine solution. Removal of solvent in vacuo afforded the title compound: $^1$H NMR (400 MHz, CHLOROFORM-d) δ ppm 1.10 (q, J=11.96 Hz, 2H) 1.20 (t, J=7.20 Hz, 3H) 1.40-1.51 (m, 2H) 1.84 (d, J=11.12 Hz, 4H) 1.76-1.87 (m, 1H) 2.17 (d, J=6.82 Hz, 2H) 2.50 (s, 3H) 4.07 (q, J=7.07 Hz, 2H) 7.22 (d, J=8.34 Hz, 2H) 7.81 (d, J=8.08 Hz, 2H); (M+H)+289.1.

B. {4-[4-(6-Oxo-1,6-dihydro-pyridazin-3-yl)-phenyl]-cyclohexyl}-acetic acid ethyl ester To a solution of [4-(4-acetyl-phenyl)-cyclohexyl]-acetic acid ethyl ester (17 g, 59 mmol, 1.0 equiv) in 100 Ml glacial acetic acid was added glyoxylic acid monohydrate (5.4 g, 59 mmol, 1.0 equiv) as a solid. The solution was heated to 100° C. for 2 h. The mixture was then cooled to 40° C., then 75 Ml water was added followed by 120 Ml of a 28% ammonium hydroxide solution until the Ph was measured to be 8. Hydrazine (2.0 Ml, 65 mmol, 1.1 equiv) was then added via syringe, and the reaction was then heated to 95° C. for 2 hr. Upon cooling to room temperature, a solid precipitate was filtered off to afford the title compound in addition to the unelimi- nated product {4-[4-(5-hydroxy-6-oxo-1,4,5,6-tetrahydro-pyridazin-3-yl)-phenyl]-cyclohexyl}-acetic acid ethyl ester. This mixture was taken into the next step without further purification. (M+H)+341.2.

C. {4-[4-(6-Chloro-pyridazin-3-yl)-phenyl]-cyclohexyl}-acetic acid ethyl ester

A 50 Ml flask was charged with {4-[4-(6-oxo-1,6-dihydro-pyridazin-3-yl)-phenyl]-cyclohexyl}-acetic acid ethyl ester (0.76 g, 2.2 mmol, 1.0 equiv) in 20 Ml toluene followed by phosphorous oxychloride (0.62 Ml, 6.7 mmol, 3.0 equiv). The suspension was heated to 100° C., at which point a homogeneous solution ensued. The reaction was stirred overnight at 100° C., then cooled to room temperature. Removal of volatiles in vacuo afforded the title compound: 1H NMR (400 MHz, CHLOROFORM-d) δ ppm 1.07-1.17 (m, 2H) 1.20 (t, J=7.07 Hz, 3H) 1.43-1.53 (m, 2H) 1.78-1.90 (m, 5H) 2.18 (d, J=6.57 Hz, 2H) 2.44-2.52 (m, 1H) 4.08 (q, J=7.07 Hz, 2H) 7.29 (d, J=8.34 Hz, 2H) 7.46 (d, J=9.09 Hz, 1H) 7.72 (d, J=9.09 Hz, 1H) 7.90 (d, J=8.59 Hz, 2H); (M+H)+359.

D. (4-{4-[6-(3-Chloro-phenylamino)-pyridazin-1-yl]-phenyl}-cyclohexyl)-acetic acid ethyl ester To a suspension of {4-[4-(6-chloro-pyridazin-3-yl)-phenyl]-cyclohexyl}-acetic acid ethyl ester (2.0 g, 5.6 mmol, 1.0 equiv) in 40 Ml dioxane was added 3-chloroaniline (0.70 Ml, 6.7 mmol, 1.2 equiv) followed by 2 Ml 4 N HCl in dioxane. The mixture was then heated to 100° C. overnight. The reaction was partitioned between EtOAc and saturated bicarbonate solution, and the organic extracts were then washed with brine and dried. Removal of solvent in vacuo afforded the title compound: 1H NMR (400 MHz, CHLOROFORM-d) δ ppm 1.07-1.17 (m, 2H) 1.21 (t, J=7.20 Hz, 0.3H) 1.42-1.53 (m, 2H) 1.86 (t, J=10.99 Hz, 4H) 1.78-1.90 (m, 1H) 2.18 (d, J=6.57 Hz, 2H) 2.47 (td, J=12.00, 3.03 Hz, 1H) 4.08 (q, J=7.24 Hz, 2H) 7.03 (d, J=7.58 Hz, 1H) 7.26 (d, J=8.08 Hz, 3H) 7.20-7.28 (m, 2H) 7.45 (s, 1H) 7.68 (d, J=9.35 Hz, 1H) 7.84 (d, J=8.34 Hz, 2H); (M+H)+450.2.

E. 4-{4-[6-(3-Chloro-phenylamino)-pyridazin-3-yl]-phenyl}-cyclohexyl)-acetic acid To a solution of (4-{4-[6-(3-chloro-phenylamino)-pyridazin-3-yl]-phenyl}cyclohexyl)-acetic acid ethyl ester (1.8 g) in 50 Ml THF/EtOH (4:1) was added 5 Ml of 10% LiOH. The reaction was allowed to stir at 50° C. for 3 h, then stirred overnight at room temperature. Acidification with concentrated HCl afforded a precipitate which was recrystallized from EtOH to afford the title compound: 1H NMR (400 MHz, DMSO-d6) δ ppm 1.00-1.10 (m, 2H) 1.37-1.48 (m, 2H) 1.61-1.71 (m, 1H) 1.76 (d, J=11.12 Hz, 4H) 2.05 (d, J=6.82 Hz, 2H) 6.92 (ddd, J=7.83, 2.02, 0.76 Hz, 1H) 7.14 (d, J=9.60 Hz, 1H) 7.28 (dd, J=8.21, 6.44 Hz, 3H) 7.49 (ddd, J=8.34, 2.02, 0.76 Hz, 1H) 7.91 (dd, J=16.55, 8.97 Hz, 3H) 8.10 (t, J=2.02 Hz, 1H) 9.52 (s, 1H); (M+H)+422.2.

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt.

Using the appropriate amine, the following compounds may also be prepared in similar fashion:

| Example | Chemical Name | LC rt | Method | MS (M + H)+ |
|---|---|---|---|---|
| Ex. 6-2 | (4-{4-[6-(3-Fluoro-phenylamino)-pyridazin-3-yl]-phenyl}-cyclohexyl)-acetic acid | 1.45 | A | 406.2 |
| Ex. 6-3 | {4-[4-(6-m-Tolylamino-pyridazin-3-yl)-phenyl]-cyclohexyl}-acetic acid | 1.35 | A | 402.2 |
| Ex. 6-4 | (4-{4-[6-(3-Trifluoromethyl-phenylamino)-pyridazin-3-yl]-phenyl}-cyclohexyl)-acetic acid | 1.45 | A | 456.1 |
| Ex. 6-5 | (4-{4-[6-(3-Methoxy-phenylamino)-pyridazin-3-yl]-phenyl}-cyclohexyl)-acetic acid | 1.28 | A | 418.2 |
| Ex. 6-6 | (4-{4-[6-(3-Cyano-phenylamino)-pyridazin-3-yl]-phenyl}-cyclohexyl)-acetic acid | 1.21 | A | 413.2 |
| Ex. 6-7 | (4-{4-[6-(2-Fluoro-phenylamino)-pyridazin-3-yl]-phenyl}-cyclohexyl)-acetic acid | 1.23 | A | 406.3 |
| Ex. 6-8 | (4-{4-[6-(4-Chloro-phenylamino)-pyridazin-3-yl]-phenyl}-cyclohexyl)-acetic acid | 1.35 | A | 422.2 |
| Ex. 6-9 | {4-[4-(6-p-Tolylamino-pyridazin-3-yl)-phenyl]-cyclohexyl}-acetic acid | 1.31 | A | 402.3 |
| Ex. 6-10 | (4-{4-[6-(4-Trifluoromethyl-phenylamino)-pyridazin-3-yl]-phenyl}-cyclohexyl)-acetic acid | 1.43 | A | 456.3 |
| Ex. 6-11 | (4-{4-[6-(3-Chloro-4-methoxy-phenylamino)-pyridazin-3-yl]-phenyl}-cyclohexyl)-acetic acid | 1.32 | A | 452.2 |
| Ex. 6-12 | (4-{4-[6-(3-Chloro-2-methyl-phenylamino)-pyridazin-3-yl]-phenyl}-cyclohexyl)-acetic acid | 1.38 | A | 436.2 |
| Ex. 6-13 | {4-[4-(6-Phenylamino-pyridazin-3-yl)-phenyl]-cyclohexyl}-acetic acid | 1.24 | A | 388.3 |
| Ex. 6-14 | (4-{4-[6-(3-Chloro-2-methoxy-phenylamino)-pyridazin-3-yl]-phenyl}-cyclohexyl)-acetic acid | 1.38 | A | 452.3 |
| Ex. 6-15 | (4-{4-[6-(2-Methoxy-phenylamino)-pyridazin-3-yl]-phenyl}-cyclohexyl)-acetic acid | 1.28 | A | 418.3 |
| Ex. 6-16 | (4-{4-[6-(4-Methoxy-phenylamino)-pyridazin-3-yl]-phenyl}-cyclohexyl)-acetic acid | 1.26 | A | 418.3 |
| Ex. 6-17 | (4-{4-[6-(6-Trifluoromethyl-pyridin-3-ylamino)-pyridazin-3-yl]-phenyl}-cyclohexyl)-acetic acid | 1.26 | A | 457.3 |
| Ex. 6-18 | (4-{4-[6-(4-Trifluoromethoxy-phenylamino)-pyridazin-3-yl]-phenyl}-cyclohexyl)-acetic acid | 1.46 | A | 472.4 |
| Ex. 6-19 | (4-{4-[6-(4-Fluoro-phenylamino)-pyridazin-3-yl]-phenyl}-cyclohexyl)-acetic acid | 1.34 | A | 406.2 |
| Ex. 6-20 | (4-{4-[6-(6-Amino-pyridin-3-ylamino)-pyridazin-3-yl]-phenyl}-cyclohexyl)-acetic acid | 0.94 | A | 404.3 |
| Ex. 6-21 | (4-{4-[6-(Methyl-m-tolyl-amino)-pyridazin-3-yl]-phenyl}-cyclohexyl)-acetic acid | 1.44 | A | 416.3 |
| Ex. 6-22 | [4-(4-{6-[(3-Chloro-phenyl)-methyl-amino]-pyridazin-3-yl}-phenyl)-cyclohexyl]-acetic acid | 1.46 | A | 436.1 |
| Ex. 6-23 | [4-(4-{6-[(3-Methoxy-phenyl)-methyl-amino]-pyridazin-3-yl}-phenyl)-cyclohexyl]-acetic acid | 1.39 | A | 432.2 |
| Ex. 6-24 | (4-{4-[6-(2-Methyl-6-trifluoromethyl-pyridin-3-ylamino)-pyridazin-3-yl]-phenyl}-cyclohexyl)-acetic acid | 1.36 | A | 471.1 |
| Ex. 6-25 | (4-{4-[6-(3-Chloro-2-methoxy-phenylamino)-pyridazin-3-yl]-phenyl}-cyclohexyl)-acetic acid | 1.38 | A | 452.3 |

Example 6-26

2-{4-[6-(3-Chloro-phenylamino)-pyridazin-3-yl]-benzoylamino}-3-methyl-butyric acid

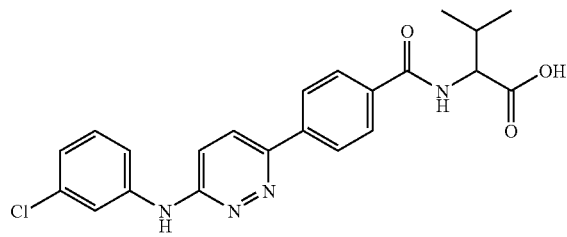 [SMILES: CC(C)C(NC(=O)c1ccc(-c2ccc(Nc3cccc(Cl)c3)nn2)cc1)C(=O)O]

A. 4-[6-(3-Chloro-phenylamino)-pyridazin-3-yl]-benzoic acid

To a slurry of 4-[6-chloro-pyradazin-3-yl]-benzoic acid (0.30 g, 1.3 mmol, 1.0 equiv) in 5 Ml dioxane was added 3-chloroaniline (0.15 Ml, 1.4 mmol, 1.1 equiv) followed by 4 M HCl in dioxane (0.34 Ml, 1.4 mmol, 1.0 equiv). The suspension was heated to 110° C. for 1 h. The cooled reaction was diluted with DCM, and the resulting precipitate was filtered to afford the title compound: $^1$H NMR (400 MHz, DMSO-d6) δ 6.90 (ddd, J=7.83, 2.02, 0.76 Hz, 1H) 7.13 (d, J=9.35 Hz, 1H) 7.23 (t, J=8.08 Hz, 1H) 7.45 (ddd, J=8.34, 2.02, 0.76 Hz, 1H) 7.91-7.95 (m, 2H) 8.00 (d, J=9.35 Hz, 1H) 8.03-8.08 (m, 3H) 9.56 (s, 1H) 12.90 (br. S., 1H); (M+H)+ 325.9.

B. 2-{4-[6-(3-Chloro-phenylamino)-pyridazin-3-yl]-benzoylamino}-3-methyl-butyric acid To a solution of 4-[6-(3-Chloro-phenylamino)-pyridazin-3-yl]-benzoic acid (0.10 g, 0.31 mmol, 1.0 equiv) in 2 Ml DMF was added HATU (0.23 g, 0.62 mmol, 2.0 equiv) and N,N-diisopropylethylamine (0.27 Ml, 1.5 mmol, 5.0 equiv). Valine methyl ester (0.062 g, 0.37 mmol, 1.0 equiv) was added as a solid, and the homogeneous solution was allowed to stir at room temperature overnight. To the solution was then added 1 Ml 10% aqueous LiOH, and the mixture was then heated to 55° C. The reactions were then filtered and the purified by reverse-phase HPLC to afford the title compound: $^1$H NMR (400 MHz, MeOD) δ 0.96 (dd, J=9.35, 6.82 Hz, 6H) 2.21 (dq, J=12.13, 6.82 Hz, 1H) 4.41 (d, J=5.05 Hz, 1H) 6.91 (ddd, J=1.26 Hz, 2.02, 1.01 Hz, 1H) 7-21 (t, J=8.08 Hz, 1H) 7.17 (d, J=9.35 Hz, 1H) 7.48 (dd, J=9.22, 1.14 Hz, 1H) 7.88-8.02 (m, 7H); (M+H)+425.1.

Using the appropriate amino ester, the following compounds may also be prepared in similar fashion:

| Example | Chemical Name | LC rt | Method | MS (M + H)+ |
|---|---|---|---|---|
| Ex. 6-27 | (S)-1-{4-[6-(3-Chloro-phenylamino)-pyridazin-3-yl]-benzoyl}-pyrrolidine-2-carboxylic acid | 0.98 | A | 423.0 |
| Ex. 6-28 | (1S,2R)-2-{4-[6-(3-Chloro-phenylamino)-pyridazin-3-yl]-benzoylamino}-cyclopentanecarboxylic acid | 1.07 | A | 437.2 |
| Ex. 6-29 | 3-{4-[6-(3-Chloro-phenylamino)-pyridazin-3-yl]-benzoylamino}-propionic acid | 1.05 | A | 396.9 |
| Ex. 6-30 | (S)-3-{4-[6-(3-Chloro-phenylamino)-pyridazin-3-yl]-benzoylamino}-5-methyl-hexanoic acid | 1.21 | A | 453.2 |
| Ex. 6-31 | (1S,2R)-2-{4-[6-(3-Chloro-phenylamino)-pyridazin-3-yl]-benzoylamino}-cyclohexanecarboxylic acid | 1.13 | A | 451.2 |
| Ex. 6-32 | (S)-1-{4-[6-(3-Chloro-phenylamino)-pyridazin-3-yl]-benzoyl}-piperidine-2-carboxylic acid | 1.1 | A | 436.9 |

Example 6-33

2-{4-[6-(3-Chloro-phenylamino)-pyridazin-3-yl]-benzoylamino}-2-methyl-propionic acid

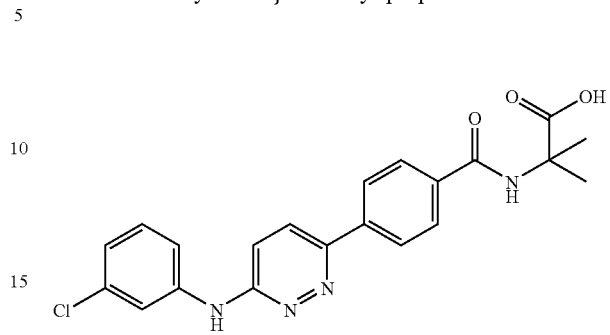

A. 4-(6-Chloro-pyridazin-3-yl)-benzoyl chloride

A suspension of 4-(6-chloro-pyradizin-3-yl)-benzoic acid (2.0 g, 8.5 mmol, 1.0 equiv) was suspended in excess thionyl chloride (30 Ml) and heated to reflux overnight. Removal of volatiles in vacuo afforded the title compound which was used without further purification: 1H NMR (400 MHz, CHLOROFORM-d) δ ppm 7.59 (d, J=8.84 Hz, 1H) 7.85 (d, J=9.09 Hz, 1H) 8.15 (d, J=8.00 Hz, 2H) 8.22 (d, J=8.00 Hz, 2H).

B. 2-[4-(6-Chloro-pyridazin-3-yl)-benzoylamino]-2-methyl-propionic acid

A solution of 4-(6-Chloro-pyridazin-3-yl)-benzoyl chloride (0.25 g, 1.0 mmol, 1.0 equiv) in 5 Ml THF and 3 Ml DMF was added to a vial containing 2-amino isobutyric acid (0.10 g, 1.0 mmol, 1.0 equiv) and 1 N NaOH (2 Ml, 2.0 mmol, 2.0 equiv). The homogeneous solution was allowed to stir overnight at room temperature. Acidification to Ph 1 using concentrated HCl afforded a precipitate which was filtered and used directly in the subsequent step.

C. 2-{4-[6-(3-Chloro-phenylamino)-pyridazin-3-yl]-benzoylamino}-2-methyl-propionic acid A 1-dram vial was charged with 3-chloroaniline (0.2 Ml, excess) and 2-[4-(6 chloro-pyridazin-3-yl)-benzoylamino]-

2-methyl-propionic acid (0.75 g) as a solid. The vial was heated to 100° C. for 1.5 h. The crude reaction mixture was then dissolved in 2 Ml DMF and then purified by reverse-phase preparative HPLC to afford the title compound: 1H NMR (400 MHz, DMSO-D6) δ ppm 1.47 (s, 6H), 7.03 (dd, J=7.45, 1.64 Hz, 1H), 7.28 (d, J=9.35 Hz, 1H), 7.36 (t, J=8.08 Hz, 1H), 7.56 (dd, J=8.34, 1.26 Hz, 1H), 7.99 (d, J=8.59 Hz, 2H), 8.12-8.19 (m, 4H), 8.52 (s, 1H), 9.71 (s, 1H); (M+H)+411.0.

Example 6-34

4-{4-[6-(3-Trifluoromethyl-phenylamino)-pyridazin-3-yl]-phenyl}-cyclohexanecarboxylic acid

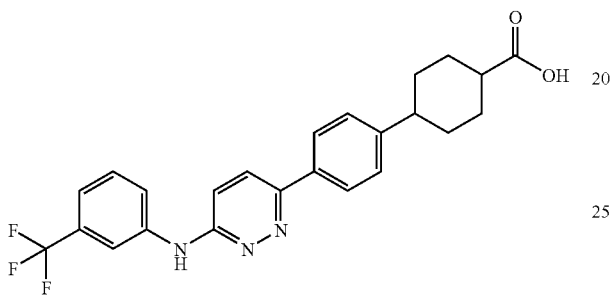

The synthesis of 4-phenyl-cyclohexanecarboxylic acid methyl ester has been reported in WO2004 047755. Starting from 4-phenyl-cyclohexanecarboxylic acid methyl ester, the sequence described for Ex. 6-1 was followed to afford the title compound as a mixture of diastereomers which were separated by reverse-phase preparative HPLC:
Diastereomer 1: ¹H NMR (400 MHz, DMSO-d6) δ 1.20-1.37 (m, 4H) 1.60-1.70 (m, 2H) 1.79 (d, J=10.86 Hz, 2H) 2.01-2.15 (m, 1H) 2.33 (m, 1H) 7.03 (d, J=9.35 Hz, 1H) 7.07 (d, J=7.58 Hz, 1H) 7.16 (d, J=8.34 Hz, 2H) 7.34 (t, J=8.21 Hz, 1H) 7.76 (d, J=8.34 Hz, 2H) 7.72 (d, J=7.83 Hz, 1H) 7.83 (d, J=9.35 Hz, 1H) 8.17 (s, 1H) 9.52 (s, 1H)
Diastereomer 2: ¹H NMR (400 MHz, DMSO-d6) 1.69-1.80 (m, 4H) 1.80-1.90 (m, 2H) 2.25 (m, m 2H) 2.75-2.80 (m, 2H) 7.37-7.47 (m, 4H) 7.69 (t, J=8.21 Hz, 1H) 8.11 (d, V-8.34 Hz, 2H) 8.08 (dd, J=8.46, 1.64 Hz, 1H) 8.17 (d, J=9.35 Hz, 1H) 8.52 (s, 1H) 9.86 (s, 1H); (M+H)+442.2.

Example 6-35

2-(4-{4-[6-(3-Chloro-phenylamino)-pyridazin-3-yl]-phenyl}-cyclohexyl)-acetamide

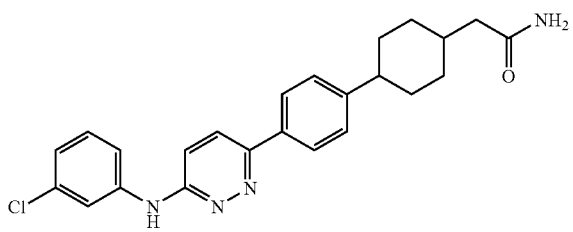 [SMILES: NC(=O)CC1CCC(c2ccc(-c3ccc(Nc4cccc(Cl)c4)nn3)cc2)CC1]

To a solution of Ex. 6-1 (0.10 g, 0.24 mmol, 1.0 equiv) in 3 Ml DMF was added HATU (0.10 g, 0.26 mmol, 1.1 equiv) followed by ammonium hydroxide (0.06 Ml of a 28% aqueous solution). The homogeneous reaction was allowed to stir at room temperature for 3 h. The reaction was then partitioned between EtOAc and water, and the organic extracts were washed with brine and dried. The crude residue was then purified by reverse-phase preparative. HPLC to afford the title compound: 1H NMR (400 MHz, DMSO-d6) δ ppm 1.06-1.17 (m, 2H) 1.44-1.54 (m, 2H) 1.72-1.77 (m, 1H) 1.82 (br. S., 2H) 1.84 (d, J=3.54 Hz, 2H) 1.99 (d, J=6.82 Hz, 2H) 2.52-2.57 (m, 1H) 6.71 (br. S., 1H) 7.01 (ddd, J=8.02, 2.08, 0.76 Hz, 1H) 7.22 (d, J=9.35 Hz, 1H) 7.33-7.38 (m, 3H) 7.57 (ddd, J=8.34, 2.02, 0.76 Hz, 1H) 7.99 (dd, J=17.43, 8.84 Hz, 3H) 8.18 (t, J=2.02 Hz, 1H) 9.57 (s, 1H); (M+H)+412.3.

Example 6-36

(6-{4-[4-(2H-Tetrazol-5-ylmethyl)-cyclohexyl]-phenyl}-pyridazin-3-yl)-6-trifluoromethyl-pyridin-3-yl)-amine

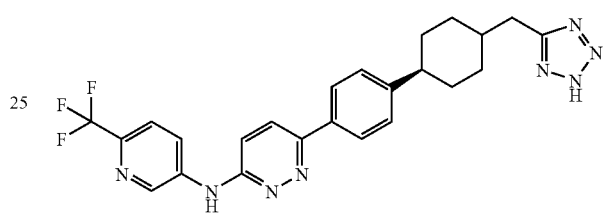

A. 2-(4-{4-[6-(6-Trifluoromethyl-pyridin-3-ylamino)-pyridazin-3-yl]-phenyl}-cyclohexyl)-acetamide Using Ex. 6-17 and the procedure described for Ex. 6-35 above, the title compound was produced and used in the subsequent step without further purification: (M+H)+456.3.

B. (4-{4-[6-(6-Trifluoromethyl-pyridin-3-yl-amino)-pyridazin-3-yl]-phenyl}-cyclohexyl)-acetonitrile To a mixture of 2-(4-{4-[6-(6-Trifluoromethyl-pyridin-3-ylamino)-pyridazin-3-yl]-phenyl}-cyclohexyl)-acetamide (0.18 g, 0.41 mmol, 1.0 equiv) in 3 Ml THF was added trifluoroacetic anhydride (0.068 Ml, 0.49 mmol, 1.2 equiv) followed by triethylamine (0.12 Ml, 0.90 mmol, 2.2 equiv). The reaction was stirred at ambient temperature overnight, and then concentrated in vacuo. Purification by silica gel chromatography (10-50% EtOAc in hexanes) afforded the title compound: 1H NMR (400 MHz, DMSO-d6) δ ppm 1.39-1.50 (m, J=12.82, 12.54, 12.54, 3.54 Hz, 2H) 1.69-1.80 (m, J=12.88, 12.69, 12.69, 3.41 Hz, 2H) 1.86-1.97 (m, J=11.91, 11.91, 6.06, 5.87, 2.91 Hz, 1H) 2.09 (d, J=15.92 Hz, 1H) 2.09 (dd, J=5.94, 3.66 Hz, 3H) 2.76 (t, J=3.03 Hz, 1H) 7.53 (d, J=9.35 Hz, 1H) 7.59 (d, J=8.34 Hz, 2H) 8.08 (d, J=8.59 Hz, 1H) 8.20 (d, J=8.34 Hz, 2H) 8.30 (d, J=9.35 Hz, 1H) 8.91 (dd, J=8.59, 2.27 Hz, 1H) 9.16 (d, J=2.53 Hz, 1H) 10.25 (s, 1H); (M+H)+438.3.

C. (6-{4-[4-(2H-Tetrazol-5-ylmethyl)-cyclohexyl]-phenyl}-pyridazin-3-yl)-6-trifluoromethyl-pyridin-4-yl))-amine To a mixture of (4-{4-[6-(6-Trifluoromethyl-pyridin-3-ylamino)-pyridazin-3-yl]-phenyl}-cyclohexyl)-acetonitrile (0.12 g, 0.29 mmol, 1.0 equiv) in 3 Ml DMF was added sodium azide (0.057 g, 0.88 mmol, 3.0 equiv), followed by solid ammonium chloride (0.062 g, 4.0 equiv). The reaction was heated to 140° C. over the weekend. The cooled reaction mixture was diluted with 10 Ml water and then acidified to Ph 4-5. The precipitate was filtered to afford the title compound: 1H NMR (400 MHz, DMSO-d6) δ ppm 103-1.16 (m, 2H) 1.33-1.45 (m, 2H) 1.73 (t, J=14.27 Hz, 5H) 2.60-2.68 (m, 3H) 7.27 (dd, J=17.94, 8.84 Hz, 3H) 7.79 (d, J=8.84 Hz, 1H) 7.86-7.95 (m, 2H) 8.01 (d, J=9.09 Hz, 1H) 8.63 (dd, J=8.59, 1.77 Hz, 1H) 8.87 (d, J=2.27 Hz, 1H) 9.99 (s, 1H); (M+H)+ 481.7.

Example 6-37

3-(4-{4-[6-(6-Trifluoromethyl-pyridin-3-ylamino)-pyridazin-3-yl]-phenyl}-cyclohexylmethyl)-4H-[1,2,4]oxadiazol-5-one

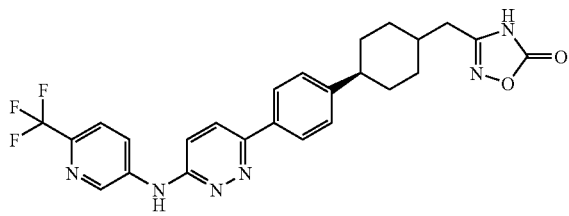

A. N-Hydroxy-2-(4-{4-[6-(6-trifluoromethyl-pyridin-3-ylamino)-pyridazin-3-yl]-phenyl}-cyclohexyl)-acetamidine To a solution of (4-{4-[6-(6-Trifluoromethyl-pyridin-3-ylamino)-pyridazin-3-yl]-phenyl}-cyclohexyl)-acetonitrile (0.15 g, 0.34 mmol, 1.0 equiv) in 4 Ml DMSO was added hydroxylamine hydrochloride (0.12 g, 1.7 mmol, 5.0 equiv) and triethylamine (0.25 Ml, 1.8 mmol, 5.2 equiv). The yellow solution was heated to 120° C. using microwave heating for 10 min. Additional portions of hydroxylamine hydrochloride and triethylamine were added, and the reaction was allowed to stir overnight at 75° C. The reaction was partitioned between EtOAc and water, and the organic extracts were washed with saturated NaHCO3 followed by brine. The organic layer was then dried over sodium sulphate, filtered, and concentrated in vacuo to afford the title compound which was used without further purification: (M+H)+471.2.

B. [1-[(Z)-Hydroxyimino]-2-(4-{4-[6-(6-trifluoromethyl-pyridin-3-ylamino)-pyridazin-3-yl]-phenyl}-cyclohexyl)-ethyl]-carbamic acid isobutyl ester To a solution of N-Hydroxy-2-(4-{4-[6-(6-trifluoromethyl-pyridin-3-ylamino)-pyridazin-3-yl]-phenyl}-cyclohexyl)-acetamidine (0.13 g, 0.28 mmol, 1.0 equiv) in 2 Ml DMF was added pyridine (0.023 Ml, 0.31 mmol, 1:1 equiv). The solution was cooled to 0° C., then isobutyl chloroformate (0.04 Ml, 0.31 mmol, 1.1 equiv) was added dropwise via syringe. The reaction was allowed to warm to room temperature and stirred for 2 h. Extractive aqueous workup afforded the title compound which was used in the next step without further purification. (M+H)+571.4.

C. 3-(4-{4-[6-(6-Trifluoromethyl-pyridin-3-ylamino)-pyridazin-3-yl]-phenyl}-cyclohexylmethyl)-4H-[1,2,4]oxadiazol-5-one A solution of [1-[(Z)-hydroxyimino]-2-(4-{4-[6-(6-trifluoromethyl-pyridin-3-ylamino)-pyridazin-3-yl]-phenyl}-cyclohexyl)-ethyl]-carbamic acid isobutyl ester (0.13 g, 0.23 mmol 1.0 equiv) was dissolved in a m-xylene/THF (4:1) mixture and then heated to 180° C. for 20 min. The cooled reaction was partitioned between EtOAc and water, and the organic layers were washed with brine and dried. Purification by silica gel chromatography (10-100% MeOH in DCM) afforded the title compound: 1H NMR (400 MHz, DMSO-d6) δ ppm 0.99-1.10 (m, 2H) 1.34 (q, J=11.79 Hz, 2H) 1.59 (ddd, J=11.12, 7.58, 4.04 Hz, 1H) 1.70 (t, J=14.02 Hz, 4H) 2.29 (d, J=6.82 Hz, 2H) 2.38-2.46 (m, 1H) 7.23 (d, J=8.08 Hz, 2H) 7.18 (d, J=9.35 Hz, 1H) 7.72 (d, J=8.59 Hz, 1H) 7.84 (d, J=8.08 Hz, 2H) 7.94 (d, J=9.35 Hz, 1H) 8.56 (dd, J=8.59, 1.26 Hz, 1H) 8.81 (d, J=1.77 Hz, 1H) 9.90 (s, 1H) 12.03 (br. S., 1H); (M+H)+497.2.

Example 6-38

(1-{4-[6-(3-Trifluoromethyl-phenylamino)-pyridazin-3-yl]-phenyl}-piperidin-4-yl)-acetic acid

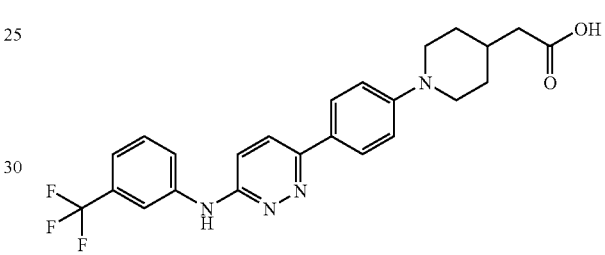

A. [1-(4-Acetyl-phenyl)-piperidin-4-yl]-acetic acid ethyl ester

A microwave vial was charged with 4'-fluoroacetophenone (1.2 Ml, 10.4 mmol, 1.0 equiv) and 2-(piperidin-4-yl)-acetic acid ethyl ester (3.5 g, 20.7 mmol, 2.0 equiv) in 20 Ml DMSO. The homogeneous reaction was heated to 150° C. for 20 min. The cooled reaction was then diluted with ether and washed sequentially with saturated ammonium chloride, water, and brine. The organic extracts were then dried over sodium sulphate, filtered, and concentrated in vacuo. Purification by flash chromatography (10-40% EtOAc in hexanes) afforded the title compound: 1H NMR (400 MHz, CHLOROFORM-d) δ ppm 1.32 (t, J=7.07 Hz, 3H) 1.47 (d, J=12.13 Hz, 2H) 1.62 (br.s., 1H) 1.90 (d, J=12.63 Hz, 2H) 2.04-2.15 (m, J=11.18, 11.18, 7.45, 7.45, 3.79, 3.66 Hz, 1H) 2.33 (d, J=7.07 Hz, 2H) 2.57 (s, 3H) 2.97 (td, J=12.57, 2.15 Hz, 2H) 3.93 (d, J=12.88 Hz, 2H) 4.20 (q, J=7.07 Hz, 2H) 6.96 (d, J=6.82 Hz, 2H) 7.92 (d, J=9.09 Hz, 2H); (M+H)+290.1.

B. (1-{4-[6-(3-Trifluoromethyl-phenylamino)-pyridazin-3-yl]-phenyl}-piperidin 4-yl)-acetic acid Starting from [1-(4-Acetyl-phenyl)-piperidin-4-yl]-acetic acid-ethyl ester, steps B-D from Ex. 6-1 were followed using 3-trifluoromethyl aniline to afford the title compound: 1H NMR (400 MHz, DMSO-d6) δ ppm 1.30 (td, J=11.94, 8.72 Hz, 2H) 1.79 (br. S., 1H) 1.76 (d, J=2.78 Hz, 1H) 1.86 (td, J=11.05, 4.17 Hz, 1H) 2.20 (d, J=6.82 Hz, 2H) 2.77 (t, J=11.37 Hz, 2H) 3.82 (d, J=12.63 Hz, 2H) 7.04 (d, J=8.84 Hz, 2H) 7.20 (d, J=9.35 Hz, 1H) 7.28 (d, J=7.83 Hz, 1H) 7.55 (t, J=7.96 Hz, 1H) 7.90-8.00 (m, 2H) 7.92 (d, J=8.84 Hz, 2H) 8.40 (s, 1H) 9.63 (s, 1H) 12.10 (br. S., 1H); (M+H)+457.3.

Example 6-39

(4-{4-[4-Methyl-6-(6-trifluoromethyl-pyridin-3-ylamino)-pyridazin-3-yl]-phenyl}-cyclohexyl)-acetic acid

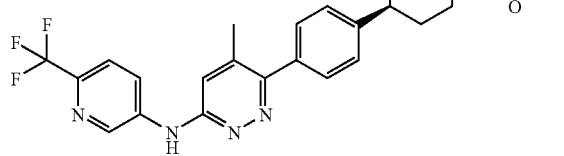

A. [4-(4-Propionyl-phenyl)-cyclohexyl]acetic acid-ethyl ester

Using proprionyl chloride in step A for Ex. 6-1, the title compound was synthesized in analogous fashion: 1H NMR (400 MHz, CHLOROFORM-d) δ ppm 1.11-1.22 (m, 8H) 1.40-1.51 (m, 2H) 1.84 (d, J=10.11 Hz, 4H) 2.10 (s, 1H) 2.17 (d, J=6.82 Hz, 2H) 2.41-2.51 (m, 1H) 2.90 (q, J=7.16 Hz, 2H) 4.08 (q, J=7.07 Hz, 2H) 7.21 (d, J=8.34 Hz, 2H) 7.82 (d, J=8.34 Hz, 2H).

B. (4-{4-[4-Methyl-6-(6-trifluoromethyl-pyridin-3-ylamino)-pyridazin-3-yl]-phenyl}-cyclohexyl)-acetic acid Starting from [4-(4-Propionyl-phenyl)-cyclohexyl]-acetic acid ethyl ester, steps B-D from Ex. 6-1 were followed using 6-trifluoromethyl-pyridin-3-ylamine to afford the title compound: 1H NMR (400 MHz, DMSO-d6) δ ppm 1.04-1.15 (m, 2H) 1.48 (m, 2H) 1.74 (m, J=10.99, 4.17 Hz, 1H) 1.85 (d, J=11.12 Hz, 4H) 1.99 (d, J=6.32 Hz, 2H) 2.30 (s, 3H) 7.20 (s, 1H) 7.34 (d, J=8.08 Hz, 2H) 7.49 (d, J=8.34 Hz, 2H) 7.84 (d, J=8.84 Hz, 1H) 8.67 (dd, J=8.59, 2.27 Hz, 1H) 8.98 (d, J=2.27 Hz, 1H) 10.27 (s, 1H); (M+H)+471.2.

Example 6-40

(4-{4-[4-Methyl-6-(4-trifluoromethyl-phenylamino)-pyridazin-3-yl]-phenyl}-cyclohexyl)-acetic acid The title compound was prepared in analogous fashion using 4-trifluoromethyl aniline: 1H NMR (400 MHz, DMSO-d6) δ ppm 1.10-1.21 (m, 2H) 1.47-1.58 (m, 2H) 1.71-1.80 (m, 1H) 1.86 (d, J=10.11 Hz, 4H) 2.16 (d, J=6.82 Hz, 2H) 2.29 (s, 3H) 2.56 (m, 1H) 7.11 (s, 1H) 7.35 (d, J=8.34 Hz, 2H) 7.51 (d, J=8.08 Hz, 2H) 7.66 (d, J=8.59 Hz, 2H) 7.99 (d, J=8.59 Hz, 2H) 9.67 (s, 1H) 12.01 (s, 1H); (M+H)+470.2.

Example 7

(4-{4-[5-(6-Trifluoromethyl-pyridin-3-ylamino)-pyrazin-2-yl]-phenyl}-cyclohexyl)-acetic acid

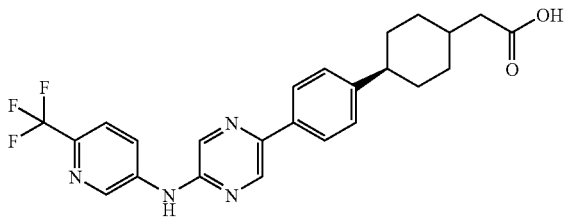

A. Pyrazin-2-yl-(6-trifluoromethyl-pyridin-3-yl)-amine

To a solution of 5-amino-2-trifluoromethylpyridine (0.81 g) in 3 Ml toluene was added chloropyrazine (0.45 Ml, 1.0 equiv) via syringe. The homogeneous solution was heated to 95° C., then cooled to room temperature and concentrated in vacuo. Purification by silica gel chromatography (40% EtOAc in hexanes) afforded the title compound: 1H NMR (400 MHz, CHLOROFORM-D) δ ppm 7.5 (s, 1H) 7.6 (s, 1H) 8.0 (s, 1H) 8.2 (s, 1H) 8.4 (s, 2H) 8.8 (s, 1H); (M+H)+241.1.

B. (5-Bromo-pyrazin-2-yl)-(6-trifluoromethyl-pyridin-3-yl)-amine

A solution of pyrazin-2-yl-(6-trifluoromethyl-pyridin-3-yl)-amine (0.47 g) was dissolved in 50 Ml MeOH and then charged with N-bromosuccinimide (0.35 g) in a single portion as a solid. The reaction was stirred overnight at room temperature, then concentrated in vacuo. Purification by silica gel chromatography (25% EtOAc in hexanes) afforded the title compound: 1H NMR (400 MHz, CHLOROFORM-D) δ ppm 6.7 (s, 1H) 7.5 (s, 1H) 7.9 (s, 1H) 8.2 (s, 2H) 8.6 (s, 1H); (M+H)+320.9.

C. (4-{4-[5-(6-Trifluoromethyl-pyridin-3-ylamino)-pyrazin-2-yl]-phenyl}-cyclohexyl)-acetic acid methyl ester A solution of (5-Bromopyrazin-2-yl)-(6-trifluoromethyl-pyridin-3-yl)-amine (0.072 g) and {4-[4-(5-bromo-pyridin-2-yl)-phenyl]-cyclohexyl}-acetic acid methyl ester (0.087 g) in 2 Ml DME was charged with 2 M sodium carbonate (1 Ml) and Pd(PPh3)4 (0.027 g, 0.1 equiv). The biphasic mixture was sparged with nitrogen for 3 min, then stirred at 130° C. under microwave heating for 30 min. The reaction was partitioned between EtOAc and water, and the organic extracts were dried over magnesium sulphate and concentrated in vacuo. Purification by silica gel chromatography (33% EtOAc in hexanes) afforded the title compound: (M+H)+ 471.2.

D. (4-{4-[5-(6-Trifluoromethyl-pyridin-3-ylamino)-pyrazin-2-yl]-phenyl}-cyclohexyl)-acetic acid To a solution of (4-{4-[5-(6-trifluoromethyl-pyridin-3-ylamino)-pyrazin-2-yl]-phenyl}-cyclohexyl)-acetic acid methyl ester (0.051 g) in 4 Ml THF/water (1:1) was added solid lithium hydroxide (0.030 g). The reaction was stirred at room temperature for 48 h. then heated to 45° C. for 24 h. The reaction was neutralized with 6 N hydrochloric acid and then purified by reverse-phase preparative HPLC to afford the title compound: 1H NMR (400 MHz, DMSO-D6) δ ppm 1.1 (s, 2H) 1.3 (s, 1H) 1.6 (s, 2H) 1.9 (s, 6H) 3.5 (s, 6H) 7.4 (s, 2H) 7.9 (s, 1H) 8.0 (s, 2H) 8.6 (s, 1H), 8.6 (s, 1H) 8.9 (s, 1H) 9.1 (s, 1H) 10.9 (s, 1H); (M+H)+457.1.

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt.

Example 8-1

(4-{4-[5-(6-Trifluoromethyl-pyridin-3-ylcarbamoyl)-pyridin-2-yl]-phenyl}-cyclohexyl)-acetic acid

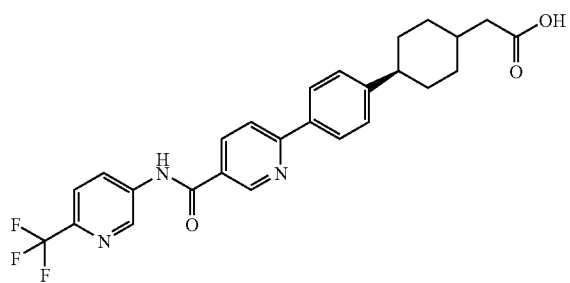

6-Trifluoromethyl-pyridin-3-ylamine (963 mg, 6 mmol) was dissolved in DCM (50 mL) 6-Bromo-nicotinic acid (1 g, 5 mmol) and N-(3-Dimethylaminopropyl)-N'-ethylcarbodiimide hydrochloride (1.9 g, 10 mmol) were added. Stirred overnight, evaporated to dryness and purified by passing over small plug of silica gel eluting with 30% ethyl acetate in hexanes to afford 6-Bromo-N-(6-trifluoromethyl-pyridin-3-yl)-nicotinamide: M+1=347.3. 1H NMR (400 MHz, DMSO-D6) δ ppm 7.91 (dd, J=19.83, 8.46 Hz, 2H) 8.26 (dd, J=8.34, 2.53 Hz, 1H) 8.46 (dd, J=8.34, 2.27 Hz, 1H) 8.95 (d, J=2.53 Hz, 1H) 9.06 (d, J=2.27 Hz, 1H) 11.00 (s, 1H).

To 200 mg (1 mmol) 6-Bromo-N-(6-trifluoromethyl-pyridin-3-yl)-nicotinamide, 217 mg (1 mmol) {4-[4-(4,4,5,5-Tetramethyl-[1,3,2]dioxaborolan-2-yl)-phenyl]-cyclohexyl}-acetic acid methyl ester in DME (20 mL), Dichloro[1,1'-bis(diphenylphosphino)ferrocene]palladium (II) dichloromethane adduct (37 mg, 5 mol %), and saturated sodium carbonate aqueous solution (2 mL) were added and the mixture stirred at 80° C. over night under $N_2$. Evaporated to dryness and purified by passing over small plug of silica gel (30% ethyl acetate in hexanes) to afford (4-{4-[5-(6-Trifluoromethyl-pyridin-3-ylcarbamoyl)-pyridin-2-yl]-phenyl}-cyclohexyl)-acetic acid methyl ester: M+1=498.1. $^1$H NMR (400 MHz, DMSO-D6) δ ppm 1.06 (s, 4H) 1.12-1.20 (m, 2H) 1.45-1.57 (m, 2H) 1.81 (d, J=8.59 Hz, 4H) 2.25 (d, J=6.57 Hz, 2H) 2.50-2.57 (m, 1H) 3.60 (s, 2H) 7.39 (d, J=8.34 Hz, 2H) 7.94 (d, J=8.84 Hz, 1H) 8.07-8.15 (m, 2H) 8.35-8.43 (m, 1H) 8.50 (d, J=8.59 Hz, 1H) 9.10 (s, 1H) 9.20 (d, J=2.02 Hz, 1H).

To 60 mg (0.1 mmol), (4-{4-[5-(6-Trifluoromethyl-pyridin-3-ylcarbamoyl)-pyridin-2-yl]-phenyl}-cyclohexyl)-acetic acid methyl ester in THF/$H_2O$ (10 mL; 4:1), 5 mL (4M) aqueous Lithium Hydroxide solution was added and the mixture stirred at 60° C. for 5 hours. Acidified with concentrated hydrochloric acid which precipitated the desired compound. Filtered and dried under vacuum to afford (4-{4-[5-(6-Trifluoromethyl-pyridin-3-ylcarbamoyl)-pyridin-2-yl]-phenyl}-cyclohexyl)-acetic acid, which was subsequently dissolved in methanol (5 mL) one equivalent of potassium hydroxide and 2 mL of $H_2O$ were added and the resulting mixture was stirred at 40 C for 2 hours. Evaporated to dryness to afford (4-{4-[5-(6-Trifluoromethyl-pyridin-3-ylcarbamoyl)-pyridin-2-yl]-phenyl}-cyclohexyl)-acetic acid as the potassium salt: M+1=484.1. HRMS=484.1822. $^1$H NMR (400 MHz, MeOD) δ ppm 0.79 (d, J=7.33 Hz, 1H) 1.11 (td, J=12.44, 2.91 Hz, 3H) 1.43-1.55 (m, 2H) 1.67-1.78 (m, J=7.14, 7.14, 6.95, 6.57 Hz, 2H) 1.79-1.89 (m, 3H) 2.02 (d, J=7.33 Hz, 2H) 2.14 (t, J=7.33 Hz, 1H) 2.47 (s, 1H) 7.29 (d, J=8.34 Hz, 2H) 7.75 (d, J=8.59 Hz, 1H) 7.88-7.95 (m, 2H) 8.31 (dd, J=8.46, 2.40 Hz, 1H) 8.43 (dd, J=8.46, 2.15 Hz, 1H) 8.97 (d, J=2.27 Hz, 1H) 9.08 (d, J=1.52 Hz, 1H)

Alternatively, the methyl ester can be dissolved in THF and treated with aqueous sodium hydroxide (4 equiv). The mixture can then be stirred at 50 degrees for 12 hours, at which point water may be added and most of the organic solvent may be removed under reduced pressure. Addition of acetonitrile followed by cooling may yield a precipitate which can be isolated by filtration to afford the title compound as the corresponding sodium salt.

Following analogous procedures, the following compounds may also be prepared:

| Example | Name | LC rt | Method | (M + H)+ |
|---|---|---|---|---|
| Ex. 8-2 | {4-[4-(5-Isopropylcarbamoyl-pyridin-2-yl)-phenyl]-cyclohexyl}-acetic acid | 1.19 | A | 381.1 |
| Ex. 8-3 | {4-[4-(6-Carbamoyl-pyridin-2-yl)-phenyl]-cyclohexyl}-acetic acid | 1.13 | A | 338.8 |
| Ex. 8-4 | {4-[4-(6-Isopropylcarbamoyl-pyridin-2-yl)-phenyl]-cyclohexyl}-acetic acid | 1.18 | A | 380.9 |

The present invention also covers any salts of the hereinabove described examples. In particular, the potassium, sodium, hydrochloric, methansulfonic, phosphoric, sufuric acids salts, tert-butyl amine, and diethylamine. The salts can be prepared by the herein described methods.

The invention claimed is:
1. The compound of Formula I:

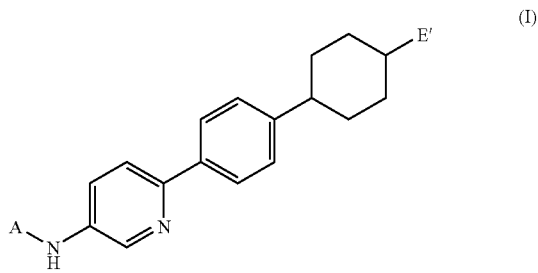

A is substituted or unsubstituted cycloalkyl, substituted or unsubstituted aryl, or substituted or unsubstituted heterocyclyl E' is —L2-E, —L2- is a divalent residue:

—[R$^1$]$_a$—[R$^2$]$_b$—[C(O)]$_c$—[N(R$^3$)]$_d$—[R$^4$]$_e$—[R$^5$]$_f$— selected from the group consisting of:
a divalent alkyl group having from 1 to 4 carbon atoms
a divalent alkenyl group having from 2 to 3 carbon atoms —C(O)—,
—C(O)—[R⁴]ₑ—R⁵—, wherein
  e is 0 and R⁵ is selected from the group consisting of a divalent substituted or unsubstituted C₁-C₄ alkyl group, C₄-C₈ cycloalkyl group, phenyl group or 5- or 6-membered heterocyclyl group, or
  e is 1, R⁴ is a divalent substituted or unsubstituted C₁-C₄ alkyl group, and R⁵ is a divalent substituted or unsubstituted C₄-C₈ cycloalkyl cycloalkyl group, phenyl group or 5- or 6-membered heterocyclyl group,
—R¹—R²—, wherein R¹ is a divalent substituted or unsubstituted C₁-C₄ alkyl group and R² is a divalent substituted or unsubstituted C₄-C₈ cycloalkyl group, phenyl group or 5- or 6-membered heterocyclyl group,
—C(O)—NH—,
—(CH₂)₁₋₃—C(O)—NH—(CH₂)₁₋₃—,
—C(O)—NH—R⁴—, wherein R⁴ is selected from a divalent substituted or unsubstituted C₁₋₇ alkyl group, cyclohexyl group or cyclopentyl group,
—C(O)—N(R³)—R⁴—, wherein R³ and R⁴ and the N-atom together form a pyrrolidine ring or a piperidine ring,
E is selected from the group consisting of:
  COOH,
  a carbocylic ester,
  a carboxamide,
  —S(O)₂—OH,
  —S(O)₂—NHR⁶, wherein R⁶ is selected from hydrogen, a C₁-C₈ alkyl group, a cycloalkyl group, a substituted or unsubstituted aryl group, a substituted or unsubstituted heterocyclyl group, or a carboxylic acid ester group, or pharmaceutically acceptable salt thereof.

2. The compound according to claim 1 of Formula II:

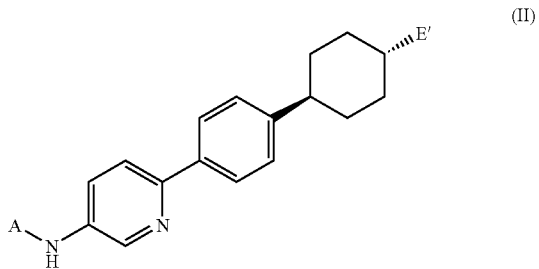

(II)

A is substituted or unsubstituted cycloalkyl, substituted or unsubstituted aryl, or substituted or unsubstituted heterocyclyl,
E' is -L2-E,
-L2- is a divalent residue:

—[R¹]ₐ—[R²]ᵦ—[C(O)]ᵧ—[N(R³)]ᵨ—[R⁴]ₑ—[R⁵]f— selected from the group consisting of:
  a divalent alkyl group having from 1 to 4 carbon atoms
  a divalent alkenyl group having from 2 to 3 carbon atoms
  —C(O)—,
  —C(O)—[R⁴]ₑ—R⁵—, wherein
    e is 0 and R⁵ is selected from the group consisting of a divalent substituted or unsubstituted C₁-C₄ alkyl group, C₄-C₈ cycloalkyl group, phenyl group or 5- or 6-membered heterocyclyl group, or
    e is 1, R⁴ is a divalent substituted or unsubstituted C₁-C₄ alkyl group, and R⁵ is a divalent substituted or unsubstituted C₄-C₈ cycloalkyl cycloalkyl group, phenyl group or 5- or 6-membered heterocyclyl group,
  —R¹—R²—, wherein R¹ is a divalent substituted or unsubstituted C₁-C₄ alkyl group and R² is a divalent substituted or unsubstituted C₄-C₈ cycloalkyl group, phenyl group or 5- or 6-membered heterocyclyl group,
  —C(O)—NH—,
  —(CH₂)₁₋₃—C(O)—NH—(CH₂)₁₋₃—,
  —C(O)—NH—R⁴—, wherein R⁴ is selected from a divalent substituted or unsubstituted C₁₋₇ alkyl group, cyclohexyl group or cyclopentyl group,
  —C(O)—N(R³)—R⁴—, wherein R³ and R⁴ and the N-atom together form a pyrrolidine ring or a piperidine ring,
E is selected from the group consisting of:
  COOH,
  a carbocylic ester,
  a carboxamide,
  —S(O)₂—OH,
  —S(O)₂—NHR⁶, wherein R⁶ is selected from hydrogen, a C₁-C₈ alkyl group, a cycloalkyl group, a substituted or unsubstituted aryl group, a substituted or unsubstituted heterocyclyl group, or a carboxylic acid ester group, or pharmaceutically acceptable salt thereof.

3. The compound of claim 1, wherein A is selected from substituted or unsubstituted phenyl, substituted or unsubstituted pyridine, substituted or unsubstituted cyclohexyl, substituted or unsubstituted isoxazole, substituted or unsubstituted oxadiazole, or substituted or unsubstituted pyrazole, and a pharmaceutically acceptable salt thereof.

4. The compound of claim 1, wherein E' is —C(O)OH, —CH₂—C(O)OH, —CH₂-heterocyclyl, or a pharmaceutically acceptable salt thereof.

5. The compound of claim 1, selected from the group consisting of:
  (4-{4-[5-(6-Trifluoromethyl-pyridin-3-ylamino)-pyridin-2-yl]-phenyl}-cyclohexyl)-acetic acid,
  (4-{4-[5-(Pyridin-2-ylamino)-pyridin-2-yl]-phenyl}-cyclohexyl)-acetic acid,
  {4-[4-(5-Phenylaminopyridin-2-yl)-phenyl]-cyclohexyl}-acetic acid,
  (4-{4-[5-(5-Cyanopyridin-3-ylamino)-pyridin-2-yl]-phenyl}-cyclohexyl)-acetic acid,
  (4-{4-[5-(5-Trifluoromethylpyridin-2-ylamino)-pyridin-2-yl]-phenyl}-cyclohexyl)-acetic acid,
  (4-{4-[5-(4-Trifluoromethylphenylamino)-pyridin-2-yl]-phenyl}-cyclohexyl)-acetic acid,
  (4-{4-[5-(5-Methylpyridin-2-ylamino)-pyridin-2-yl]-phenyl}-cyclohexyl)-acetic acid,
  (4-{4-[5-(5-Trifluoromethylpyridin-2-ylamino)-pyridin-2-yl]-phenyl}-cyclohexyl)-acetic acid methyl ester,
  (4-{4-[5-(5-Chloropyridin-2-ylamino)-pyridin-2-yl]-phenyl}-cyclohexyl)-acetic acid,
  (4-{4-[5-(6-Methoxypyridin-3-ylamino)-pyridin-2-yl]-phenyl}-cyclohexyl)-acetic acid,
  (4-{4-[5-(5-Fluoropyridin-2-ylamino)-pyridin-2-yl]-phenyl}-cyclohexyl)-acetic acid,
  (4-{4-[5-(6-Acetylaminopyridin-3-ylamino)-pyridin-2-yl]-phenyl}-cyclohexyl)-acetic acid,
  (4-{4-[5-(3-Fluoro-phenylamino)-pyridin-2-yl]-phenyl}-cyclohexyl)-acetic acid,
  (4-{4-[5-(3-Chloro-phenylamino)-pyridin-2-yl]-phenyl}-cyclohexyl)-acetic acid,
  (4-{4-[5-(1-Methyl-1H-pyrazol-3-ylamino)-pyridin-2-yl]-phenyl}-cyclohexyl)-acetic acid, (4-{4-[5-(5-Fluoro-6-methoxy-pyridin-3-ylamino)-pyridin-2-yl]-phenyl}-cyclohexyl)-acetic acid,
(4-{4-[5-(Isoxazol-3-ylamino)-pyridin-2-yl]-phenyl}-cyclohexyl)-acetic acid,
(4-{4-[5-(5-Fluoro-pyridin-3-ylamino)-pyridin-2-yl]-phenyl}-cyclohexyl)-acetic acid,
(4-{4-[5-(6-Isopropoxy-pyridin-3-ylamino)-pyridin-2-yl]-phenyl}-cyclohexyl)-acetic acid,
(4-{4-[5-(5-Bromo-pyridin-2-ylamino)-pyridin-2-yl]-phenyl}-cyclohexyl)-acetic acid,
(4-{4-[5-(2-Methoxy-pyrimidin-5-ylamino)-pyridin-2-yl]-phenyl}-cyclohexyl)-acetic acid,
(4-{4-[5-(6-Methylsulfanyl-pyridin-3-ylamino)-pyridin-2-yl]-phenyl}-cyclohexyl)-acetic acid,
(4-{4-[5-([1,2,4]Triazin-3-ylamino)-pyridin-2-yl]-phenyl}-cyclohexyl)-acetic acid,
(4-{4-[5-(2-Dimethylamino-pyrimidin-5-ylamino)-pyridin-2-yl]-phenyl}-cyclohexyl)-acetic acid,
(4-{4-[5-(5-Methylsulfanyl-pyridin-2-ylamino)-pyridin-2-yl]-phenyl}-cyclohexyl)-acetic acid,
(4-{4-[5-(3,5-Difluoro-pyridin-2-ylamino)-pyridin-2-yl]-phenyl}-cyclohexyl)-acetic acid,
(4-{4-[5-(6-Trifluoromethyl-pyridin-3-ylamino)-pyridin-2-yl]-phenyl}-cyclohexyl)-acetic acid methyl ester,
(4-{4-[5-(5-Chloro-6-methoxy-pyridin-3-ylamino)-pyridin-2-yl]-phenyl}-cyclohexyl)-acetic acid,
(4-{4-[5-(5-Fluoro-4-methyl-pyridin-2-ylamino)-pyridin-2-yl]-phenyl}-cyclohexyl)-acetic acid,
(4-{4-[5-(3-Chloro-5-methyl-pyridin-2-ylamino)-pyridin-2-yl]-phenyl}-cyclohexyl)-acetic acid,
(4-{4-[5-(5-Difluoromethyl-6-methoxy-pyridin-3-ylamino)-pyridin-2-yl]-phenyl}-cyclohexyl)-acetic acid,
(4-{4-[5-(5-Methanesulfonyl-pyridin-2-ylamino)-pyridin-2-yl]-phenyl}-cyclohexyl)-acetic acid,
(4-{4-[5-(1H-Benzoimidazol-2-ylamino)-pyridin-2-yl]-phenyl}-cyclohexyl)-acetic acid,
(4-{4-[5-(5-Trifluoromethyl-[1,3,4]oxadiazol-2-ylamino)-pyridin-2-yl]-phenyl}-cyclohexyl)-acetic acid,
(4-{4-[5-(6-Methyl-benzooxazol-2-ylamino)-pyridin-2-yl]-phenyl}-cyclohexyl)-acetic acid,
(4-{4-[5-(2-Methyl-5-trifluoromethyl-2H-pyrazol-3-ylamino)-pyridin-2-yl]-phenyl}-cyclohexyl)-acetic acid,
(4-{4-[5-(6-Chloro-benzooxazol-2-ylamino)-pyridin-2-yl]-phenyl}-cyclohexyl)-acetic acid methyl ester,
(4-{4-[5-(6-Chloro-benzooxazol-2-ylamino)-pyridin-2-yl]-phenyl}-cyclohexyl)-acetic acid,
(4-{4-[5-(5-Chloro-6-methoxy-benzooxazol-2-ylamino)-pyridin-2-yl]-phenyl}-cyclohexyl)-acetic acid,
(4-{4-[5-(5-tert-Butyl-[1,3,4]oxadiazol-2-ylamino)-pyridin-2-yl]-phenyl}-cyclohexyl)-acetic acid,
or a pharmaceutically acceptable salt thereof.

6. A compound according to claim 1 which is (4-{4-[5-(6-trifluoromethyl-pyridin-3-ylamino)-pyridin-2-yl]-phenyl}-cyclohexyl)-acetic acid, or a pharmaceutically acceptable salt thereof.

7. A compound according to claim 6 which is

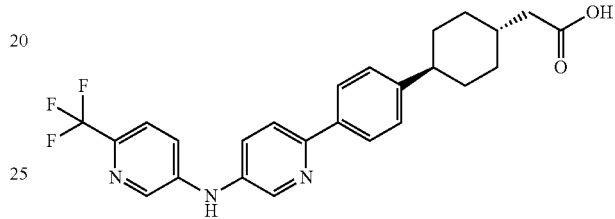

or a pharmaceutically acceptable salt thereof.

8. A compound according to claim 7 in sodium salt form.

9. A pharmaceutical composition, comprising:
the compound according to claim 1, and
a pharmaceutical acceptable carrier or excipient.

10. A pharmaceutical compositions comprising:
i) a compound according to claim 1,
ii) at least one compound selected from
   a) antidiabetic agents,
   b) hypolipidemic agents,
   c) anti-obesity agents,
   d) anti-hypertensive agents,
   e) agonists of peroxisome proliferator-activator receptors, and
iii) one or more pharmaceutically acceptable carriers.

* * * * *